United States Patent
Nakagawa et al.

(10) Patent No.: US 9,290,487 B2
(45) Date of Patent: Mar. 22, 2016

(54) PHARMACEUTICAL COMPOSITION FOR TREATING DIABETES

(71) Applicant: Ajinomoto Co., Inc., Chuo-ku (JP)

(72) Inventors: Tadakiyo Nakagawa, Kawasaki (JP); Kayo Matsumoto, Kawasaki (JP); Sen Takeshita, Kawasaki (JP); Tomomi Yoshida, Kawasaki (JP); Munetaka Tokumasu, Kawasaki (JP); Hiroki Inoue, Kawasaki (JP); Kaori Kobayashi, Kawasaki (JP)

(73) Assignee: AJINOMOTO CO., INC., Chuo-ku (JP)

( * ) Notice: Subject to any disclaimer, the term of this patent is extended or adjusted under 35 U.S.C. 154(b) by 0 days.

(21) Appl. No.: 14/268,323

(22) Filed: May 2, 2014

(65) Prior Publication Data

US 2014/0336376 A1 Nov. 13, 2014

Related U.S. Application Data

(63) Continuation of application No. PCT/JP2012/078516, filed on Nov. 2, 2012.

(30) Foreign Application Priority Data

| Nov. 4, 2011 | (JP) | ................................ 2011-242363 |
| Jul. 18, 2012 | (JP) | ................................ 2012-159862 |

(51) Int. Cl.

| C07D 413/12 | (2006.01) |
| C07D 405/12 | (2006.01) |
| C07D 207/16 | (2006.01) |
| C07D 403/12 | (2006.01) |
| C07D 409/12 | (2006.01) |
| C07D 307/80 | (2006.01) |
| A61K 31/343 | (2006.01) |

(Continued)

(52) U.S. Cl.
CPC ............ *C07D 413/12* (2013.01); *A61K 31/343* (2013.01); *A61K 31/397* (2013.01); *A61K 31/401* (2013.01); *A61K 31/404* (2013.01); *A61K 31/4025* (2013.01); *A61K 31/427* (2013.01); *A61K 31/536* (2013.01); *C07D 207/16* (2013.01); *C07D 307/79* (2013.01); *C07D 307/80* (2013.01); *C07D 403/12* (2013.01); *C07D 405/12* (2013.01); *C07D 409/12* (2013.01)

(58) Field of Classification Search
CPC .. C07D 413/12; C07D 405/12; C07D 207/16; C07D 403/12; C07D 409/12; C07D 307/80
USPC ............. 514/230.5, 412, 443, 456, 465, 469; 544/105; 548/525, 533, 465, 953; 549/462

See application file for complete search history.

(56) References Cited

U.S. PATENT DOCUMENTS

| 7,939,569 B1 | 5/2011 | Bolin et al. |
| 7,947,728 B1 | 5/2011 | Bolin et al. |

(Continued)

FOREIGN PATENT DOCUMENTS

| JP | 2007-506666 | 3/2007 |
| JP | 2008-521846 | 6/2008 |

(Continued)

OTHER PUBLICATIONS

Tetsuya Suga et al., "Igaku no ayumi" (Developments in Medical Science), vol. 220, No. 1, Jan. 6, 2007, pp. 75-80 (with partial English Translation).

(Continued)

*Primary Examiner* — Kahsay Habte
(74) *Attorney, Agent, or Firm* — Oblon, McClelland, Maier & Neustadt, L.L.P.

(57) ABSTRACT

Provided is a compound represented by the following general formula (I), or a pharmaceutically acceptable salt thereof. This novel compound has a glycogen-synthase activation ability, but activates a receptor PPAR to a low degree and is highly safe.

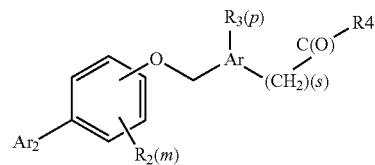

In the formula, Ar is an aromatic carbocyclic ring or a heterocyclic ring; and $Ar_2$ is represented by any one of the following rings and the like.

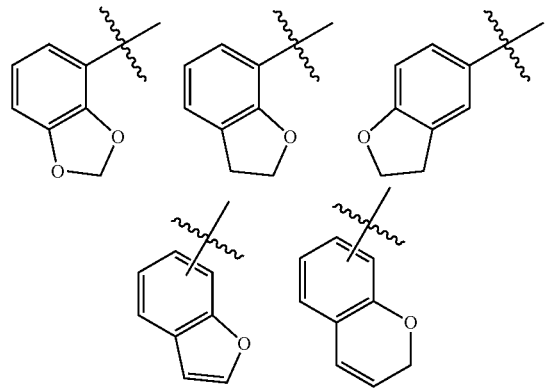

13 Claims, No Drawings

(51) Int. Cl.
*A61K 31/397* (2006.01)
*A61K 31/401* (2006.01)
*A61K 31/4025* (2006.01)
*A61K 31/404* (2006.01)
*A61K 31/427* (2006.01)
*A61K 31/536* (2006.01)
*C07D 307/79* (2006.01)

(56) References Cited

U.S. PATENT DOCUMENTS

| | | |
|---|---|---|
| 2004/0266856 A1 | 12/2004 | Chu et al. |
| 2006/0122256 A1 | 6/2006 | Gillespie et al. |
| 2008/0108662 A1 | 5/2008 | Chu et al. |
| 2008/0255198 A1 | 10/2008 | Chu et al. |
| 2009/0156635 A1 | 6/2009 | Gillespie et al. |
| 2011/0112147 A1 | 5/2011 | Bolin et al. |
| 2011/0112158 A1 | 5/2011 | Bolin et al. |
| 2011/0112161 A1 | 5/2011 | Bolin et al. |
| 2011/0118314 A1 | 5/2011 | Yun |
| 2011/0118322 A1 | 5/2011 | Bolin et al. |
| 2011/0130438 A1 | 6/2011 | Bolin et al. |
| 2011/0136792 A1 | 6/2011 | Bolin et al. |

FOREIGN PATENT DOCUMENTS

| | | |
|---|---|---|
| WO | 2005/000781 | 1/2005 |
| WO | 2006/058648 | 6/2006 |
| WO | WO 2006/102067 A1 | 9/2006 |
| WO | 2011/057956 | 5/2011 |
| WO | 2011/057959 | 5/2011 |
| WO | 2011/057993 | 5/2011 |
| WO | 2011/058122 | 5/2011 |
| WO | 2011/058154 | 5/2011 |
| WO | 2011/067174 | 6/2011 |
| WO | 2011/067266 | 6/2011 |

OTHER PUBLICATIONS

Yimin Qian, et al., "Design and Synthesis of 2-N-substituted indazolone derivatives as non-carboxylic acid glycogen synthase activators", Bioorganic & Medicinal Chemistry Letters 23, (2013), pp. 2936-2940.

Yimin Qian et a., "*N*-substituted sultam carboxylic acids as novel glycogen synthase activators", Med. Chem. Commun., 2013, 4, pp. 833-838.

David R. Bolin et al., "Discovery of Potent, Selective and Orally Efficacious Glycogen Synthase Activators as a Potential Treatment for Type 2 Diabetes", 239th National Meeting and Exposition, Mar. 21-25, 2010, San Francisco, MEDI529.

International Search Report issued Dec. 11, 2012, in Application No. PCT/JP2012/078516 (with English Translation).

Written Opinion issued Dec. 11, 2012, in PCT/JP2012/078516, filed Nov. 2, 2012 (with English translation).

Extended European Search Report issued Apr. 9, 2015 in Patent Application No. 12845716.5.

PHARMACEUTICAL COMPOSITION FOR TREATING DIABETES

CROSS REFERENCE TO RELATED APPLICATIONS

The present application is a continuation of International Application PCT/JP2012/078516, filed Nov. 2, 2012, the entire contents of which are incorporated herein by reference. International Application PCT/JP2012/078516 claims the benefits of priority to Japanese Application No. 2011-242363, filed Nov. 4, 2011, and Japanese Application No. 2012-159862, filed Jul. 18, 2012.

TECHNICAL FIELD

The present invention relates to a novel compound having a glycogen synthase-activating function, and to a pharmaceutical composition for treating diabetes, which contains the compound.

BACKGROUND ART

Diabetes mellitus is an important disease for people nowadays, and the incidence of diabetes has been an upward trend in recent years. Many therapeutic drugs for diabetes have been developed on the basis of mechanisms of onset of diabetes, and have been actually used. For example, an insulin sensitivity enhancer, an α-glycosidase inhibitor, an insulin secretion promoter, insulin preparation, and the like have been used alone or in combination of two or more.

Under such circumstances as described above, a technique has been under development, which is adopted to treat diabetes by activating glycogen synthase, which is a novel mechanism different from those of the aforementioned conventional therapeutic drugs for diabetes. Specifically, biaryloxymethylarenecarboxylic acids have been proposed as compounds capable of activating glycogen synthase (Patent Literatures 1 to 9).

Meanwhile, novel, pharmaceutically active compounds are required to be safe, for example, to have no side effect, in addition to a predetermined effect(s) for the disease treatment. Examining peroxisome proliferator-activated receptors PPARs has been proposed as means for drug safety evaluation (Non Patent Literature 1). This is due to the facts that: in experimental animals such as rats, administering certain drugs leads to hepatomegaly and significantly induces intrahepatic enzymes, and the long-term administration of the drugs causes liver cancer. The changes are characterized by significant proliferation of peroxisomes, which are organelles in the liver. It has been revealed that a receptor PPAR, especially a subfamily PPARα, activated by a peroxisome proliferator (PP) is involved in the mechanism of drug-liver peroxisome proliferation-liver carcinogenesis. This phenomenon has drawn attention at the drug safety evaluation (particularly, carcinogenicity evaluation) in the pharmaceutical drug development stage.

CITATION LIST

Patent Literatures

Patent Literature 1: WO2005/000781
Patent Literature 2: WO2006/058648
Patent Literature 3: WO2011/057956
Patent Literature 4: WO2011/057959
Patent Literature 5: WO2011/057993
Patent Literature 6: WO2011/058122
Patent Literature 7: WO2011/058154
Patent Literature 8: WO2011/067174
Patent Literature 9: WO2011/067266

Non Patent Literature

Non Patent Literature 1: Journal of Clinical and Experimental Medicine (Igaku No Ayumi), Vol. 220, No. 1 (2007) pp. 75-80

SUMMARY OF INVENTION

Problems to be Solved by the Invention

An object of the present invention is to provide a novel, highly safe compound, which has a glycogen-synthase activation ability but activates a receptor PPAR to a low degree.

Another object of the present invention is to provide a pharmaceutical composition containing the compound.

Another object of the present invention is to provide a pharmaceutical composition for treating diabetes, which contains the compound.

Still another object of the present invention is to provide a glycogen synthase activator containing the compound.

Solution to Problems

Focusing on biaryl rings of biaryloxymethylarenecarboxylic acid compounds described in Patent Literatures 1 to 9, the present invention has been made on the basis of the finding that the above objects can be efficiently achieved by the alteration and so forth to a fused heterocyclic ring, in which a 5-membered ring or a 6-membered ring containing an oxygen atom, a sulfur atom, a nitrogen atom, or the like as a ring-constituting atom is fused to a phenyl group located at an end.

Specifically, the present invention provides a compound represented by the following general formula (I), or a pharmaceutically acceptable salt thereof:

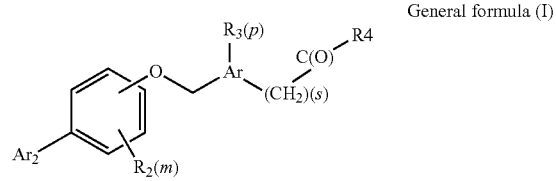

General formula (I)

wherein Ar is an aromatic carbocyclic ring or a heterocyclic ring;

$Ar_2$ is represented by any one of the following rings

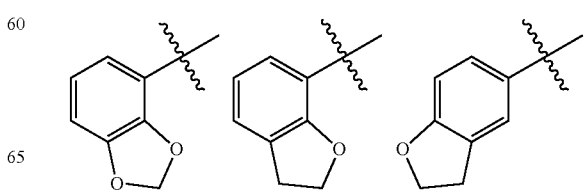

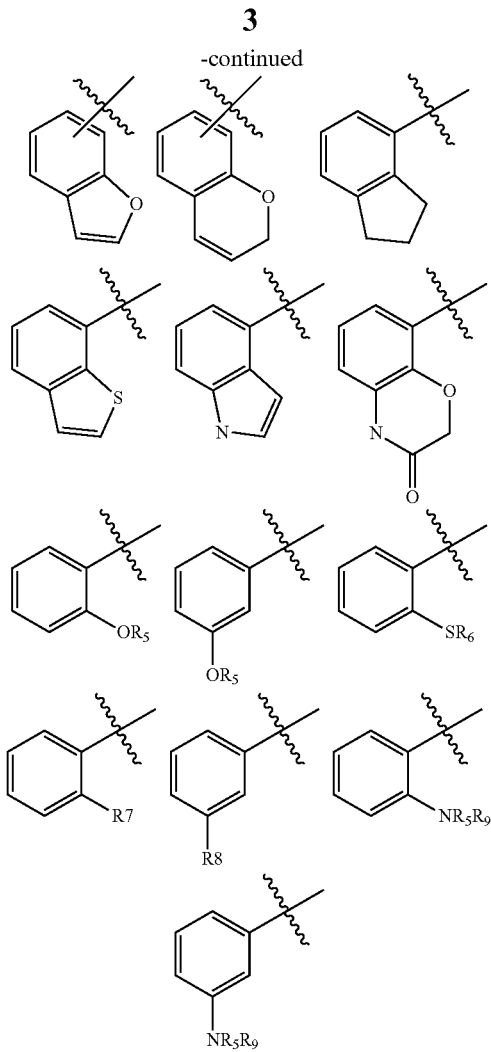

these rings may have a substituent, and the substituent is selected from the group consisting of acetamido, aminocarbonyl, benzyl, benzyloxy, a halogen, hydroxyl-lower alkyl, lower alkyl, lower alkoxy-lower alkyl, phenoxy, phenyl, a formyl group, a cyano group, a cyanoalkyl group, a hydroxyiminomethyl group, a hydroxyamidino group, an amino group, an aminoalkyl group, an alkylaminoalkyl group, a dialkylaminoalkyl group, lower alkoxy, and trifluoro-methoxy;

$R_2$ and $R_3$ are independently selected from the group consisting of lower alkyl, lower alkoxy, trifluoromethyl, a halogen, hydroxy, a hydroxyl-lower alkyl group, amino, alkylamino, dialkylamino, cyano, and nitro;

$R_4$ is an amino acid residue bonded to C(O) through a nitrogen atom of the amino acid;

$R_5$ is a cyanoalkyl group or -CD3, or is represented by any one of the following substituents

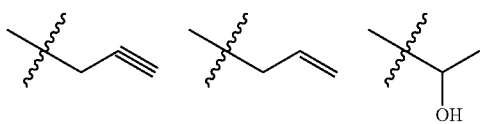

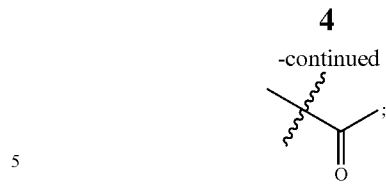

$R_6$ is hydrogen, a lower alkyl group, a cyanoalkyl group, a hydroxyalkyl group, or an alkoxyalkyl group, or is represented by any one of the following substituents

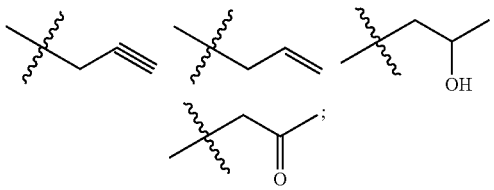

$R_7$ and $R_8$ are each a cyanoalkyl group, a formyl group, an alkoxycarbonyl group, or a hydroxyiminomethyl group;
$R_9$ is hydrogen or a lower alkyl group;
m is 0, 1, 2, 3, or 4;
p is 0, 1, or 2; and
s is 0, 1, or 2.

DESCRIPTION OF EMBODIMENTS

In a general formula (I), an aromatic carbocyclic ring includes aromatic carbocyclic rings such as a phenyl group and a naphthyl group. Meanwhile, a heterocyclic ring includes 5-membered to 8-membered heterocyclic rings containing, as a ring-constituting atom, at least one heteroatom selected from the group consisting of an oxygen atom, a nitrogen atom, and a sulfur atom. Among them, a furan group and a thiazole group are preferable.

In the general formula (I), a lower alkyl group and a lower alkoxy group preferably have 1 to 6 carbon atoms, more preferably have 1 to 3 carbon atoms. These may be linear or branched. In addition, an alkyl group and an alkoxy group in a cyanoalkyl group, an aminoalkyl group, an alkylaminoalkyl group, a dialkylaminoalkyl group, an alkylamino group, a dialkylamino group, a hydroxyalkyl group, an alkoxyalkyl group, and an alkoxycarbonyl group preferably have 1 to 18 carbon atoms, more preferably have 1 to 6 carbon atoms, and most preferably have 1 to 3 carbon atoms.

In the general formula (I), $R_2$ and $R_3$ are each preferably a hydrogen atom or a halogen, more preferably a hydrogen atom.

In the general formula (I), $R_5$ is preferably CH2CN, -CD3, —CH2CH=CH2, —CH2C≡CH, CH2C(O)CH3, or CH2CH(OH)CH3, while $R_6$ is preferably a methyl group, a hydrogen atom, CH2C(O)CH3, CH2CH2OH, or CH2CN. Additionally, D in -CD3 as $R_5$ represents deuterium.

In the general formula (I), $R_7$ and $R_8$ are each preferably a cyanomethyl group, a methoxycarbonyl group, a hydroxyiminomethyl group, or a formyl group. $R_9$ is preferably hydrogen.

An amino acid serving as an amino acid residue in the general formula (I) includes proline, sarcosine, azetidine-2-carboxylic acid, N-methylalanine, 2,5-dihydro-1H-pyrrole-2-carboxylic acid, and 1,3-thiazolidine-4-carboxylic acid. Among them, proline and sarcosine are preferable.

Here, $Ar_2$ preferably has one, two, or three substituents, one or two of which are preferably a halogen(s).

In the general formula (I), preferably m=0, p=0, and s=0.

In the general formula (I), Ar₂ is preferably represented by any one of the following rings which may have a substituent

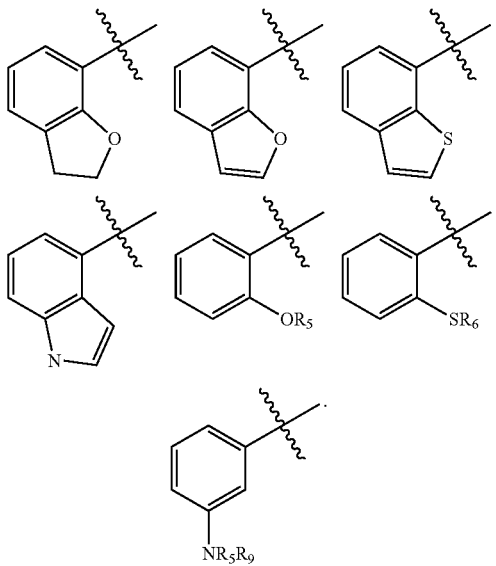

Of these, Ar₂ is particularly preferably represented by any one of the following rings which may have a substituent

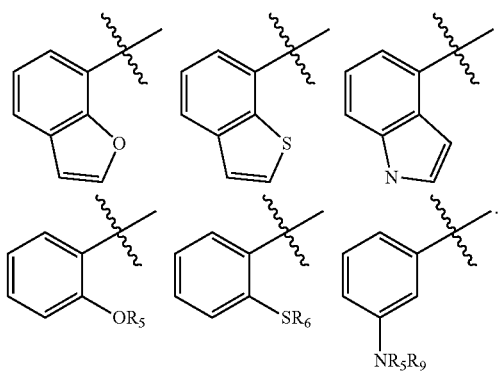

Alternatively, Ar₂ is preferably represented by any one of the following rings which may have a substituent

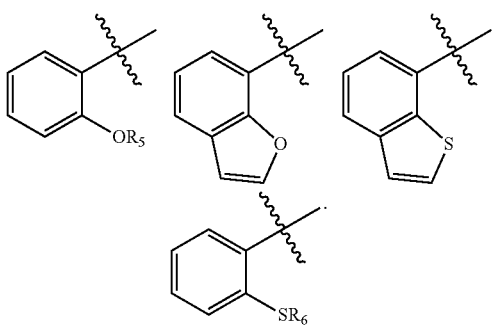

Further, particularly, the substituent of the above rings is particularly preferably a halogen, hydroxy-lower alkyl, a lower alkoxy-lower alkyl group, a formyl group, a cyano group, a hydroxyiminomethyl group, a dialkylaminoalkyl group, or a lower alkyl group.

A compound represented by the general formula (I) of the present invention and a pharmaceutically acceptable salt thereof can be synthesized according to the following synthesis scheme:

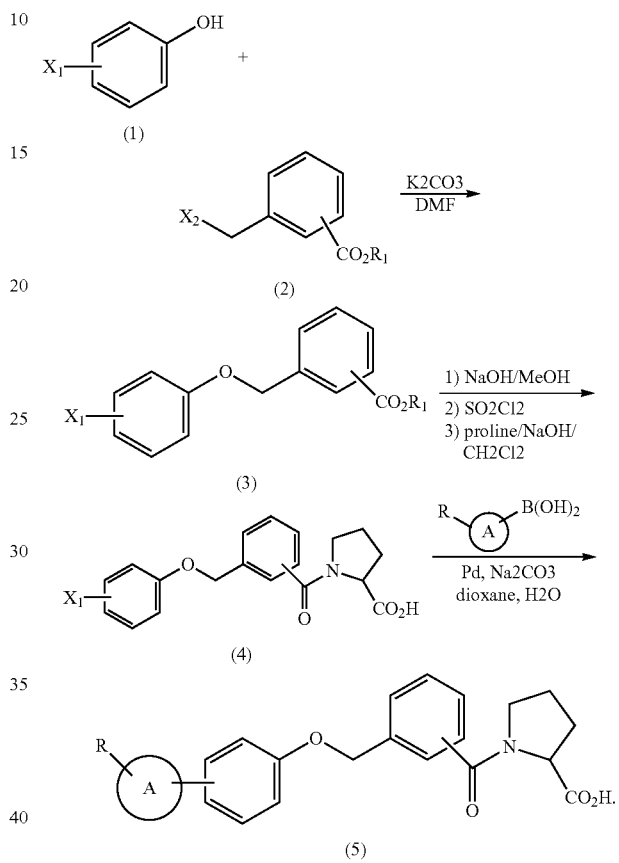

Here, a phenol derivative (1) having a halogen at X1 is reacted with a benzoic acid ester derivative (2) having a halogen at X2, for example, in a solvent such as N, N-dimethylformamide (hereinafter, DMF) in the presence of a base such as potassium carbonate, so that an ester derivative (3) can be obtained. This is hydrolyzed to a carboxylic acid, for example, in a solvent such as methanol in the presence of a base such as sodium hydroxide. After conversion to an acid chloride using for example thionyl chloride or the like, the resultant can be reacted with various amino acids, for example, proline, for example, in a solvent such as dichloromethane in the presence of a base such as sodium hydroxide to thereby obtain an amide (4). The amide (4) is subjected to a coupling reaction, for example, in a solvent such as dioxane or water in the presence of a base such as sodium carbonate, using various boronic acid derivatives, and Pd or the like as a catalyst, so that a compound (5) can be obtained by.

Alternatively, as shown in the following reaction equation, a phenol derivative (6) having a boronic acid derivative at X3 is reacted with a benzoic acid ester derivative (2) having a halogen at X2, for example, in a solvent such as DMF in the presence of a base such as potassium carbonate, so that an ester derivative (7) can be obtained. This is hydrolyzed to a carboxylic acid, for example, in a solvent such as methanol in the presence of a base such as sodium hydroxide. The resultant can be reacted with various amino acids, for example, proline, for example, in a solvent such as dichloromethane, using for example a condensation agent to thereby obtain an ester. The resultant can be hydrolyzed, for example, in a solvent such as methanol in the presence of a base such as sodium hydroxide to thereby obtain an amide (8). The amide (8) is subjected to a coupling reaction, for example, in a solvent such as dioxane or water in the presence of a base such as sodium carbonate using various halogen derivatives, and Pd or the like as a catalyst, so that the compound (5) can be obtained.

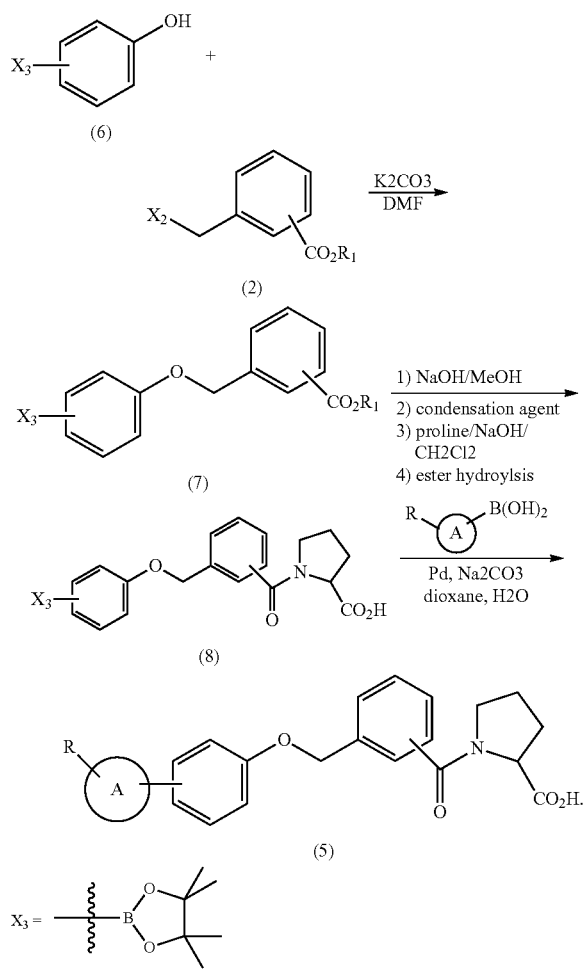

In the present invention, in a case where the compound represented by the general formula (I) can be made in the form of a salt, it is only necessary that the salt be pharmaceutically acceptable. For example, in a case where an acidic group such as a carboxyl group is present in the formula, the pharmaceutically acceptable salt for such an acidic group includes an ammonium salt; salts with alkali metals such as sodium and potassium; salts with alkaline earth metals such as calcium and magnesium; aluminium salts; zinc salts; salts with organic amines such as triethylamine, ethanolamine, morpholine, piperidine, and dicyclohexylamine; and salts with basic amino acids such as arginine and lysine. Of these, sodium is preferably used.

In a case where a basic group is present in the formula, the pharmaceutically acceptable salt for such a basic group includes salts with inorganic acids such as hydrochloric acid, sulfuric acid, phosphoric acid, nitric acid, hydrobromic acid; salts with organic carboxylic acids such as acetic acid, trifluoroacetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, and malic acid; and salts with organic sulfonic acids such as methanesulfonic acid, benzenesulfonic acid, and p-toluenesulfonic acid. Of these, hydrochloric acid and trifluoroacetic acid are preferably used.

As a method for forming the salt, the compound represented by the general formula (I) and a required acid or base may be mixed at an appropriate quantity ratio in a solvent or a dispersant, or the salt can be obtained from another salt form by cation exchange or anion exchange.

The compound of the present invention also includes solvates, for example, hydrates, alcohol adducts, and the like of the compound represented by the general formula (I).

The compound of the present invention may also be converted to a prodrug. In the present invention, a prodrug refers to a compound that is converted in vivo so that the compound of the present invention can be produced. For example, in a case where the active form contains a carboxyl group or a phosphate group, the prodrug includes esters of the carboxyl group or the phosphate group, amides thereof, and the like. Meanwhile, in a case where the active form contains an amino group, the prodrug includes amides of the amino group, carbamates thereof, and the like. In a case where the active form contains a hydroxyl group, the prodrug includes esters of the hydroxyl group, carbonates thereof, carbamates thereof, and the like. When the compound of the present invention is converted to a prodrug, the prodrug may be bonded to an amino acid or sugars.

The present invention includes all isotopes of the compound represented by the general formula (I). The isotopes of the compound of the present invention each have at least one atom substituted with an atom having the same atomic number (proton number) but having a different mass number (sum of the numbers of protons and neutrons). Examples of the isotopes included in the compound of the present invention are: a hydrogen atom, a carbon atom, a nitrogen atom, an oxygen atom, a phosphorus atom, a sulfur atom, a fluorine atom, a chlorine atom, and the like, including 2H, 3H, 13C, 14C, 15N, 17O, 18O, 31P, 32P, 35S, 18F, 36Cl, and the like. Particularly, unstable radioisotopes such as 3H and 14C that release radiation and emit neutrons are useful for a body tissue distribution test and the like to be conducted on a pharmaceutical drug or compound. A stable isotope does not decay, so that the abundance hardly changes and no radiation is released; accordingly, such a stable isotope can be used safely. The isotope of the compound of the present invention can be converted according to a conventional method by replacing a reagent used for synthesis with a reagent containing a corresponding isotope.

A pharmaceutical composition of the present invention can be preferably used for treatment of diseases mediated by a decrease in the activity of glycogen synthase. Particularly, the pharmaceutical composition of the present invention can be preferably used for treatment of diabetes, especially, type 2 diabetes and impaired glucose tolerance.

The pharmaceutical composition and a glycogen synthase activator of the present invention vary, depending on the administration target, the administration route, the target disease, the symptoms, and the like. Nevertheless, the pharmaceutical composition and the glycogen synthase activator of the present invention are preferably used for oral administration as the administration route. The dose in a single administration is preferably 1 mg to 1000 mg in terms of the active ingredient/person, more preferably 1 mg to 100 mg in terms of the active ingredient/person. This dose is desirably administered one time to three times a day.

The pharmaceutical composition and the glycogen synthase activator of the present invention contain the compound represented by the general formula (I) and/or the pharmaceutically acceptable salt thereof as the active ingredient, but may also contain various ingredients generally used in orally administered drugs, for example, a pharmaceutically or physiologically acceptable solid or liquid carrier, additive, and the like.

Examples of the carrier include glucose, lactose, sucrose, starches, mannitol, dextrins, fatty acid glycerides, polyethylene glycol, hydroxymethyl starches, ethylene glycol, polyoxyethylene sorbitan fatty acid esters, gelatins, albumins, amino acids, water, salines, and the like. In addition, as necessary, commonly-used additives such as a stabilizer, a moisturizer, an emulsifier, a binder, and an isotonic agent can also be added as appropriate.

The additives are not particularly limited, as long as they are used in accordance with their purposes and also generally used for the purposes. Specifically, examples thereof include flavors, sugars, sweeteners, food fiber, vitamins, amino acids such as monosodium glutamate (MSG), nucleic acids such as inosine monophosphate (IMP), inorganic salts such as sodium chloride, water, and the like.

The pharmaceutical composition and the glycogen synthase activator of the present invention can be used in orally administrable forms, such as dry powder, paste, and solution, without limitation to physical properties.

Examples of such an orally administrable form include tablets (including sugar coated tablets, film coated tablets, sublingual tablets, and orally disintegrating tablets), capsules (including soft capsules and microcapsules), granules, powders, troches, syrups, emulsions, suspensions, films (e.g., orally disintegrating films), lyophilized formulations, and the like.

Alternatively, the pharmaceutical composition and the glycogen synthase activator of the present invention can also be used in the form of parenteral preparations such as injections (e.g., subcutaneous injections, intravenous injections, intramuscular injections, intraperitoneal injections, drips), external preparations (e.g., transdermal preparations, ointments), suppositories (e.g., rectal suppositories, vaginal suppositories), pellets, intranasal agents, transpulmonary agents (inhalants), and eye drops.

Each of these can be safely administered orally or parenterally (e.g., locally, rectally, intravenously administered). These preparations may be controlled-release preparations such as immediate-release preparations or sustained-release preparations (e.g., sustained-release microcapsules). These preparations can be prepared by pharmaceutically common means.

Additionally, the pharmaceutical composition and the glycogen synthase activator of the present invention can be used in combination with other antidiabetic drugs, drugs for diabetic complications, anti-hyperlipemia drugs, antihypertensives, and/or anti-obesity drugs (hereinafter, abbreviated as combination drugs). These combination drugs may be low in molecular weight, or may be high-molecular-weight proteins, polypeptides, antibodies, nucleic acids (including antisense nucleic acids, siRNAs, shRNAs), vaccines, or the like. These combination drugs may be used alone or in combination of two or more.

The administration timing of the pharmaceutical composition and the glycogen synthase activator of the present invention or the combination drugs is not limited. These may be administered to the administration target simultaneously, or may be administered with an interval.

Note that the antidiabetic drugs include insulin preparations (e.g., animal insulin preparations extracted from the pancreas of cattle or pigs; human insulin preparations synthesized by genetic engineering using *Escherichia coli* or yeast; insulin zinc; protamine insulin zinc; insulin fragments or derivatives (e.g., INS-1), oral insulin preparations), insulin resistance improvers (e.g., pioglitazone or salts thereof (preferably hydrochloride), rosiglitazone or salts thereof (preferably maleate), tesaglitazar), ragaglitazar, muraglitazar, edaglitazone, metaglidasen, naveglitazar, AMG-131, THR-0921), α-glucosidase inhibitors (e.g., voglibose, acarbose, miglitol, emiglitate), biguanides (e.g., metformin, buformin, or salts thereof (e.g., hydrochloride, fumarate, succinate)), insulin secretion promoters [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide, or calcium salt hydrates thereof], dipeptidyl peptidase IV inhibitors (e.g., alogliptin, vildagliptin, sitagliptin, saxagliptin, T-6666, TS-021), β3 agonists (e.g., AJ-9677), GPR40 agonists, GPR120 agonists, GLP-1 receptor agonists [e.g., GLP-1, GLP-1MR agent, NN-2211, AC-2993 (exendin-4), BIM-51077, Aib(8.35)hGLP-1(7.37)NH$_2$, CJC-1131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLT (sodium-glucose cotransporter) inhibitors (e.g., dapagliflozin, canagliflozin, ipragliflozin, BI-10773), 11β-hydroxysteroid dehydrogenase inhibitors (e.g., BVT-3498), adiponectin or agonists thereof, IKK inhibitors (e.g., AS-2868), leptin resistance improvers, somatostatin receptor agonists, glucokinase activators (e.g., Ro-28-1675), GIP (glucose-dependent insulinotropic peptide), and the like.

Further, the compound represented by the general formula (I) and/or the pharmaceutically acceptable salts thereof can be used in such forms used for a supplement or the like that they are enclosed in a granule, a tablet, a gelatin capsule, or the like.

Next, the present invention will be specifically described by way of Examples.

EXAMPLES

Hereinafter, the present invention will be described in more details by way of Examples. However, the present invention is not limited to these Examples.

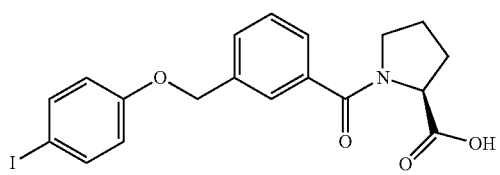

Intermediate 1

Synthesis of 1-{3-[(4-iodophenoxy)methyl]benzoyl}-L-proline

N,N-dimethylformamide (hereinafter, DMF) (100 mL), potassium carbonate (1.1 g, 7.8 mmol), and methyl 3-(bromomethyl)benzoate (1.2 g, 5.2 mmol) were added to 4-iodophenol (1.2 g, 5.5 mmol), and stirred at room temperature overnight. Ethyl acetate was used as an extraction solvent, and after washing with water, a 1 N sodium hydroxide aqueous solution, and saturated brine, the resultant was dried over magnesium sulfate. The solvent was distilled away under reduced pressure. To the resulting residue (1.9 g, 5.2 mmol), tetrahydrofuran (hereinafter, THF) (10 mL), methanol (10 mL), and a 1 N sodium hydroxide aqueous solution (20 mL) were added, and stirred at room temperature for 4 hours. Ethyl acetate was used as an extraction solvent, and after washing with a 1 N hydrochloric acid aqueous solution and saturated brine, the resultant was dried over magnesium sulfate. The solvent was distilled away under reduced pressure. To the resulting residue, thionyl chloride (20 mL) was added, and stirred at 40° C. for 1 hour. After that, the solvent was distilled away under reduced pressure. To the resulting residue, dichloromethane (10 mL), a 1 N sodium hydroxide aqueous solution (15 mL), and L-proline (1.1 g, 9.2 mmol) were added, and stirred at room temperature overnight. The solvent was distilled away under reduced pressure. The resultant was washed with a 1 N hydrochloric acid aqueous solution and saturated brine, and then dried over magnesium sulfate. The solvent was distilled away under reduced pressure. The resulting residue was washed with a water-acetonitrile mixture solvent, and then dried to thus obtain the title compound.

Yield: 1.5 g (3.3 mmol), percentage yield: 64%
MS (ESI, m/z) 452 [M+H]$^+$
$^1$H NMR (DMSO-$d_6$, 400 MHz) δ 1.76-1.99 (m, 3H), 2.18-2.33 (m, 1H), 3.38-3.61 (m, 2H), 4.29-4.43 (m, 1H), 5.08-5.19 (m, 2H), 6.84-6.91 (m, 2H), 7.43-7.50 (m, 2H), 7.51-7.64 (m, 4H), 12.55 (br s, 1H).

Example 1

1-(3-{[4-(5-fluoro-2,3-dihydro-1-benzofuran-7-yl)phenoxy]methyl}benzoyl)-L-proline Step 1 Synthesis of
1,3-dibromo-2-(2-chloroethoxy)-5-fluorobenzene DMF (50 mL), 1-bromo-2-chloroethane (1.0 mL, 12 mmol), and potassium carbonate (1.7 g, 12 mmol) were added to 2,6-dibromo-4-fluorophenol (3.0 g, 11 mmol), and stirred at 50° C. overnight. Ethyl acetate was used as an extraction solvent, and after washing with water and saturated brine, and the resultant was dried over magnesium sulfate. The solvent was distilled away under reduced pressure. The resulting residue was purified by silica gel column chromatography to thus obtain the title compound.

Yield: 2.5 g (7.4 mmol), percentage yield: 56%
MS (ESI, m/z) 333 [M+H]$^+$

Step 2 Synthesis of
7-bromo-5-fluoro-2,3-dihydro-1-benzofuran

To the compound (2.5 g, 7.4 mmol) obtained in Step 1, THF (50 mL) was added. At −78° C., a 2.6 M n-butyllithium/n-hexane solution (2.9 mL, 7.5 mmol) was added thereto and stirred for 1 hour, and then stirred at room temperature overnight. The solvent was distilled away under reduced pressure. The resulting residue was subjected to reversed-phase HPLC using ODS as a filler, and eluted with a mixture solution of water and acetonitrile, which contained trifluoroacetic acid at 0.1% (v/v). The target fraction was lyophilized to thus obtain the title compound.

Yield: 300 mg (1.4 mmol), percentage yield: 19%
MS (ESI, m/z) 218 [M+H]$^+$

Step 3 Synthesis of 3-{[4-(5-fluoro-2,3-dihydro-1-benzofuran-7-yl)phenoxy]methyl}benzoic acid To the compound (300 mg, 1.4 mmol) obtained in Step 2, 4-hydroxyphenylboronic acid (230 mg, 1.7 mmol), sodium carbonate (292 mg, 2.8 mmol), tetrakis(triphenylphosphine)palladium(0) (hereinafter, Pd(PPh3)4) (catalytic amount), 1,4-dioxane (10 mL), water (3 mL) were added, and stirred at 90° C. for 2 hours. The solvent was distilled away under reduced pressure. Ethyl acetate was used as an extraction solvent, and after washing with a 1 N hydrochloric acid aqueous solution and saturated brine, the resultant was dried over magnesium sulfate. The solvent was distilled away under reduced pressure. To the resulting residue, DMF (10 ml), potassium carbonate (280 mg, 2.8 mmol), and methyl 3-(bromomethyl)benzoate (470 mg, 2.1 mmol) were added, and stirred at 50° C. overnight. Ethyl acetate was used as an extraction solvent, and after washing with water, a 1 N sodium hydroxide aqueous solution, and saturated brine, the resultant was dried over magnesium sulfate. The solvent was distilled away under reduced pressure. To the resulting residue, THF (5 mL), methanol (5 mL), and a 1 N sodium hydroxide aqueous solution (10 mL) were added, and stirred at room temperature for 4 hours. The solvent was distilled away under reduced pressure. Ethyl acetate was used as an extraction solvent, and after washing with a 1 N hydrochloric acid aqueous solution and saturated brine, the resultant was dried over magnesium sulfate. After the solvent was distilled away under reduced pressure, the resulting residue was washed with a water-acetonitrile mixture solvent, and then dried to thus obtain the title compound.

Yield: 150 mg (0.41 mmol), percentage yield: 29%
MS (ESI, m/z) 365 [M+H]$^+$

Step 4 Synthesis of Compound of Example 1

To the compound (30 mg, 0.082 mmol) obtained in Step 3, thionyl chloride (2 mL) was added, and stirred at 40° C. for 1 hour. After that, the solvent was distilled away under reduced pressure. To the resulting residue, dichloromethane (4 mL), a 1 N sodium hydroxide aqueous solution (2 mL), and L-proline (30 mg, 0.26 mmol) were added, and stirred at room temperature overnight. The solvent was distilled away under reduced pressure. The resultant was washed with a 1 N hydrochloric acid aqueous solution and saturated brine, and then dried over magnesium sulfate. The solvent was distilled away under reduced pressure. The resulting residue was purified by reversed-phase HPLC in the same manner as in Step 2 to thus obtain the title compound.

Yield: 7 mg (0.015 mmol), percentage yield: 18%
MS (ESI, m/z) 462 [M+H]$^+$

Example 2

N-(3-{[4-(5-fluoro-2,3-dihydro-1-benzofuran-7-yl)phenoxy]methyl}benzoyl)-N-methylglycine An operation similar to that in Step 4 of Example 1 was performed using N-methylglycine in place of L-proline to thus obtain the title compound.

Yield: 7.5 mg (0.0172 mmol), percentage yield: 20%
MS (ESI, m/z) 436 [M+H]$^+$

Example 3

1-(3-{[4-(4-fluoro-1-benzofuran-7-yl)phenoxy]methyl}benzoyl)-L-proline

To the intermediate 1 (32 mg, 0.0710 mmol), 4-fluorobenzofuran-7-boronic acid (15.3 mg, 0.0852 mmol), sodium carbonate (16.6 mg, 0.156 mmol), and [1,1'-bis(diphenylphosphino)ferrocene]dichloropalladium(II) (hereinafter, Pd(dppf)Cl2) (catalytic amount), 1,4-dioxane (0.75 mL), and water (0.25 mL) were added, and stirred at 105° C. for 1 hour and a half. The insoluble material was filtered off, and the resultant was purified by reversed-phase HPLC in the same manner as in Step 2 of Example 1 to thus obtain the title compound.

Yield: 21.3 mg (0.0464 mmol), percentage yield: 65%
MS (ESI, m/z) 460 [M+H]$^+$
$^1$H NMR (DMSO-d$_6$, 400 MHz) δ 1.75-2.35 (m, 4H), 3.39-3.63 (m, 2H), 4.32-4.44 (m, 1H), 5.16-5.28 (m, 2H), 7.13-7.21 (m, 4H), 7.46-7.64 (m, 5H), 7.77 (d, J=8.8 Hz, 2H), 8.12 (d, J=2.2 Hz, 1H), 12.53 (br s, 1H).

Example 4

1-(3-{[4-(1,3-benzodioxol-4-yl)phenoxy]methyl}benzoyl)-L-proline

An operation similar to that in Example 3 was performed using 2,3-methylenedioxyphenylboronic acid in place of 4-fluorobenzofuran-7-boronic acid to thus obtain the title compound.

Yield: 23.5 mg (0.0528 mmol), percentage yield: 66%
MS (ESI, m/z) 446 [M+H]$^+$
$^1$H NMR (DMSO-d$_6$, 400 MHz) δ 1.74-2.35 (m, 4H), 3.39-3.63 (m, 2H), 4.31-4.45 (m, 1H), 5.13-5.27 (m, 2H), 6.05 (s, 1H), 6.85-6.94 (m, 2H), 7.06-7.14 (m, 3H), 7.31-7.62 (m, 4H), 7.68 (d, J=8.8 Hz, 2H), 12.54 (br s, 1H).

Example 5

1-(3-{[4-(2,3-dihydro-1-benzofuran-7-yl)phenoxy]methyl}benzoyl-L-proline

An operation similar to that in Example 3 was performed using 2,3-dihydro-1-benzofuran-7-boronic acid in place of 4-fluorobenzofuran-7-boronic acid to thus obtain the title compound.

Yield: 29.9 mg (0.0674 mmol), percentage yield: 80%
MS (ESI, m/z) 444 [M+H]$^+$
$^1$H NMR (DMSO-d$_6$, 400 MHz) δ 1.73-2.32 (m, 4H), 3.22 (t, J=8.7 Hz, 2H), 3.58 (s, 2H), 4.32-4.44 (m, 1H), 4.55 (t, J=8.7 Hz, 2H), 5.11-5.25 (m, 2H), 6.89 (t, J=7.5 Hz, 1H), 7.03-7.10 (m, 2H), 7.14-7.20 (m, 1H), 7.25 (d, J=7.5 Hz, 1H), 7.30-7.52 (m, 2H), 7.54-7.66 (m, 4H).

Example 6

1-(3-{[4-(1-benzofuran-5-yl)phenoxy]methyl}benzoyl-L-proline

An operation similar to that in Example 3 was performed using benzofuran-5-boronic acid in place of 4-fluorobenzofuran-7-boronic acid to thus obtain the title compound.

Yield: 16.4 mg (0.0371 mmol), percentage yield: 54%
MS (ESI, m/z) 442 [M+H]$^+$
$^1$H NMR (DMSO-d$_6$, 400 MHz) δ 1.76-2.00 (m, 3H), 2.20-2.33 (m, 1H), 3.40-3.62 (m, 2H), 4.32-4.44 (m, 1H), 5.15-5.26 (m, 2H), 6.96-7.00 (m, 1H), 7.09-7.14 (m, 2H), 7.31-7.66 (m, 8H), 7.85 (d, J=1.6 Hz, 1H), 8.01 (d, J=2.2 Hz, 1H), 12.57 (br s, 1H).

Example 7

1-(3-{[4-(1-benzofuran-7-yl)phenoxy]methylbenzoyl-L-proline

An operation similar to that in Example 3 was performed using benzofuran-7-boronic acid in place of 4-fluorobenzofuran-7-boronic acid to thus obtain the title compound.

Yield: 20.6 mg (0.0467 mmol), percentage yield: 68%
MS (ESI, m/z) 442 [M+H]$^+$
$^1$H NMR (DMSO-d$_6$, 400 MHz) δ 1.73-2.35 (m, 4H), 3.42-3.63 (m, 2H), 4.45-4.32 (m, 1H), 5.17-5.29 (m, 2H), 7.03 (d, J=2.2 Hz, 1H), 7.13-7.23 (m, 2H), 7.25-7.70 (m, 7H), 7.75-7.89 (m, 2H), 8.05 (d, J=2.2 Hz, 1H), 12.59 (br s, 1H).

Example 8

1-(3-{[4-(2-methyl-1-benzofuran-7-yl)phenoxy]methyl}benzoyl-L-proline

Step 1 Synthesis of intermediate (A) 7-bromo-2-methyl-1-benzofuran and intermediate (B) 8-bromo-2H-chromene

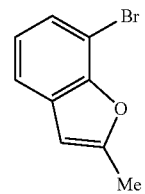

(A)

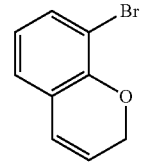

(B)

DMF (10 ml), propargyl bromide (1.14 m, 15.1 mmol), and potassium carbonate (4.0 g, 29 mmol) were added to 2-bromophenol (2.5 g, 14.5 mmol), and stirred at room temperature overnight. Ethyl acetate was used as an extraction solvent, and after washing with water and saturated brine, the resultant was dried over magnesium sulfate. The solvent was distilled away under reduced pressure. To the resulting residue, N,N-dimethylaniline (5 mL) was added, and stirred at 250° C. for 20 minutes. After that, cesium fluoride (690 mg, 3.6 mmol) was added thereto and stirred at 250° C. for 4 hours. The resultant was returned to room temperature, ethyl acetate was used as an extraction solvent, and a 1N hydrochloric acid aqueous solution was added. Thereafter, the insoluble material was filtered off with celite, and the resultant was washed with saturated brine, and then dried over magnesium sulfate. The solvent was distilled away under reduced pressure. Portions of the resulting residue were purified by reversed-phase HPLC in the same manner as in Step 2 of Example 1 to thus obtain the title compounds (A) and (B).

Step 2 Synthesis of 4-(2-methyl-1-benzofuran-7-yl)phenol

To the compound (A) (220 mg, 1.0 mmol) obtained in Step 1,4-hydroxyphenylboronic acid (172 mg, 1.3 mmol), sodium carbonate (220 mg, 2.1 mmol), Pd(PPh3)4 (catalytic amount), 1,4-dioxane (10 mL), and water (3 mL) were added, and stirred at 90° C. for 2 hours. The solvent was distilled away under reduced pressure. Ethyl acetate was used as an extraction solvent, and after washing with a 1 N hydrochloric acid aqueous solution and saturated brine, the resultant was dried over magnesium sulfate. The solvent was distilled away under reduced pressure. The resulting residue was purified by reversed-phase HPLC in the same manner as in Step 2 of Example 1 to thus obtain the title compound.

Yield: 200 mg (0.89 mmol), percentage yield: 89%
MS (ESI, m/z) 225 [M+H]$^+$
$^1$H NMR (DMSO-d$_6$, 400 MHz) δ 3.30 (s, 3H), 6.62 (s, 1H), 6.88 (d, 2H), 7.23 (dd, 1H), 7.31 (s, 1H), 7.42 (s, 1H), 7.71 (d, 2H), 9.52 (s, 1H).

Step 3 Synthesis of Compound of Example 8

To the compound (200 mg, 0.89 mmol) obtained in Step 2, DMF (10 ml), potassium carbonate (280 mg, 2.8 mmol), and methyl 3-(bromomethyl)benzoate (470 mg, 2.1 mmol) were added, and stirred at 50° C. overnight. Ethyl acetate was used as an extraction solvent, and after washing with water, a 1 N sodium hydroxide aqueous solution, and saturated brine, the resultant was dried over magnesium sulfate. The solvent was distilled away under reduced pressure. To the resulting residue, methanol (4 mL) and a 1 N sodium hydroxide aqueous solution (2 mL) were added, and stirred at room temperature for 4 hours. The solvent was distilled away under reduced pressure. Ethyl acetate was used as an extraction solvent, and after washing with a 1 N hydrochloric acid aqueous solution and saturated brine, the resultant was dried over magnesium sulfate. After the solvent was distilled away under reduced pressure, the resulting residue was washed with a water-acetonitrile mixture solvent, and then dried. Thionyl chloride (2 mL) was added to 20 mg of the resulting residue, and stirred at 40° C. for 1 hour. After that, the solvent was distilled away under reduced pressure. To the resulting residue, dichloromethane (4 mL), a 1 N sodium hydroxide aqueous solution (2 mL), and L-proline (30 mg, 0.26 mmol) were added, and stirred at room temperature overnight. The solvent was distilled away under reduced pressure. The resultant was washed with a 1 N hydrochloric acid aqueous solution and saturated brine, and then dried over magnesium sulfate. The solvent was distilled away under reduced pressure. The resulting residue was purified by reversed-phase HPLC in the same manner as in Step 2 of Example 1 to thus obtain the title compound.

Yield: 5 mg (0.010 mmol)
MS (ESI, m/z) 456 [M+H]$^+$

Example 9

1-(3-{[4-(2H-chromen-7-yl)phenoxy]methyl}benzoyl-L-proline

Step 1 Synthesis of 4-(2H-chromen-7-yl)phenol

To the compound (B) (120 mg, 0.57 mmol) obtained in Step 1 of Example 8,4-hydroxyphenylboronic acid (94 mg, 0.68 mmol), sodium carbonate (121 mg, 1.1 mmol), Pd(PPh3)4 (catalytic amount), 1,4-dioxane (10 mL), and water (3 mL) were added, and stirred at 90° C. for 2 hours. The solvent was distilled away under reduced pressure. Ethyl acetate was used as an extraction solvent, and after washing with a 1 N hydrochloric acid aqueous solution and saturated brine, the resultant was dried over magnesium sulfate. The solvent was distilled away under reduced pressure. The resulting residue was purified by reversed-phase HPLC in the same manner as in Step 2 of Example 1 to thus obtain the title compound.

Yield: 90 mg (0.40 mmol), percentage yield: 70%
MS (ESI, m/z) 225 [M+H]$^+$
$^1$H NMR (DMSO-d$_6$, 400 MHz) δ 4.72 (s, 2H), 5.91 (d, 1H), 6.58 (d, 1H), 6.77 (d, 2H), 6.92-7.23 (m, 2H), 7.23 (d, 2H), 9.42 (s, 1H).

Step 2 Synthesis of Compound of Example 9

To the compound (90 mg, 0.40 mmol) obtained in Step 1, DMF (10 ml), potassium carbonate (138 mg, 0.60 mmol), and methyl 3-(bromomethyl)benzoate (110 mg, 0.60 mmol) were added, and stirred at 50° C. overnight. Ethyl acetate was used as an extraction solvent, and after washing with water, a 1 N sodium hydroxide aqueous solution, and saturated brine, the resultant was dried over magnesium sulfate. The solvent was distilled away under reduced pressure. To the resulting residue, methanol (4 mL) and a 1 N sodium hydroxide aqueous solution (2 mL) were added, and stirred at room temperature for 4 hours. The solvent was distilled away under reduced pressure. Ethyl acetate was used as an extraction solvent, and after washing with a 1 N hydrochloric acid aqueous solution and saturated brine, the resultant was dried over magnesium sulfate. After the solvent was distilled away under reduced pressure, the resulting residue was washed with a water-acetonitrile mixture solvent, and then dried. Thionyl chloride (2 mL) was added to 10 mg of the resulting residue, and stirred at 40° C. for 1 hour. After that, the solvent was distilled away under reduced pressure. To the resulting residue, dichloromethane (4 mL), a 1 N sodium hydroxide aqueous solution (2 mL), and L-proline (30 mg, 0.26 mmol) were added, and stirred at room temperature overnight. The solvent was distilled away under reduced pressure. The resultant was washed with a 1 N hydrochloric acid aqueous solution and saturated brine, and then dried over magnesium sulfate. The solvent was distilled away under reduced pressure. The resulting residue was purified by reversed-phase HPLC in the same manner as in Step 2 of Example 1 to thus obtain the title compound.

Yield: 3 mg (0.007 mmol)
MS (ESI, m/z) 456 [M+H]$^+$

Example 10

1-(3-{[4-(4-fluoro-2,3-dihydro-1-benzofuran-7-yl)phenoxy]methyl}benzoyl-L-proline

Step 1 Synthesis of 4-(4-fluoro-2,3-dihydro-1-benzofuran-7-yl)phenol 1,4-Dioxane (12 mL) and water (4 mL) were added to 4-bromophenol (315 mg, 1.82 mmol), 4-fluorobenzofuran-7-boronic acid (360 mg, 2.00 mmol), sodium carbonate (405 mg, 3.82 mmol), and Pd(dppf)Cl2 (catalytic amount), and stirred at 100° C. for 2 hours and a half. The reaction solution was concentrated under reduced pressure. To the residue, ethyl acetate and 1N hydrochloric acid were added and stirred. After that, the insoluble material was filtered off, and extraction was performed with ethyl acetate. The organic phase was washed with a saturated aqueous sodium hydrogen carbonate solution and saturated brine, and then dried over anhydrous magnesium sulfate. The solvent was distilled away under reduced pressure. The resulting residue was purified by silica gel chromatography (hexane/ethyl acetate). To the resulting solid (352 mg, 1.54 mmol), ammonium acetate (59 mg, 0.770 mmol) was added. After dissolved in methanol (35 mL), the reaction was carried out using a continuous hydrogenation reaction apparatus (10% palladium-carbon, 50 bar, 50° C., 1 mL/minute, once). The reaction solution was concentrated under reduced pressure. The resulting residue was dissolved in ethanol (35 mL) and chloroform (1 mL), and reacted using a continuous hydrogenation reaction apparatus (10% palladium-carbon, 50 bar, 60° C., 1 mL/minute, 3 times). The reaction solution was concentrated under reduced pressure. The resulting residue was purified by reversed-phase HPLC in the same manner as in Step 2 of Example 1 to thus obtain the title compound.

Yield: 45 mg (0.195 mmol), percentage yield: 11%
$^1$H NMR (CDCl$_3$, 400 MHz) δ 3.30 (t, J=8.8 Hz, 2H), 4.67 (t, J=8.8 Hz, 2H), 6.63 (t, J=8.4 Hz, 1H), 6.84-6.91 (m, 2H), 7.18 (dd, J=8.6, 5.7 Hz, 1H), 7.48-7.55 (m, 2H).

Step 2 Synthesis of 3-{[4-(4-fluoro-2,3-dihydro-1-benzofuran-7-yl)phenoxy]methyl}benzoate methyl To 45 mg (0.195 mmol) of the compound obtained in Step 1, methyl 3-(bromomethyl)benzoate (67 mg, 0.293 mmol), potassium carbonate (54 mg, 0.390 mmol), and DMF (2 mL) was added, and stirred at room temperature for 4.5 hours. The mixture was concentrated under reduced pressure. The resulting residue was diluted with ethyl acetate, washed with 1 N hydrochloric acid, a saturated aqueous sodium hydrogen carbonate solution, and saturated brine, and then dried over anhydrous magnesium sulfate. The solvent was distilled away under reduced pressure. The resulting residue was purified by silica gel chromatography (hexane/ethyl acetate) to thus obtain the title compound.

Yield: 73.5 mg (0.194 mmol), percentage yield: quantitative
$^1$H NMR (CDCl$_3$, 400 MHz) δ 3.30 (t, J=8.8 Hz, 2H), 3.93 (s, 3H), 4.67 (t, J=8.8 Hz, 2H), 5.14 (s, 2H), 6.64 (t, J=8.4 Hz, 1H), 6.99-7.05 (m, 2H), 7.16-7.21 (m, 1H), 7.47 (t, J=7.7 Hz, 1H), 7.54-7.59 (m, 2H), 7.63-7.68 (m, 1H), 7.98-8.03 (m, 1H), 8.10-8.15 (m, 1H).

Step 3 Synthesis of 3-{[4-(4-fluoro-2,3-dihydro-1-benzofuran-7-yl)phenoxy]methyl}benzoic acid To the compound (71.1 mg, 0.188 mmol) obtained in Step 2, methanol (1 mL) and THF (1 mL) were added, and a 1 N lithium hydroxide aqueous solution (0.5 mL) was added thereto under ice-cooling. After the mixture was stirred at room temperature for 7 hours, 1 N hydrochloric acid (1 mL) was added thereto. The precipitated solid was collected by filtration and dried to thus obtain the title compound.

Yield: 61.9 mg (0.170 mmol), percentage yield: 90%
$^1$H NMR (DMSO-d$_6$, 400 MHz) δ 3.27 (t, J=8.8 Hz, 2H), 4.65 (t, J=8.8 Hz, 2H), 5.23 (s, 2H), 6.75 (t, J=8.5 Hz, 1H), 7.04-7.10 (m, 2H), 7.30 (dd, J=8.6, 5.8 Hz, 1H), 7.51-7.60 (m, 3H), 7.69-7.74 (m, 1H), 7.88-7.93 (m, 1H), 8.02-8.06 (m, 1H), 13.01 (br s, 1H).

Step 4 Synthesis of Compound of Example 10

To the compound (30.0 mg, 0.0823 mmol) of Step 3, thionyl chloride (1 mL) and DMF (catalytic amount) were added, and stirred at 50° C. for 30 minutes. The reaction solution was concentrated under reduced pressure. To the resulting residue, ethyl acetate was added to suspend the residue therein, and the suspension was concentrated under reduced pressure. The resulting residue was dissolved in dichloromethane (1 mL), and added dropwise under ice-cooling to a mixture solution of L-proline (28.4 mL, 0.247 mmol) in a dichloromethane (1 mL)-1 N sodium hydroxide aqueous solution (1 mL).

After the mixture was stirred at room temperature for 1 hour, 1 N hydrochloric acid (1 mL) was added thereto. The mixture was concentrated under reduced pressure. The resulting residue was purified by reversed-phase HPLC in the same manner as in Step 2 of Example 1 to thus obtain the title compound.

Yield: 28.6 mg (0.0620 mmol), percentage yield: 75%
MS (ESI, m/z) 462 [M+H]$^+$
$^1$H NMR (DMSO-d$_6$, 400 MHz) δ 1.75-1.97 (m, 3H), 2.19-2.34 (m, 1H), 3.27 (t, J=8.7 Hz, 2H), 3.39-3.53 (m, 2H), 4.30-4.44 (m, 1H), 4.65 (t, J=8.7 Hz, 2H), 5.11-5.25 (m, 2H), 6.75 (t, J=8.5 Hz, 1H), 7.07 (d, J=8.9 Hz, 2H), 7.26-7.52 (m, 4H), 7.54-7.62 (m, 3H).

Intermediate 2

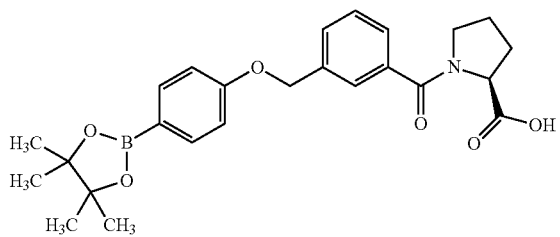

Synthesis of 1-(3-{[4-(4,4,5,5-tetramethyl-1,3,2-dioxaborolan-2-yl)phenoxy]methyl}benzoyl)-L-proline DMF (125 mL) was added to 4-(4,4,5,5-tetramethyl-1,3,2-dioxaborolan-2-yl)phenol (8.46 g, 38 mmol), methyl 3-(bromomethyl)benzoate (8.8 g, 38 mmol), and potassium carbonate (10.6 g, 77 mmol), and stirred at room temperature overnight. The resultant was diluted with ethyl acetate, washed with water and saturated brine, and then dried over anhydrous magnesium sulfate. The solvent was distilled away under reduced pressure. To the resulting residue, methanol (150 mL), water (30 mL), and lithium hydroxide (4.8 g, 114 mmol) were added, and stirred at room temperature overnight. After the solvent was distilled away under reduced pressure, the resultant was diluted with ethyl acetate, then washed with 1 N hydrochloric acid and saturated brine, and dried over anhydrous magnesium sulfate. The solvent was distilled away under reduced pressure. To the resulting residue, dichloromethane (150 mL), 1-ethyl-3-(3-dimethylaminopropyl)-carbodiimide hydrochloride (hereinafter, WSC) (7.34 g, 38.2 mmol), tert-butyl L-prolinate (7.95 g, 38.2 mmol), and triethylamine (9.65 mL, 69.4 mmol) were added, and stirred at room temperature overnight. The resultant was washed with water, 1 N hydrochloric acid, 1 N sodium hydroxide, and saturated brine, and then dried over anhydrous magnesium sulfate. The solvent was distilled away under reduced pressure, and the residue was purified by silica gel chromatography (hexane/ethyl acetate). To the resulting compound, TFA (150 mL) was added, and stirred at room temperature for 3 hours. The solvent was distilled away under reduced pressure to thus obtain the title compound.

Yield: 15.1 g (33.5 mmol), percentage yield: 88%
MS (ESI, m/z) 452 [M+H]$^+$

Intermediate 3

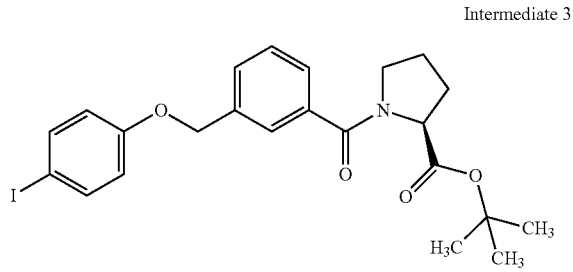 [SMILES: CC(C)(C)OC(=O)[C@@H]1CCCN1C(=O)c1cccc(COc2ccc(I)cc2)c1]

Synthesis of tert-butyl 1-{3-[(4-iodophenoxy)methyl]benzoyl}-L-prolinate

An operation similar to that in the synthesis of the intermediate 1 was performed using L-proline-tert-butyl ester in place of L-proline to thus obtain the title compound.

Yield: 8.17 g (16.1 mmol), percentage yield: 46%
MS (ESI, m/z) 508 [M+H]$^+$

Example 11

1-(3-{[4-(6-fluoro-2H-chromen-7-yl)phenoxy]methyl}benzoyl)-L-proline

DMF (10 ml), propargyl bromide (0.83 ml, 11.0 mmol), and potassium carbonate (2.87 g, 20.8 mmol) were added to 2-bromo-4-fluorophenol (1.16 mL, 10.4 mmol), and stirred at room temperature overnight. Ethyl acetate was used as an extraction solvent, and after washing with water and saturated brine, the resultant was dried over magnesium sulfate. The solvent was distilled away under reduced pressure. To the resulting residue, N,N-dimethylaniline (1 mL) was added, and stirred at 230° C. for 20 minutes. After that, cesium fluoride (165 mg, 1.09 mmol) was added thereto and stirred at 230° C. for 4 hours. The resultant was returned to room temperature, ethyl acetate was used as an extraction solvent, and a 1 N hydrochloric acid aqueous solution was added. Thereafter, the insoluble material was filtered off with celite, and the resultant was washed with saturated brine, and then dried over magnesium sulfate. The solvent was distilled away under reduced pressure. A portion of the resulting residue was purified by reversed-phase HPLC in the same manner as in Step 2 of Example 1. To the resulting compound (690 mg, 3.0 mmol), 4-hydroxyphenylboronic acid (500 mg, 3.6 mmol), sodium carbonate (640 mg, 6.0 mmol), Pd(PPh3)4 (catalytic amount), 1,4-dioxane (10 mL), and water (3 mL) were added, and stirred at 90° C. for 2 hours. The solvent was distilled away under reduced pressure. Ethyl acetate was used as an extraction solvent, and after washing with a 1N hydrochloric acid aqueous solution and saturated brine, the resultant was dried over magnesium sulfate. The solvent was distilled away under reduced pressure. To the resulting residue, DMF (10 ml), potassium carbonate (830 mg, 6.0 mmol), and methyl 3-(bromomethyl)benzoate (825 mg, 3.6 mmol) were added, and stirred at 50° C. overnight. Ethyl acetate was used as an extraction solvent, and after washing with water, a 1N sodium hydroxide aqueous solution with water, and saturated brine, the resultant was dried over magnesium sulfate. The solvent was distilled away under reduced pressure. To the resulting residue, methanol (4 mL) and a 1 N sodium hydroxide aqueous solution (2 mL) were added, and stirred at room temperature for 4 hours. The solvent was distilled away under reduced pressure. Ethyl acetate was used as an extraction solvent, and after washing with a 1 N hydrochloric acid aqueous solution and saturated brine, the resultant was dried over magnesium sulfate. After the solvent was distilled away under reduced pressure, the resulting residue was washed with a water-acetonitrile mixture solvent, and then dried. To the resulting residue, thionyl chloride (2 mL) was added, and stirred at 40° C. for 1 hour. After that, the solvent was distilled away under reduced pressure. To the resulting residue, dichloromethane (4 mL), a 1 N sodium hydroxide aqueous solution (2 mL), and L-proline (30 mg, 0.26 mmol) were added, and stirred at room temperature overnight. The solvent was distilled away under reduced pressure. The resultant was washed with a 1 N hydrochloric acid aqueous solution and saturated brine, and then dried over magnesium sulfate. The solvent was distilled away under reduced pressure. The resulting residue was purified by reversed-phase HPLC in the same manner as in Step 2 of Example 1 to thus obtain the title compound.

Yield: 10 mg (0.021 mmol)
MS (ESI, m/z) 474 [M+H]

Example 12

1-(3-{[4-(5-fluoro-1-benzofuran-7-yl)phenoxy]methyl}benzoyl)-L-proline

Step 1 Synthesis of 7-bromo-5-fluoro-1-benzofuran

Bromoacetaldehyde dimethyl acetal (1.17 mL, 10.0 mmol) and a catalytic amount of sodium iodide were added to a solution (25 mL) of 2-bromo-4-fluorophenol (0.548 mL, 5.00 mmol) and potassium carbonate (1.38 g, 10.0 mmol) in DMF, and stirred at 80° C. overnight. The solvent was distilled away under reduced pressure. The residue was diluted with ethyl acetate, washed with water and saturated brine, and then dried over anhydrous magnesium sulfate. The solvent was distilled away under reduced pressure. The resulting residue was purified by silica gel chromatography (hexane/ethyl acetate). The resulting compound (1.12 g, 4.01 mmol) was dissolved in chlorobenzene (5 mL), and added at 120° C. to a solution (5 mL) of a polyphosphoric acid (1.5 g) in chlorobenzene. After the reaction solution was stirred at 120° C. overnight, the solvent was distilled away under reduced pressure. To the residue, ethyl acetate and water were added. Under ice-cooling, this was poured into a 1 N sodium hydroxide aqueous solution, and stirred. After that, the insoluble material was filtered off, and extraction was performed with ethyl acetate. The organic phase was washed with saturated brine, and then dried over anhydrous magnesium sulfate. The solvent was distilled away under reduced pressure. The resulting residue was purified by silica gel chromatography (hexane) to thus obtain the title compound.

Yield: 215 mg (1.00 mmol), percentage yield: 20%
$^1$H NMR (CDCl$_3$, 400 MHz) δ 6.80-6.84 (m, 1H), 7.20-7.25 (m, 2H), 7.71-7.74 (m, 1H).

Step 2 Synthesis of 4-(5-fluoro-1-benzofuran-7-yl)phenol

To the compound (210 mg, 0.977 mmol) of Step 1, 4-hydroxyphenylboronic acid (162 mg, 1.17 mmol), sodium carbonate (228 mg, 2.15 mmol), and Pd(dppf)Cl2 (catalytic amount), 1,4-dioxane (1.2 mL) and water (0.4 mL) were added, and stirred at 100° C. for 2 hours. The reaction solution was concentrated under reduced pressure. To the residue, ethyl acetate and 1 N hydrochloric acid were added and stirred. After that, the insoluble material was filtered off, and extraction was performed with ethyl acetate. The organic phase was washed with saturated brine, and then dried over anhydrous magnesium sulfate. The solvent was distilled away under reduced pressure. The resulting residue was purified by silica gel chromatography (hexane/ethyl acetate) to thus obtain the title compound.

Yield: 173 mg (0.758 mmol), percentage yield: 76%
$^1$H NMR (CDCl$_3$, 400 MHz) δ 4.95 (s, 1H), 6.79 (d, J=2.2 Hz, 1H), 6.94-7.00 (m, 2H), 7.12-7.21 (m, 2H), 7.71 (d, J=2.2 Hz, 1H), 7.73-7.78 (m, 2H).

Step 3 Synthesis of 3-{[4-(5-fluoro-1-benzofuran-7-yl)phenoxy]methyl}benzoic acid To the compound (170 mg, 0.745 mmol) of Step 2, methyl 3-(bromomethyl)benzoate (256 mg, 1.12 mmol), and potassium carbonate (206 mg, 1.49 mmol), DMF (4 mL) was added, and stirred overnight. The solvent was distilled away under reduced pressure, and after diluted with ethyl acetate, the resultant was washed with the water and saturated brine, and then dried over anhydrous magnesium sulfate. The solvent was distilled away under reduced pressure. The resulting residue was purified by silica gel chromatography (hexane/ethyl acetate). To the resulting compound (267 mg, 0.709 mmol), methanol (5 mL) and THF (5 mL) were added. A 1 N lithium hydroxide aqueous solution (1.5 mL) was added thereto under ice-cooling, and stirred at room temperature overnight. After a 1N hydrochloric acid aqueous solution (2 mL) were added thereto under ice-cooling, the solid obtained by concentrating the solvent was collected by filtration to thus obtain the title compound.

Yield: 241 mg (0.665 mmol), percentage yield: 94%
$^1$H NMR (DMSO-d$_6$, 400 MHz) δ 5.29 (s, 2H), 7.03 (d, J=2.2 Hz, 1H), 7.17-7.22 (m, 2H), 7.34-7.45 (m, 2H), 7.55 (t, J=7.7 Hz, 1H), 7.74 (d, J=7.9 Hz, 1H), 7.84-7.90 (m, 2H), 7.90-7.94 (m, 1H), 8.07 (s, 1H), 8.13 (d, J=2.2 Hz, 1H), 13.05 (br s, 1H).

Step 4 Synthesis of Compound of Example 12

An operation similar to that in Step 4 of Example 10 was performed using the compound (35.1 mg, 0.0971 mmol) of Step 3 in place of 3-{[4-(4-fluoro-2,3-dihydro-1-benzofuran-7-yl) phenoxy]methyl}benzoic acid to thus obtain the title compound.

Yield: 26.8 mg (0.0583 mmol), percentage yield: 60%
MS (ESI, m/z) 460 [M+H]$^+$
$^1$H NMR (DMSO-d$_6$, 400 MHz) δ 1.74-2.36 (m, 4H), 3.40-3.63 (m, 2H), 4.32-4.45 (m, 1H), 5.16-5.32 (m, 2H), 7.03 (d, J=2.2 Hz, 1H), 7.16-7.22 (m, 2H), 7.33-7.65 (m, 6H), 7.84-7.90 (m, 2H), 8.13 (d, J=2.1 Hz, 1H).

Example 13

1-(3-{[4-(7-fluoro-1,3-benzodioxol-4-yl) phenoxy]methyl}benzoyl)-L-proline

An operation similar to that in Example 3 was performed using 4-fluoro-2,3-methylenedioxyphenylboronic acid (17.7 mg, 0.0960 mmol) in place of 4-fluorobenzofuran-7-boronic acid to thus obtain the title compound.

Yield: 22.9 mg (0.0494 mmol), percentage yield: 62%
MS (ESI, m/z) 464 [M+H]$^+$
$^1$H NMR (DMSO-d$_6$, 400 MHz) δ 1.75-2.34 (m, 4H), 3.37-3.62 (m, 2H), 4.30-4.45 (m, 1H), 5.11-5.26 (m, 2H), 6.17 (s, 2H), 6.88-6.95 (m, 1H), 7.07-7.14 (m, 3H), 7.31-7.61 (m, 4H), 7.64 (d, J=8.8 Hz, 2H).

Example 14

1-(3-{[4-(7-fluoro-1-benzofuran-5-yl)phenoxy] methyl}benzoyl)-L-proline

Step 1 Synthesis of 5-bromo-7-fluoro-1-benzofuran

An operation similar to that in Step 1 of Example 12 was performed using 4-bromo-2-fluorophenol (0.876 mL, 8.00 mmol) in place of 2-bromo-4-fluorophenol to thus obtain the title compound.

Yield: 242 mg (1.13 mmol), percentage yield: 14%

Step 2 Synthesis of 4-(7-fluoro-1-benzofuran-5-yl)phenol

An operation similar to that in Step 2 of Example 12 was performed using the compound (242 mg, 1.13 mmol) of Step 1 in place of 7-bromo-5-fluoro-1-benzofuran to thus obtain the title compound.

Yield: 239 mg (1.05 mmol), percentage yield: 93%
$^1$H NMR (CDCl$_3$, 400 MHz) δ 4.85 (s, 1H), 6.83 (dd, J=2.9, 2.1 Hz, 1H), 6.89-6.94 (m, 2H), 7.22 (dd, J=12.0, 1.4 Hz, 1H), 7.44-7.51 (m, 3H), 7.67 (d, J=2.1 Hz, 1H).

Step 3 Synthesis of 3-{[4-(7-fluoro-1-benzofuran-5-yl)phenoxy]methyl}benzoic acid An operation similar to that in Step 3 of Example 12 was performed using the compound (236 mg, 1.03 mmol) of Step 2 in place of 4-(5-fluoro-1-benzofuran-7-yl)phenol to thus obtain the title compound.

Yield: 333 mg (0.919 mmol), percentage yield: 89%
$^1$H NMR (DMSO-d$_6$, 400 MHz) δ 5.26 (s, 2H), 7.08-7.16 (m, 3H), 7.47-7.57 (m, 2H), 7.64-7.69 (m, 2H), 7.70-7.75 (m, 2H), 7.89-7.94 (m, 1H), 8.06 (s, 1H), 8.12 (d, J=2.1 Hz, 1H), 13.04 (br s, 1H).

Step 4 Synthesis of Compound of Example 14

An operation similar to that in Step 4 of Example 10 was performed using the compound (36.2 mg, 0.100 mmol) of Step 3 in place of 3-{[4-(4-fluoro-2,3-dihydro-1-benzofuran-7-yl) phenoxy]methyl}benzoic acid to thus obtain the title compound.

Yield: 21.1 mg (0.0459 mmol), percentage yield: 46%
MS (ESI, m/z) 460 [M+H]$^+$
$^1$H NMR (DMSO-d$_6$, 400 MHz) δ 1.73-2.31 (m, 5H), 3.42-3.65 (m, 2H), 4.30-4.46 (m, 1H), 5.14-5.29 (m, 2H), 7.06-7.16 (m, 3H), 7.31-7.54 (m, 4H), 7.59 (dd, J=9.1, 4.2 Hz, 2H), 7.66 (d, J=8.7 Hz, 2H), 7.72 (d, J=1.5 Hz, 1H), 8.11 (d, J=2.1 Hz, 1H), 12.59 (br s, 1H).

Example 15

1-(3-{[4-(4,5-difluoro-1-benzofuran-7-yl)phenoxy] methyl}benzoyl)-L-proline

Step 1 Synthesis of 7-bromo-4,5-difluoro-1-benzofuran

An operation similar to that in Step 1 of Example 12 was performed using 2-bromo-4,5-difluorophenol (2.51 g, 12.0 mmol) in place of 2-bromo-4-fluorophenol to thus obtain the title compound.

Yield: 572 mg (2.45 mmol), percentage yield: 20%

$^1$H NMR (CDCl$_3$, 400 MHz) δ 6.98 (d, J=2.2 Hz, 1H), 7.31-7.38 (m, 1H), 7.69 (d, J=2.2 Hz, 1H).

Step 2 Synthesis of Compound of Example 15

To the intermediate 2 (36.1 mg, 0.0800 mmol), the compound (22.4 mg, 0.0960 mmol) of Step 1, sodium carbonate (18.7 mg, 0.176 mmol), and Pd(dppf)Cl2 (catalytic amount), 1,4-dioxane (0.75 mL) and water (0.25 mL) were added, and stirred at 100° C. for 2 hours. After the insoluble material was filtered off, the resultant was purified by reversed-phase HPLC in the same manner as in Step 2 of Example 1 to thus obtain the title compound.

Yield: 21.1 mg (0.0459 mmol), percentage yield: 46%

MS (ESI, m/z) 460 [M+H]$^+$ $^1$H NMR (DMSO-d$_6$, 400 MHz) δ 1.81-2.05 (m, 3H), 2.26-2.38 (m, 1H), 3.46-3.68 (m, 2H), 4.38-4.50 (m, 2H), 5.23-5.36 (m, 2H), 7.21-7.26 (m, 2H), 7.28 (d, J=2.2 Hz, 1H), 7.38-7.70 (m, 5H), 7.85-7.91 (m, 2H), 8.24 (d, J=2.2 Hz, 1H).

Example 16

1-(3-{[4-(6,7-difluoro-1-benzofuran-5-yl)phenoxy]methyl}benzoyl)-L-proline

Step 1 Synthesis of 5-bromo-6,7-difluoro-1-benzofuran

An operation similar to that in Step 1 of Example 12 was performed using 4-bromo-2,3-difluorophenol (2.09 g, 10.0 mmol) in place of 2-bromo-4-fluorophenol to thus obtain the title compound.

Yield: 774 mg (3.32 mmol), percentage yield: 33%

$^1$H NMR (CDCl$_3$, 400 MHz) δ 6.75 (dd, J=2.8, 2.2 Hz, 1H), 7.54 (dd, J=5.7, 2.0 Hz, 1H), 7.69 (d, J=2.2 Hz, 1H).

Step 2 Synthesis of Compound of Example 16

An operation similar to that in Step 2 of Example 15 was performed using the compound (18.6 mg, 0.0800 mmol) of Step 1 in place of 7-bromo-4,5-difluoro-1-benzofuran to thus obtain the title compound.

Yield: 20.3 mg (0.0425 mmol), percentage yield: 53%

MS (ESI, m/z) 460 [M+H]$^+$ $^1$H NMR (DMSO-d$_6$, 400 MHz) δ 1.73-2.36 (m, 4H), 3.39-3.66 (m, 2H), 4.32-4.45 (m, 1H), 5.16-5.28 (m, 2H), 7.06-7.12 (m, 1H), 7.16 (d, J=8.8 Hz, 2H), 7.30-7.66 (m, 7H), 8.16 (d, J=2.1 Hz, 1H), 12.55 (br s, 1H).

Example 17

1-(3-{[4-(4,7-difluoro-1-benzofuran-5-yl)phenoxy]methyl}benzoyl)-L-proline

Step 1 Synthesis of 5-bromo-4,7-difluoro-1-benzofuran

An operation similar to that in Step 1 of Example 12 was performed using 4-bromo-2,5-difluorophenol (2.09 g, 10.0 mmol) in place of 2-bromo-4-fluorophenol to thus obtain the title compound.

Yield: 1.48 g (6.35 mmol), percentage yield: 64%

$^1$H NMR (CDCl$_3$, 400 MHz) δ 6.80 (dd, J=3.4, 1.5 Hz, 1H), 7.27-7.33 (m, 1H), 7.71 (d, J=2.1 Hz, 1H).

Step 2 Synthesis of Compound of Example 17

An operation similar to that in Step 2 of Example 15 was performed using the compound (18.6 mg, 0.0800 mmol) of Step 1 in place of 7-bromo-4,5-difluoro-1-benzofuran to thus obtain the title compound.

Yield: 24.8 mg (0.0519 mmol), percentage yield: 65%

MS (ESI, m/z) 478 [M+H]$^+$ $^1$H NMR (DMSO-d$_6$, 400 MHz) δ 1.74-2.35 (m, 4H), 3.40-3.61 (m, 2H), 4.32-4.46 (m, 1H), 5.17-5.29 (m, 2H), 7.10-7.19 (m, 2H), 7.23 (t, J=2.5 Hz, 1H), 7.31-7.65 (m, 7H), 8.19 (d, J=2.2 Hz, 1H), 12.53 (br s, 1H).

Example 18

1-(3-{[4-(5,6-difluoro-2H-chromen-7-yl)phenoxy]methyl}benzoyl)-L-proline 3-bromopropionic acid (2.0 g, 13.2 mmol), sodium hydroxide (960 mg, 23.9 mmol), and water (20 mL) were added to 2-bromo-4,5-difluorophenol (2.5 g, 11.96 mmol), and stirred at 100° C. for 1 hour. Ethyl acetate was used as an extraction solvent, and after washing with a 1N hydrochloric acid aqueous solution and saturated brine, the resultant was dried over magnesium sulfate. The solvent was distilled away under reduced pressure. To the resulting residue, 5 g of polyphosphoric acid was added, and stirred at 100° C. for 1 hour. After cooling, ethyl acetate was used as an extraction solvent, and the resultant was washed with a 1 N sodium hydroxide aqueous solution, and saturated brine, and then dried over magnesium sulfate. The solvent was distilled away under reduced pressure. Of the resulting residue, 200 mg was dissolved in methanol (20 mL), sodium borohydride (35 mg, 1.91 mmol) was added thereto, and stirred at room temperature for 1 hour. The solvent was distilled away under reduced pressure. Ethyl acetate was used as an extraction solvent, and after was washing with water and saturated brine, the resultant was dried over magnesium sulfate. The solvent was distilled away under reduced pressure. To the resulting residue, p-TsOH (catalytic amount) and toluene (20 mL) were added, and stirred at 90° C. for 2 hours. Ethyl acetate was used as an extraction solvent, and after washing with water and saturated brine, the resultant was dried over magnesium sulfate. The solvent was distilled away under reduced pressure. An operation similar to that in Example 9 was performed on the resulting compound to thus obtain the title compound.

Yield: 1.4 mg (0.029 mmol)

MS (ESI, m/z) 492 [M+H]

Example 19

1-(3-{[4-(4,5-difluoro-2,3-dihydro-1-benzofuran-7-yl)phenoxy]methyl}benzoyl)-L-proline Step 1 Synthesis of 4-(4,5-difluoro-1-benzofuran-7-yl) phenol An operation similar to that in Step 2 of Example 12 was performed using 7-bromo-4,5-difluoro-1-benzofuran (501 mg, 2.15 mmol) in place of 7-bromo-5-fluoro-1-benzofuran to thus obtain the title compound.

Yield: 568 mg (2.31 mmol), percentage yield: quantitative

Step 2 Synthesis of 4-(4,5-difluoro-2,3-dihydro-1-benzofuran-7-yl)phenol

The compound (568 mg, 2.31 mmol) of Step 1 was dissolved in acetic acid (25 mL), and a catalytic amount of 10% palladium-carbon was added thereto, and stirred in a hydrogen atmosphere of 4 atm overnight. The insoluble material was filtered off, and the solvent was distilled away under reduced pressure. The resulting residue was purified by reversed-phase HPLC in the same manner as in Step 2 of Example 1 to thus obtain the title compound.

Yield: 336 mg (1.35 mmol), percentage yield: 59%
$^1$H NMR (CDCl$_3$, 400 MHz) δ 3.32 (td, J=8.8, 0.8 Hz, 2H), 4.67 (t, J=8.8 Hz, 2H), 4.84 (br s, 1H), 6.85-6.91 (m, 2H), 7.04 (dd, J=11.8, 8.0 Hz, 1H), 7.48-7.54 (m, 2H).

Step 3 Synthesis of 3-{[4-(4,5-difluoro-2,3-dihydro-1-benzofuran-7-yl)phenoxy]methyl}benzoic acid An operation similar to that in Step 3 of Example 12 was performed using the compound (333 mg, 1.34 mmol) of Step 2 in place of 4-(5-fluoro-1-benzofuran-7-yl)phenol to thus obtain the title compound.

Yield: 500 mg (1.31 mmol), percentage yield: 98%
$^1$H NMR (DMSO-d$_6$, 400 MHz) δ 3.27-3.38 (m, 2H), 4.67 (t, J=8.7 Hz, 2H), 5.23 (s, 2H), 7.05-7.11 (m, 2H), 7.37 (dd, J=12.3, 8.2 Hz, 1H), 7.54 (t, J=7.7 Hz, 1H), 7.60-7.66 (m, 2H), 7.71 (d, J=7.7 Hz, 1H), 7.91 (d, J=7.7 Hz, 1H), 8.04 (s, 1H), 13.03 (s, 1H).

Step 4 Synthesis of Compound of Example 19

An operation similar to that in Step 4 of Example 10 was performed using the compound (95.6 mg, 0.250 mmol) of Step 3 in place of 3-{[4-(4-fluoro-2,3-dihydro-1-benzofuran-7-yl) phenoxy]methyl}benzoic acid to thus obtain the title compound.

Yield: 78.8 mg (0.164 mmol), percentage yield: 66%
MS (ESI, m/z) 480 [M+H]$^+$
$^1$H NMR (DMSO-d$_6$, 400 MHz) δ 1.75-2.33 (m, 4H), 3.33 (t, J=8.7 Hz, 2H), 3.37-3.63 (m, 2H), 4.30-4.44 (m, 1H), 4.67 (t, J=8.7 Hz, 2H), 5.11-5.25 (m, 2H), 7.04-7.12 (m, 2H), 7.29-7.69 (m, 7H), 12.62 (br s, 1H).

Example 20

1-(3-{[4-(4,6-difluoro-1-benzofuran-7-yl)phenoxy]methyl}benzoyl)-L-proline

Step 1 Synthesis of 7-bromo-4,6-difluoro-1-benzofuran

An operation similar to that in Step 1 of Example 12 was performed using 2-bromo-3,5-difluorophenol (915 mg, 4.38 mmol) in place of 2-bromo-4-fluorophenol to thus obtain the title compound.

Yield: 716 mg (3.07 mmol), percentage yield: 70%
$^1$H NMR (CDCl$_3$, 400 MHz) δ 6.87 (t, J=9.2 Hz, 1H), 6.92 (d, J=2.2 Hz, 1H), 7.67 (d, J=2.2 Hz, 1H).

Step 2 Synthesis of Compound of Example 20

An operation similar to that in Step 2 of Example 15 was performed using the compound (18.6 mg, 0.0800 mmol) of Step 1 in place of 7-bromo-4,5-difluoro-1-benzofuran to thus obtain the title compound.

Yield: 13.0 mg (0.0272 mmol), percentage yield: 34%
MS (ESI, m/z) 478 [M+H]$^+$
$^1$H NMR (DMSO-d$_6$, 400 MHz) δ 1.74-2.33 (m, 4H), 3.40-3.60 (m, 2H), 4.29-4.44 (m, 1H), 5.23 (d, J=27.8 Hz, 2H), 7.14 (d, J=2.2 Hz, 1H), 7.16-7.21 (m, 2H), 7.27-7.64 (m, 7H), 8.10 (d, J=2.2 Hz, 1H), 12.55 (br s, 1H).

Example 21

1-(3-{[4-(4,5-difluoro-3-methyl-1-benzofuran-7-yl)phenoxy]methyl}benzoyl)-L-proline Step 1 Synthesis of 7-bromo-4,5-difluoro-3-methyl-1-benzofuran An operation similar to that in Step 1 of Example 12 was performed using 2-bromo-4,5-difluorophenol (1.05 g, 5.00 mmol) in place of 2-bromo-4-fluorophenol, and bromoacetone (0.504 mL, 6.00 mmol) in place of bromoacetaldehyde dimethyl acetal to thus obtain the title compound.

Yield: 150 mg (0.607 mmol), percentage yield: 12%
$^1$H NMR (CDCl$_3$, 400 MHz) δ 2.35 (d, J=0.9 Hz, 3H), 7.27-7.32 (m, 1H), 7.43-7.40 (m, 1H).

Step 2 Synthesis of Compound of Example 21

An operation similar to that in Step 2 of Example 15 was performed using the compound (24.7 mg, 0.100 mmol) of Step 1 in place of 7-bromo-4,5-difluoro-1-benzofuran to thus obtain the title compound.

Yield: 31.2 mg (0.0635 mmol), percentage yield: 64%
MS (ESI, m/z) 492 [M+H]$^+$
$^1$H NMR (DMSO-d$_6$, 400 MHz) δ 1.74-2.01 (m, 3H), 2.20-2.31 (m, 1H), 2.34 (s, 3H), 3.44-3.62 (m, 2H), 4.31-4.44 (m, 1H), 5.15-5.28 (m, 2H), 7.13-7.21 (m, 2H), 7.30-7.64 (m, 5H), 7.76-7.83 (m, 2H), 7.91 (s, 1H), 12.52 (br s, 1H).

Example 22

1-(3-{[4-(5-fluoro-2,2-dimethyl-2,3-dihydro-1-benzofuran-7-yl)phenoxy]methyl}benzoyl)-L-proline Step 1 Synthesis of 2-bromo-4-fluoro-1-[(2-methylprop-2-en-1-yl)oxy]benzene Potassium carbonate (829 mg, 6.00 mmol) and 3-chloro-2-methyl-1-propene (0.591 mL, 6.00 mmol) were added to a solution (25 mL) of 2-bromo-4-fluorophenol (955 mg, 5.00 mmol) in DMF, and stirred at 60° C. overnight. The solvent was distilled away under reduced pressure, and after diluted with ethyl acetate, the resultant was washed with water and saturated brine, and then dried over anhydrous magnesium sulfate. The solvent was distilled away, and the resulting residue was purified by silica gel chromatography (hexane/ethyl acetate) to thus obtain the title compound.

Yield: 1.17 g (4.76 mmol), percentage yield: 95%
$^1$H NMR (CDCl$_3$, 400 MHz) δ 1.81-1.91 (m, 3H), 4.46 (s, 2H), 4.96-5.05 (m, 1H), 5.11-5.18 (m, 1H), 6.83 (dd, J=9.1, 4.8 Hz, 1H), 6.92-6.99 (m, 1H), 7.28-7.33 (m, 1H).

Step 2 Synthesis of 7-bromo-5-fluoro-2,2-dimethyl-2,3-dihydro-1-benzofuran

A solution (1 mL) of the compound (560 mg, 2.28 mmol) of Step 1 in N-methyl-2-pyrrolidinone was irradiated with a microwave in a tightly-sealed container, and stirred at 200° C. for 1 hour. To the reaction solution, ethyl acetate and hexane were added. After washing with water and saturated brine, the resultant was dried over anhydrous magnesium sulfate. The solvent was distilled away under reduced pressure. The residue was purified by silica gel chromatography. To the resulting compound (368 mg, 1.50 mmol), formic acid (2 mL) and water (0.2 mL) were added, and stirred at 100° C. overnight. The reaction solution was diluted with ethyl acetate, and after washed with water and saturated brine, the resultant was dried over anhydrous magnesium sulfate. The solvent was distilled away under reduced pressure. The resulting residue was purified by silica gel chromatography (hexane/ethyl acetate) to thus obtain the title compound.

Yield: 315 mg (1.29 mmol), percentage yield: 57%
$^1$H NMR (CDCl$_3$, 400 MHz) δ 1.51 (s, 6H), 3.08 (d, J=0.9 Hz, 2H), 6.78-6.83 (m, 1H), 6.98-7.03 (m, 1H).

Step 3 Synthesis of Compound of Example 22

An operation similar to that in Step 2 of Example 15 was performed using the compound (24.5 mg, 0.100 mmol) of Step 2 in place of 7-bromo-4,5-difluoro-1-benzofuran to thus obtain the title compound.

Yield: 40.6 mg (0.0829 mmol), percentage yield: 83%
MS (ESI, m/z) 492 [M+H]$^+$
$^1$H NMR (DMSO-d$_6$, 400 MHz) δ 1.43 (s, 6H), 1.72-2.02 (m, 3H), 2.17-2.35 (m, 1H), 3.04 (s, 2H), 3.41-3.63 (m, 2H), 4.31-4.45 (m, 1H), 5.10-5.28 (m, 2H), 6.96-7.01 (m, 1H), 7.05-7.11 (m, 3H), 7.31-7.62 (m, 4H), 7.63-7.70 (m, 2H), 12.55 (br s, 1H).

Example 23

1-(3-{[4-(4,5-difluoro-2-methyl-1-benzofuran-7-yl)phenoxy]methyl}benzoyl)-L-proline Step 1 Synthesis of 7-bromo-4,5-difluoro-2-methyl-1-benzofuran Potassium carbonate (1.38 g, 10.0 mmol) and propargyl bromide (0.414 mL, 5.50 mmol) were added to a solution (25 mL) of 2-bromo-4,5-difluorophenol (1.05 g, 5.00 mmol) in DMF, and stirred at room temperature overnight. The solvent was distilled away under reduced pressure, and after diluted with ethyl acetate, the resultant was washed with water and saturated brine, and dried over anhydrous magnesium sulfate. The solvent was distilled away, and the residue was purified by silica gel chromatography (hexane/ethyl acetate). To the resulting compound (1.18 g, 4.78 mmol), cesium fluoride (872 mg, 5.74 mmol) and dimethylaniline (7 mL) were added, and stirred at 170° C. overnight. To the reaction solution, ethyl acetate and a 2 N hydrochloric acid aqueous solution were added and stirred. After the insoluble material was filtered off, extraction was performed with ethyl acetate. The organic phase was washed with a saturated aqueous sodium hydrogen carbonate solution and saturated brine, and then dried over anhydrous magnesium sulfate. The solvent was distilled away under reduced pressure. The resulting residue was purified by silica gel chromatography (hexane) to thus obtain the title compound.

Yield: 164 mg (0.664 mmol), percentage yield: 14%
$^1$H NMR (CDCl$_3$, 400 MHz) δ 2.50 (d, J=1.0 Hz, 3H), 6.57 (q, J=1.0 Hz, 1H), 7.22 (dd, J=10.2, 6.9 Hz, 1H).

Step 2 Synthesis of Compound of Example 23

An operation similar to that in Step 2 of Example 15 was performed using the compound (26.8 mg, 0.108 mmol) of Step 1 in place of 7-bromo-4,5-difluoro-1-benzofuran to thus obtain the title compound.

Yield: 42.9 mg (0.0873 mmol), percentage yield: 81%
MS (ESI, m/z) 492 [M+H]$^+$

1H NMR (DMSO-d6, 400 MHz) δ 1.74-2.33 (m, 4H), 2.49 (s, 3H), 3.53-3.64 (m, 2H), 4.31-4.45 (m, 1H), 5.15-5.31 (m, 2H), 6.84 (d, J=1.1 Hz, 1H), 7.15-7.20 (m, 2H), 7.32-7.64 (m, 5H), 7.78-7.83 (m, 2H), 12.60 (br s, 1H).

Example 24

1-(3-{[4-(2,3-dihydro-1H-inden-4-yl)phenoxy]methyl}benzoyl)-L-proline

7-Bromo-1H-indene (250 mg, 1.28 mmol), 4-hydroxyphenylboronic acid (212 mg, 1.54 mmol), sodium carbonate (270 mg, 2.56 mmol), Pd(PPh3)4 (catalytic amount), 1,4-dioxane (10 mL), and water (3 mL) were added, and stirred at 90° C. for 8 hours. The solvent was distilled away under reduced pressure. Ethyl acetate was used as an extraction solvent, and after washing with a 1 N hydrochloric acid aqueous solution and saturated brine, the resultant was dried over magnesium sulfate. The solvent was distilled away under reduced pressure. To half of the resulting residue, methanol (10 mL) and a catalytic amount of 10% palladium-carbon were added, and stirred in a hydrogen atmosphere at room temperature overnight. The insoluble material was filtered off, and the solvent was distilled away under reduced pressure. An operation similar to that in Step 2 of Example 9 was performed on the resulting residue to thus obtain the title compound.

Yield: 3.1 mg (0.007 mmol)
MS (ESI, m/z) 442 [M+H]$^+$

Example 25

1-(3-{[4-(7-fluoro-1-benzofuran-4-yl)phenoxy]methyl}benzoyl)-L-proline

Step 1 Synthesis of 4-bromo-7-fluoro-1-benzofuran

An operation similar to that in Step 1 of Example 12 was performed using 5-bromo-2-fluorophenol (0.561 mL, 5.00 mmol) in place of 2-bromo-4-fluorophenol to thus obtain the title compound.

Yield: 191 mg (0.888 mmol), percentage yield: 18%
$^1$H NMR (CDCl$_3$, 400 MHz) δ 6.85 (dd, J=2.7, 2.2 Hz, 1H), 6.95 (dd, J=10.2, 8.6 Hz, 1H), 7.31 (dd, J=8.6, 3.7 Hz, 1H), 7.70 (d, J=2.2 Hz, 1H).

Step 2 Synthesis of 4-(7-fluoro-1-benzofuran-4-yl)phenol

An operation similar to that in Step 2 of Example 12 was performed using the compound (182 mg, 0.846 mmol) of Step 1 in place of 7-bromo-5-fluoro-1-benzofuran to thus obtain the title compound.

Yield: 160 mg (0.701 mmol), percentage yield: 83%
$^1$H NMR (CDCl$_3$, 400 MHz) δ 4.91 (s, 1H), 6.92-6.97 (m, 3H), 7.08 (dd, J=10.4, 8.3 Hz, 1H), 7.17 (dd, J=8.3, 4.2 Hz, 1H), 7.43-7.48 (m, 2H), 7.69 (d, J=2.2 Hz, 1H).

Step 3 Synthesis of 3-{[4-(7-fluoro-1-benzofuran-4-yl)phenoxy]methyl}benzoic acid An operation similar to that in Step 3 of Example 12 was performed using the compound (157 mg, 0.688 mmol) of Step 2 in place of 4-(5-fluoro-1-benzofuran-7-yl)phenol to thus obtain the title compound.

Yield: 223 mg (0.615 mmol), percentage yield: 89%
$^1$H NMR (DMSO-d$_6$, 400 MHz) δ 5.27 (s, 2H), 7.12 (dd, J=3.1, 2.2 Hz, 1H), 7.15-7.20 (m, 2H), 7.27-7.32 (m, 2H), 7.53-7.60 (m, 3H), 7.72-7.77 (m, 1H), 7.90-7.94 (m, 1H), 8.07 (s, 1H), 8.17 (d, J=2.2 Hz, 1H), 13.05 (br s, 1H).

Step 4 Synthesis of Compound of Example 25

An operation similar to that in Step 4 of Example 10 was performed using the compound (35.2 mg, 0.0971 mmol) of Step 3 in place of 3-{[4-(4-fluoro-2,3-dihydro-1-benzofuran-7-yl) phenoxy]methyl}benzoic acid to thus obtain the title compound.
Yield: 2.3 mg (0.00501 mmol), percentage yield: 5.2%
MS (ESI, m/z) 460 [M+H]$^+$ Example 26

1-(3-{[4-(1H-indol-4-yl)phenoxy]methyl}benzoyl)-L-proline

An operation similar to that in Example 3 was performed using indole-4-boronic acid pinacol ester (23.3 mg, 0.0960 mmol) in place of 4-fluorobenzofuran-7-boronic acid to thus obtain the title compound.
Yield: 16.8 mg (0.0381 mmol), percentage yield: 48%
MS (ESI, m/z) 441 [M+H]$^+$
$^1$H NMR (DMSO-d$_6$, 400 MHz) δ 1.75-2.02 (m, 3H), 2.19-2.35 (m, 1H), 3.40-3.64 (m, 2H), 4.32-4.45 (m, 1H), 5.14-5.30 (m, 2H), 6.52 (s, 1H), 7.03 (d, J=7.2 Hz, 1H), 7.11-7.19 (m, 3H), 7.31-7.65 (m, 8H), 11.21 (s, 1H), 12.57 (br s, 1H).

Example 27

1-(3-{[4-(8-fluoro-2H-chromen-5-yl)phenoxy]methyl}benzoyl)-L-proline

A similar operation to that in Example 18 was performed using 2-fluoro-5-bromophenol (3.13 g, 16.39 mmol) in place of 2-bromo-4,5-difluorophenol (2.5 g, 11.96 mmol) to thus obtain the title compound.
Yield: 3.4 mg (0.007 mmol)
MS (ESI, m/z) 474 [M+H]$^+$ Example 28

1-(3-{[4-(1-benzothien-7-yl)phenoxy]methyl}benzoyl)-L-proline

An operation similar to that in Example 3 was performed using 1-benzothien-7-ylboronic acid (17.1 mg, 0.0960 mmol) in place of 4-fluorobenzofuran-7-boronic acid to thus obtain the title compound.
Yield: 12.8 mg (0.0280 mmol), percentage yield: 35%
MS (ESI, m/z) 458 [M+H]$^+$
$^1$H NMR (DMSO-d$_6$, 400 MHz) δ1.76-2.35 (m, 4H), 3.41-3.63 (m, 2H), 4.33-4.45 (m, 1H), 5.18-5.31 (m, 2H), 7.16-7.23 (m, 2H), 7.33-7.70 (m, 9H), 7.79 (d, J=5.5 Hz, 1H), 7.86 (dd, J=7.9, 0.9 Hz, 1H), 12.66 (br s, 1H).

Example 29

1-(3-{[4-(7-fluoro-1H-indol-4-yl)phenoxy]methyl}benzoyl)-L-proline

An operation similar to that in Step 2 of Example 15 was performed using 4-bromo-7-fluoro-1H-indole (26.7 mg, 0.125 mmol) in place of 7-bromo-4,5-difluoro-1-benzofuran to thus obtain the title compound.

Yield: 7.0 mg (0.0153 mmol), percentage yield: 12%
MS (ESI, m/z) 492 [M+H]$^+$
$^1$H NMR (DMSO-d$_6$, 400 MHz) δ 1.74-2.37 (m, 4H), 3.42-3.63 (m, 2H), 4.32-4.45 (m, 1H), 5.14-5.28 (m, 2H), 6.55-6.63 (m, 1H), 6.94-7.01 (m, 2H), 7.14 (d, J=8.7 Hz, 2H), 7.31-7.65 (m, 7H), 11.72 (s, 1H), 12.59 (br s, 1H).

Example 30

1-(3-{[4-(6,7-difluoro-1-benzofuran-4-yl)phenoxy]methyl}benzoyl)-L-proline

Step 1 Synthesis of 4-bromo-6,7-difluoro-1-benzofuran

An operation similar to that in Step 1 of Example 12 was performed using 5-bromo-2,3-difluorophenol (2.09 g, 10.0=01) in place of 2-bromo-4-fluorophenol to thus obtain the title compound.
Yield: 1.48 g (6.35 mmol), percentage yield: 64%
$^1$H NMR (CDCl$_3$, 400 MHz) δ 6.80 (dd, J=3.4, 1.5 Hz, 1H), 7.27-7.33 (m, 1H), 7.71 (d, J=2.1 Hz, 1H).

Step 2 Synthesis of Compound of Example 30

An operation similar to that in Step 2 of Example 15 was performed using the compound (18.6 mg, 0.0800 mmol) of Step 1 in place of 7-bromo-4,5-difluoro-1-benzofuran to thus obtain the title compound.
Yield: 17.9 mg (0.0375 mmol), percentage yield: 47%
MS (ESI, m/z) 478 [M+H]$^+$
$^1$H NMR (DMSO-d$_6$, 400 MHz) δ 1.74-2.36 (m, 4H), 3.39-3.65 (m, 2H), 4.31-4.44 (m, 1H), 5.17-5.30 (m, 2H), 7.12-7.21 (m, 3H), 7.32-7.64 (m, 7H), 8.21 (d, J=2.2 Hz, 1H), 12.60 (br s, 1H).

Example 31

1-(3-{[4-(7,8-difluoro-2H-chromen-5-yl)phenoxy]methyl}benzoyl)-L-proline

A similar operation to that in Example 18 was performed using 2,3-difluoro-5-bromophenol (2.65 g, 12.68 mmol) in place of 2-bromo-4,5-difluorophenol (2.5 g, 11.96 mmol) to thus obtain the title compound.
Yield: 2.7 mg (0.005 mmol)
MS (ESI, m/z) 492 [M+H]$^+$ Example 32

1-(3-{[4-(3-oxo-3,4-dihydro-2H-1,4-benzoxazin-8-yl)phenoxy]methyl}benzoyl)-L-proline Step 1 8-bromo-4H-benzoxazin-3-one 2-Amino-6-bromophenol (1.0 g, 5.32 mmol) was dissolved in DMF (20 mL), and potassium carbonate (1.6 g, 11.7 mmol) and chloroacetyl chloride (0.466 mL, 5.85 mmol) were added thereto, and stirred at room temperature overnight. After diluted with ethyl acetate, the resultant was washed with water and saturated brine, and dried over anhydrous magnesium sulfate. The solvent was distilled away, and the residue washed with an ethyl acetate-hexane mixture solvent to thus obtain the title compound.
Yield: 1.1 mg (4.85 mmol), percentage yield: 91%
MS (ESI, m/z) 228 [M+H]$^+$ Step 2 Synthesis of Example 32

An operation similar to that in Step 2 of Example 15 was performed using the compound (18 mg, 0.079 mmol) of Step 1 in place of 7-bromo-4,5-difluoro-1-benzofuran to thus obtain the title compound.
Yield: 4 mg (0.008 mmol), percentage yield: 10%
MS (ESI, m/z) 473 [M+H]$^+$ Example 33

1-(3-{[4-(6,7-difluoro-1H-indol-4-yl)phenoxy]methyl}benzoyl)-L-proline

Step 1 Synthesis of 4-bromo-6,7-difluoro-1H-indole

A solution (20 mL) of 5-Bromo-1,2-difluoro-3-nitrobenzene (1.19 g, 5.00 mmol) in THF was cooled to −50° C. To this, a 1 M vinylmagnesium bromide/THF solution (15 mL) was added dropwise. After the mixture was stirred at −40° C. for 4 hours, a saturated aqueous ammonium chloride solution was added thereto, and concentrated under reduced pressure. The reaction solution was diluted with ethyl acetate, and after washed with saturated brine, the resultant was dried over anhydrous magnesium sulfate. The resultant was concentrated under reduced pressure. The resulting residue was purified by silica gel chromatography (hexane) to thus obtain the title compound.
Yield: 145 mg (0.625 mmol), percentage yield: 12%
$^1$H NMR (CDCl$_3$, 400 MHz) δ 6.58 (td, J=3.2, 2.4 Hz, 1H), 7.17 (dd, J=10.4, 6.3 Hz, 1H), 7.28 (dd, J=3.2, 2.4 Hz, 1H), 8.50 (br s, 1H).

Step 2 Synthesis of Compound of Example 33

An operation similar to that in Step 2 of Example 15 was performed using the compound (28.2 mg, 0.121 mmol) of Step 1 in place of 7-bromo-4,5-difluoro-1-benzofuran to thus obtain the title compound.
Yield: 37.0 mg (0.0777 mmol), percentage yield: 64%
MS (ESI, m/z) 477 [M+H]+
$^1$H NMR (DMSO-d$_6$, 400 MHz) δ 1.76-2.32 (m, 4H), 3.40-3.52 (m, 2H), 4.32-4.45 (m, 1H), 5.16-5.29 (m, 2H), 6.54-6.62 (m, 1H), 7.06 (dd, J=12.3, 6.8 Hz, 1H), 7.12-7.19 (m, 2H), 7.31-7.68 (m, 7H), 11.90 (s, 1H), 12.64 (br s, 1H).

Example 34

1-[3-({[4',5'-difluoro-2'-(prop-2-yn-1-yloxy) biphenyl-4-yl]oxy}methyl)benzoyl]-L-proline Step 1 tert-butyl 1-(3-{[(4',5'-difluoro-2'-hydroxybiphenyl-4-yl)oxy]methyl}benzoyl)-L-prolinate To the intermediate 3 (1.6 g, 3.16 mmol), 2-hydroxy-4,5-difluorophenylboronic acid (576 mg, 3.31 mmol), sodium carbonate (680 mg, 2.15 mmol), and Pd(PPh3)4 (catalytic amount), 1,4-dioxane (24 mL) and water (8 mL) were added, and stirred at 100° C. for 2 hours. The reaction solution was concentrated under reduced pressure. To the residue, ethyl acetate and 1 N hydrochloric acid were added and stirred. After that, the insoluble material was filtered off, and extraction was performed with ethyl acetate. The organic phase was washed with saturated brine, and then dried over anhydrous magnesium sulfate. The solvent was distilled away under reduced pressure. The resulting residue was purified by reversed-phase HPLC in the same manner as in Step 2 of Example 1 to thus obtain the title compound.
Yield: 1.2 g (2.35 mmol), percentage yield: 74%
MS (ESI, m/z) 510 [M+H]$^+$ Step 2 Synthesis of Example 34

The compound (30 mg, 0.059 mmol) obtained in Step 1 was dissolved in DMF (2 mL), and potassium carbonate (12 mg, 0.088 mmol) and propargyl bromide (0.007 mL, 0.088 mmol) were added thereto, and stirred at room temperature overnight. After diluted with ethyl acetate, the resultant was washed with water and saturated brine, and dried over anhydrous magnesium sulfate. The solvent was distilled away, and to the residue, TFA (2 mL) was added, and stirred for 2 hours. The solvent was distilled away, and the resulting residue was purified by reversed-phase HPLC in the same manner as in Step 2 of Example 1 to thus obtain the title compound.
Yield: 5.3 mg (0.011 mmol), percentage yield: 19%
MS (ESI, m/z) 492 [M+H]$^+$ Example 35

1-[3-({[2'-(cyanomethoxy)-4',5'-difluorobiphenyl-4-yl]oxy}methyl)benzoyl]-L-proline A similar operation to that in Step 2 of Example 34 was performed using bromoacetonitrile (0.006 mL, 0.088 mmol) in place of propargyl bromide to thus obtain the title compound.
Yield: 2.0 mg (0.004 mmol), percentage yield: 7%
MS (ESI, m/z) 493 [M+H]$^+$ Example 36

1-[3-({[2'-(allyloxy)-4',5'-difluorobiphenyl-4-yl]oxy}methyl)benzoyl]-L-proline

A similar operation to that in Step 2 of Example 34 was performed using allyl bromide (0.006 mL, 0.088 mmol) in place of propargyl bromide to thus obtain the title compound.
Yield: 6.2 mg (0.013 mmol), percentage yield: 17%
MS (ESI, m/z) 494 [M+H]$^+$ Example 37

1-(3-{[(4',5'-difluoro-2'-d$_3$ methoxybiphenyl-4-yl)oxy]methyl}benzoyl)-L-proline A similar operation to that in Step 2 of Example 34 was performed using iodomethane-d3 (0.003 mL, 0.088 mmol) in place of propargyl bromide to thus obtain the title compound.
Yield: 5.3 mg (0.011 mmol), percentage yield: 15%
MS (ESI, m/z) 471 [M+H]$^+$ Example 38

1-[3-({[4',5'-difluoro-2'-(methylthio)biphenyl-4-yl]oxy}methyl)benzoyl]-L-proline Step 1 Synthesis of 1-bromo-4,5-difluoro-2-(methylthio)benzene Potassium carbonate (310 mg, 2.22 mmol) and iodomethane (0.138 mL, 2.22 mmol) were added to a solution (10 mL) of 2-bromo-4,5-difluorothiophenol (400 mg, 1.78 mmol) in DMF, and stirred at room temperature overnight. After diluted with ethyl acetate, the resultant was washed with water and saturated brine, and then dried over anhydrous magnesium sulfate. The solvent was distilled away, and the resulting residue was purified by silica gel chromatography (hexane/ethyl acetate) to thus obtain the title compound.

Yield: 404 mg (1.69 mmol), percentage yield: 95%
$^1$H NMR (CDCl$_3$, 400 MHz) δ 2.46 (s, 3H), 6.97 (dd, J=10.9, 7.6 Hz, 1H), 7.39 (dd, J=9.5, 7.6 Hz, 1H).

Step 2 Synthesis of Compound of Example 38

An operation similar to that in Step 2 of Example 15 was performed using the compound (180 mg, 0.753 mmol) of Step 1 in place of 7-bromo-4,5-difluoro-1-benzofuran to thus obtain the title compound.

Yield: 112 mg (0.232 mmol), percentage yield: 31%
MS (ESI, m/z) 484 [M+H]$^+$
$^1$H NMR (DMSO-d$_6$, 400 MHz) δ 1.75-2.01 (m, 3H), 2.19-2.35 (m, 1H), 2.39 (s, 3H), 3.41-3.62 (m, 2H), 4.31-4.44 (m, 1H), 5.13-5.26 (m, 2H), 7.05-7.11 (m, 2H), 7.25-7.63 (m, 8H), 12.55 (br s, 1H).

Example 39

1-(3-{[4-(4,5-difluoro-1-benzothien-7-yl)phenoxy]methyl}benzoyl)-L-proline

Step 1 Synthesis of
7-bromo-4,5-difluoro-1-benzothiophene

An operation similar to that in Step 1 of Example 12 was performed using 2-bromo-4,5-difluorothiophenol (1.31 g, 5.83 mmol) in place of 2-bromo-4-fluorophenol to thus obtain the title compound.

Yield: 1.0 g (4.0 mmol), percentage yield: 69%
$^1$H NMR (CDCl$_3$, 400 MHz) δ 7.40 (ddd, J=9.6, 6.4, 0.5 Hz, 1H), 7.60-7.54 (m, 2H).

Step 2 Synthesis of Compound of Example 39

To the intermediate 2 (110 mg, 0.243 mmol), the compound (50.4 mg, 0.202 mmol) of Step 1, sodium carbonate (47.1 mg, 0.444 mmol), and Pd(dppf)Cl2 (catalytic amount), 1,4-dioxane (0.75 mL) and water (0.25 mL) were added, and stirred at 100° C. for 2 hours. Further, the intermediate 2 (50.0 mg, 0.111 mmol) and Pd(dppf)Cl2 (14.8 mg, 0.0202 mmol) were added thereto. The mixture was irradiated with a microwave in a tightly-sealed container, and stirred at 130° C. for 30 minutes. After the insoluble material was filtered off, the resultant was purified by reversed-phase HPLC in the same manner as in Step 2 of Example 1 to thus obtain the title compound.

Yield: 30.2 mg (0.0612 mmol), percentage yield: 30%
MS (ESI, m/z) 460 [M+H]$^+$
$^1$H NMR (DMSO-d$_6$, 400 MHz) δ 1.76-2.02 (m, 3H), 2.21-2.36 (m, 1H), 3.53-3.67 (m, 2H), 4.33-4.45 (m, 1H), 5.18-5.32 (m, 2H), 7.17-7.24 (m, 2H), 7.33-7.70 (m, 8H), 8.00 (d, J=5.6 Hz, 1H), 12.51 (s, 1H).

Example 40

1-(3-{[(4',5'-difluoro-2'mercaptobiphenyl-4-yl)oxy]methyl}benzoyl)-L-proline

2-Bromo-4,5-difluorothiophenol (280 mg, 1.24 mmol) was dissolved in dichloromethane (10 mL), and 2,4,6-trimethoxybenzyl alcohol (246 mg, 1.24 mmol) and trifluoroacetic acid (0.125 mL, 1.61 mmol) were added thereto, and stirred at room temperature for 1 hour. A saturated aqueous sodium hydrogen carbonate solution was added thereto. After diluted with ethyl acetate, the resultant was washed with water and saturated brine, and dried over anhydrous magnesium sulfate. The solvent was distilled away, and the residue was purified by silica gel chromatography (hexane/ethyl acetate). To the resulting compound (140 mg, 0.35 mmol), the intermediate 2 (180 mg, 0.39 mmol), sodium carbonate (200 mg, 1.89 mmol), Pd(dppf)Cl2 (catalytic amount), 1,4-dioxane (0.75 mL), and water (0.25 mL) were added, and stirred at 100° C. for 2 hours. After the insoluble material was filtered off, the resultant was purified by reversed-phase HPLC in the same manner as in Step 2 of Example 1. To the resulting residue, trifluoroacetic acid (0.8 mL), triethylsilane (0.3 mL), and dichloromethane (8 mL) were added, and stirred at room temperature for 1 hour. The resultant was purified by reversed-phase HPLC in the same manner as in Step 2 of Example 1 to thus obtain the title compound.

Yield: 20 mg (0.043 mmol), percentage yield: 3.4%
MS (ESI, m/z) 470 [M+H]$^+$

Example 41

1-(3-{[4-(6,7-difluoro-2-methyl-1H-indol-4-yl) phenoxy]methyl}benzoyl)-L-proline Step 1 Synthesis of
4-bromo-6,7-difluoro-2-methyl-1H-indole An operation similar to that in Step 1 of Example 33 was performed using a 0.5 M isopropenylmagnesium bromide/THF solution (30 mL) in place of a 1 M vinylmagnesium bromide/THF solution to thus obtain the title compound.

Yield: 400 mg (1.63 mmol), percentage yield: 33%
$^1$H NMR (CDCl$_3$, 400 MHz) δ 2.46 (s, 3H), 6.22-6.26 (m, 1H), 7.10 (dd, J=10.5, 6.3 Hz, 1H), 8.20 (br s, 1H).

Step 2 Synthesis of Compound of Example 41

An operation similar to that in Step 2 of Example 15 was performed using the compound (61.3 mg, 0.249 mmol) of Step 1 in place of 7-bromo-4,5-difluoro-1-benzofuran to thus obtain the title compound.

Yield: 50.1 mg (0.102 mmol), percentage yield: 41%
MS (ESI, m/z) 491 [M+H]$^+$
$^1$H NMR (DMSO-d$_6$, 400 MHz) δ 1.76-2.32 (m, 4H), 2.38 (s, 3H), 3.42-3.63 (m, 2H), 4.31-4.44 (m, 1H), 5.16-5.28 (m, 2H), 6.29 (s, 1H), 6.99 (dd, J=12.4, 6.9 Hz, 1H), 7.09-7.17 (m, 2H), 7.31-7.64 (m, 6H), 11.66 (s, 1H), 12.55 (br s, 1H).

Example 42

1-{3-[({3'-[(cyanomethyl)amino]-4',5'-difluorobiphenyl-4-yl}oxy)methyl]benzoyl}-L-proline trifluoroacetic acid salt Step 1 Synthesis of tert-butyl(5-bromo-2,3-difluorophenyl)(cyanomethyl)carbamate A solution (3 mL) of tert-butyl(5-bromo-2,3-difluorophenyl)carbamate (182 mg, 0.591 mmol) in DMF was added to a suspension of 60% sodium hydride-oil dispersion (31.2 mg) in DMF, and stirred at room temperature for 15 minutes. To the reaction solution, bromoacetonitrile (0.041 mL, 0.591 mmol) was added, and stirred at room temperature for 4 hours. After quenched with a saturated aqueous ammonium chloride solution under ice-cooling, extraction was performed with ethyl acetate. The resulting organic phase was dried over anhydrous magnesium sulfate. The solvent was distilled away under reduced pressure. The resulting residue was purified by silica gel chromatography (hexane/ethyl acetate) to thus obtain the title compound.

Yield: 142 mg (0.409 mmol), percentage yield: 69%
MS (ESI, m/z) 348 [M+H]$^+$
$^1$H NMR (CDCl$_3$, 400 MHz) δ 1.45 (br s, 9H), 4.46 (br s, 2H), 7.28-7.33 (m, 1H), 7.33-7.39 (m, 1H).

Step 2 Synthesis of 1-{3-[({3'-[(tert-butoxycarbonyl)(cyanomethyl)amino]-4',5'-difluorobiphenyl-4-yl}oxy)methyl]benzoyl}-L-proline An operation similar to that in Step 2 of Example 15 was performed using the compound (95.5 mg, 0.275 mmol) of Step 1 in place of 7-bromo-4,5-difluoro-1-benzofuran to thus obtain the title compound.

Yield: 109 mg (0.184 mmol), percentage yield: 67%
MS (ESI, m/z) 592 [M+H]$^+$
$^1$H NMR (DMSO-d$_6$, 400 MHz) δ 1.40 (s, 9H), 1.75-2.32 (m, 4H), 3.41-3.62 (m, 2H), 4.31-4.45 (m, 1H), 4.69-4.83 (m, 2H), 5.15-5.30 (m, 2H), 7.14 (d, J=8.8 Hz, 2H), 7.31-7.63 (m, 5H), 7.68 (d, J=8.8 Hz, 2H), 7.73-7.81 (m, 1H), 12.55 (br s, 1H).

Step 3 Synthesis of Compound of Example 42

To a solution (2 mL) of the compound (90.5 mg, 0.153 mmol) of Step 2 in dichloromethane, trifluoroacetic acid (1 mL) was added, and stirred at room temperature for 1 hour. The solvent was distilled away under reduced pressure. The resulting residue was purified by reversed-phase HPLC in the same manner as in Step 2 of Example 1 to thus obtain the title compound.

Yield: 32.8 mg (0.0542 mmol), percentage yield: 35%
MS (ESI, m/z) 492 [M+H]$^+$
$^1$H NMR (DMSO-d$_6$, 400 MHz) δ 1.76-2.32 (m, 4H), 3.45-3.63 (m, 2H), 4.30-4.49 (m, 3H), 5.12-5.28 (m, 2H), 6.60 (br s, 1H), 6.93-7.03 (m, 2H), 7.12 (d, J=8.8 Hz, 2H), 7.31-7.67 (m, 6H), 12.67 (br s, 1H).

Example 43

1-(3-{[(4',5'-difluoro-2'-formylbiphenyl-4-yl)oxy]methyl}benzoyl)-L-proline

An operation similar to that in Example 3 was performed using 4,5-difluoro-2-formylphenylboronic acid (97 mg, 0.52 mmol) in place of 4-fluorobenzofuran-7-boronic acid to thus obtain the title compound.

Yield: 90 mg (0.19 mmol), percentage yield: 46%
MS (ESI, m/z) 466 [M+H]$^+$

Example 44

1-[3-({[4',5'-difluoro-2'-(methoxycarbonyl) biphenyl-4-yl]oxy}methyl)benzoyl]-L-proline An operation similar to that in Example 3 was performed using methyl 4,5-difluoro-2-(4,4,5,5-tetramethyl-1,3,2-dioxaborolan-2-yl)benzoate (155 mg, 0.52 mmol) in place of 4-fluorobenzofuran-7-boronic acid to thus obtain the title compound.

Yield: 70 mg (0.14 mmol), percentage yield: 32%
MS (ESI, m/z) 496 [M+H]+

Example 45

1-[3-({4-[4,5-difluoro-3-(methoxymethyl)-1-benzofuran-7-yl]phenoxy}methyl)benzoyl]-L-proline Step 1 Synthesis of 7-bromo-4,5-difluoro-3-(methoxymethyl)-1-benzofuran To the compound (49.4 mg, 0.200 mmol) of Step 1 of Example 21, N-bromosuccinimide (hereinafter, NBS) (39.2 mg, 0.220 mmol), and a catalytic amount of benzoyl peroxide (hereinafter, BPO), carbon tetrachloride (2 mL) was added, and heated under reflux overnight. After the resultant was returned to room temperature, the insoluble material was filtered off. The solvent was distilled away under reduced pressure. The resulting residue was dissolved in methanol (2 mL), and a 25% sodium methoxide methanol solution (0.2 mL) was added thereto and heated under reflux for 3 hours. The resultant was returned to room temperature, and the solvent was distilled away under reduced pressure. To the resulting residue, 1 N hydrochloric acid (1 mL) and a saturated aqueous ammonium chloride solution were added, and extraction was performed with ethyl acetate. The organic phase was dried over anhydrous magnesium sulfate. The solvent was distilled away under reduced pressure. The resulting residue was purified by silica gel chromatography to thus obtain the title compound.

Yield: 22.9 mg (0.0826 mmol), percentage yield: 41%
$^1$H NMR (CDCl$_3$, 400 MHz) δ 3.47 (s, 3H), 4.62 (d, J=1.0 Hz, 2H), 7.30-7.38 (m, 1H), 7.63-7.68 (m, 1H).

Step 2 Synthesis of Compound of Example 45

An operation similar to that in Step 2 of Example 15 was performed using the compound (22.9 mg, 0.0826 mmol) of Step 1 in place of 7-bromo-4,5-difluoro-1-benzofuran to thus obtain the title compound.

Yield: 22.9 mg (0.0439 mmol), percentage yield: 53%
MS (ESI, m/z) 522 [M+H]$^+$
$^1$H NMR (DMSO-d$_6$, 400 MHz) δ 1.76-2.32 (m, 4H), 3.32 (s, 3H), 3.42-3.63 (m, 2H), 4.32-4.45 (m, 1H), 4.54-4.63 (m, 2H), 5.18-5.31 (m, 2H), 7.15-7.22 (m, 2H), 7.40-7.66 (m, 5H), 7.78-7.84 (m, 2H), 8.16 (s, 1H), 12.55 (br s, 1H).

Example 46

1-[3-({4-[3-(cyanomethyl)-4,5-difluoro-1-benzofuran-7-yl]phenoxy}methyl)benzoyl]-L-proline Step 1 Synthesis of (7-bromo-4,5-difluoro-1-benzofuran-3-yl)acetonitrile To the compound (98.8 mg, 0.400 mmol) of Step 1 of Example 21, NBS (78.3 mg, 0.440 mmol), and a catalytic amount of BPO, carbon tetrachloride (4 mL) was added, and heated under reflux overnight. The resultant was returned to room temperature, and the solvent was distilled away under reduced pressure. The resulting residue was diluted with dichloromethane, washed with a saturated aqueous sodium hydrogen carbonate solution and saturated brine, and then dried over anhydrous magnesium sulfate. The solvent was distilled away under reduced pressure. The resulting residue was dissolved in acetonitrile (2 mL), and sodium cyanide (39.2 mg, 0.800 mmol) and water (0.2 mL) were added thereto, and stirred at 50° C. for 30 minutes. To the reaction solution, a 1 N sodium hydroxide aqueous solution was added. After concentrated under reduced pressure, the resultant was diluted with ethyl acetate, washed with water and saturated brine, and then dried over anhydrous magnesium sulfate. The solvent was distilled away under reduced pressure. The resulting residue was purified by silica gel chromatography to thus obtain the title compound.

Yield: 38.8 mg (0.143 mmol), percentage yield: 36%
$^1$H NMR (CDCl$_3$, 400 MHz) δ 3.89 (d, J=1.4 Hz, 2H), 7.38-7.43 (m, 1H), 7.76 (s, 1H).

Step 2 Synthesis of Compound of Example 46

An operation similar to that in Step 2 of Example 15 was performed using the compound (37.0 mg, 0.136 mmol) of Step 1 in place of 7-bromo-4,5-difluoro-1-benzofuran to thus obtain the title compound.

Yield: 29.4 mg (0.0569 mmol), percentage yield: 42%
MS (ESI, m/z) 517 [M+H]$^+$
$^1$H NMR (DMSO-d$_6$, 400 MHz) δ 1.77-2.32 (m, 4H), 3.40-3.63 (m, 2H), 4.18-4.26 (m, 2H), 4.32-4.46 (m, 1H), 5.18-5.30 (m, 2H), 7.15-7.22 (m, 2H), 7.40-7.97 (m, 7H), 8.15-8.25 (m, 1H), 12.54 (br s, 1H).

Example 47

1-[3-({[3',4'-difluoro-5'-(prop-2-yn-1-yloxy) biphenyl-4-yl]oxy}methyl)benzoyl]-L-proline Step 1 Synthesis of tert-butyl 1-(3-{[(3',4'-difluoro-5'-hydroxybiphenyl-4-yl)oxy]methyl}benzoyl)-L-prolinate DMF (125 mL) was added to 4-(4,4,5,5-tetramethyl-1,3,2-dioxaborolan-2-yl)phenol (8.46 g, 38 mmol), methyl 3-(bromomethyl)benzoate (8.8 g, 38 mmol), and potassium carbonate (10.6 g, 77 mmol), and stirred at room temperature overnight. The resultant was diluted with ethyl acetate, washed with water and saturated brine, and then dried over anhydrous magnesium sulfate. The solvent was distilled away under reduced pressure. To the resulting residue, methanol (150 mL), water (30 mL), and lithium hydroxide (4.8 g, 114 mmol) were added, and stirred at room temperature overnight. After the solvent was distilled away under reduced pressure, the resultant was diluted with ethyl acetate, then washed with 1 N hydrochloric acid and saturated brine, and dried over anhydrous magnesium sulfate. The solvent was distilled away under reduced pressure. To the resulting residue, dichloromethane (150 mL), WSC (7.34 g, 38.2 mmol), tert-butyl L-prolinate (7.95 g, 38.2 mmol), and triethylamine (9.65 ml, 69.4 mmol) were added, and stirred at room temperature overnight. After washed with water, 1 N hydrochloric acid, 1 N sodium hydroxide, and saturated brine, the resultant was dried over anhydrous magnesium sulfate. The solvent was distilled away under reduced pressure, and the residue was purified by silica gel chromatography (hexane/ethyl acetate). To the resulting compound (451 mg, 1.0 mmol), 5-bromo-2,3-difluorophenol (230 mg, 1.1 mmol), sodium carbonate (160 mg, 1.5 mmol), and Pd(dppf)Cl2 (catalytic amount), 1,4-dioxane (12 mL) and water (4 mL) were added, and stirred at 100° C. for 2 hours. The reaction solution was concentrated under reduced pressure. To the residue, ethyl acetate and 1 N hydrochloric acid were added and stirred. After that, the insoluble material was filtered off, and extraction was performed with ethyl acetate. The organic phase was washed with saturated brine, and then dried over anhydrous magnesium sulfate. After the solvent was distilled away under reduced pressure, the resulting residue was purified by reversed-phase HPLC in the same manner as in Step 2 of Example 1 to thus obtain the title compound.

Yield: 230 mg (0.45 mmol), percentage yield: 45%
MS (ESI, m/z) 510 [M+H]$^+$

Step 2 Synthesis of compound of Example 47

An operation similar to that in Step 2 of Example 34 was performed using the compound (106 mg, 0.208 mmol) of Step 1 in place of tert-butyl 1-(3-{[(4',5'-difluoro-2'-hydroxybiphenyl-4-yl)oxy]methyl}benzoyl)-L-prolinate to thus obtain the title compound.

Yield: 75.9 mg (0.154 mmol), percentage yield: 74%
MS (ESI, m/z) 492 [M+H]$^+$
$^1$H NMR (DMSO-d$_6$, 400 MHz) δ 1.75-2.33 (m, 4H), 3.43-3.62 (m, 2H), 3.67 (t, J=2.4 Hz, 1H), 4.31-4.44 (m, 1H), 5.06 (d, J=2.4 Hz, 2H), 5.16-5.28 (m, 2H), 7.09-7.15 (m, 2H), 7.28-7.36 (m, 2H), 7.40-7.62 (m, 4H), 7.62-7.68 (m, 2H), 12.52 (br s, 1H).

Example 48

1-[3-({[3'-(cyanomethoxy)-4',5'-difluorobiphenyl-4-yl]oxy}methyl)benzoyl]-L-proline An operation similar to that in Example 35 was performed using the compound (81.7 mg, 0.160 mmol) obtained in Step 1 of Example 47 in place of tert-butyl 1-(3-{[(4',5'-difluoro-2'-hydroxybiphenyl-4-yl)oxy]methyl}benzoyl)-L-prolinate to thus obtain the title compound.

Yield: 37.6 mg (0.0763 mmol), percentage yield: 48%
MS (ESI, m/z) 493 [M+H]$^+$
$^1$H NMR (DMSO-d$_6$, 400 MHz) δ 1.74-2.34 (m, 4H), 3.55-3.65 (m, 2H), 4.29-4.46 (m, 1H), 5.15-5.31 (m, 2H), 5.42 (s, 2H), 7.11-7.17 (m, 2H), 7.31-7.63 (m, 6H), 7.66-7.71 (m, 2H), 12.63 (br s, 1H).

Example 49

1-[3-({[3',4'-difluoro-5'-(2-oxopropoxy) biphenyl-4-yl]oxy}methyl)benzoyl]-L-proline Step 1 Synthesis of tert-butyl 1-[3-({[3',4'-difluoro-5'-(2-oxopropoxy)biphenyl-4-yl]oxy}methyl)benzoyl]-L-prolinate The compound (106 mg, 0.208 mmol) of Step 1 of Example 47 was dissolved in DMF (2 mL), and potassium carbonate (57.5 mg, 0.416 mmol) and bromoacetone (0.0192 mL, 0.229 mmol) were added thereto, and stirred at room temperature for 5 hours. The solvent was distilled away under reduced pressure. The resulting residue was diluted with ethyl acetate, washed with water and saturated brine, and then dried over anhydrous magnesium sulfate. The resultant was purified by silica gel chromatography to thus obtain the title compound.

Yield: 106 mg (0.187 mmol), percentage yield: 90%
MS (ESI, m/z) 566 [M+H]$^+$

Step 2 Synthesis of Compound of Example 49

To a solution of the compound (40.0 mg, 0.0707 mmol) of Step 1 in dichloromethane (2 mL), trifluoroacetic acid (1 mL) was added, and stirred at room temperature for 1 hour. The solvent was distilled away under reduced pressure. The resulting residue was purified by reversed-phase HPLC in the same manner as in Step 2 of Example 1 to thus obtain the title compound.

Yield: 26.8 mg (0.0526 mmol), percentage yield: 74%
MS (ESI, m/z) 510 [M+H]$^+$
$^1$H NMR (DMSO-d$_5$, 400 MHz) δ 1.76-2.01 (m, 3H), 2.17 (s, 3H), 2.20-2.31 (m, 1H), 3.42-3.63 (m, 2H), 4.30-4.45 (m, 1H), 5.10 (s, 2H), 5.15-5.28 (m, 2H), 7.06-7.16 (m, 3H), 7.23-7.66 (m, 7H), 12.55 (br s, 1H).

Example 50

1-[3-({[3',4'-difluoro-5'-(2-hydroxypropoxy) biphenyl-4-yl]oxy}methyl)benzoyl]-L-proline To a solution (1.5 mL) of the compound (66.0 mg, 0.117 mmol) of Step 1 of Example 49 in methanol, sodium borohydride (5.3 mg, 0.14 mmol) was added, and stirred at room temperature for 1 hour. After a saturated aqueous ammonium chloride solution was added to the reaction solution, the mixture was concentrated under reduced pressure, and extracted with ethyl acetate. The organic phase was washed with a saturated aqueous sodium hydrogen carbonate solution and saturated brine, and dried over anhydrous magnesium sulfate. After that, the solvent was distilled away under reduced pressure. The resulting residue was dissolved in dichloromethane (2 mL), and trifluoroacetic acid (1 mL) was added thereto, and stirred at room temperature for 1 hour. The solvent was distilled away under reduced pressure. The resulting residue was purified by reversed-phase HPLC in the same manner as in Step 2 of Example 1, to thus obtain the title compound.

Yield: 34.9 mg (0.0682 mmol), percentage yield: 58%
MS (ESI, m/z) 512 [M+H]$^+$
$^1$H NMR (DMSO-d$_6$, 400 MHz) δ 1.17 (d, J=6.0 Hz, 3H), 1.76-2.32 (m, 4H), 3.40-3.61 (m, 2H), 3.95-4.08 (m, 4H), 4.31-4.44 (m, 1H), 5.15-5.27 (m, 2H), 7.10 (d, J=8.8 Hz, 2H), 7.19-7.62 (m, 6H), 7.66 (d, J=8.8 Hz, 2H), 12.62 (br s, 1H).

Example 51

1-{3-[({4',5'-difluoro-2'-[(2-oxopropyl)thio]biphenyl-4-yl}oxy)methyl]benzoyl}-L-proline Step 1 Synthesis of
1-[(2-bromo-4,5-difluorophenyl)thio]acetone 2-Bromo-4,5-difluorobenzenethiol (900 mg, 4.00 mmol) and potassium carbonate (1.11 g, 8.00 mmol) were suspended in DMF (20 mL), and bromoacetone (0.403 mL, 4.80 mmol) was added thereto, and stirred at room temperature overnight. The reaction solution was concentrated under reduced pressure. After diluted with ethyl acetate, the resultant was washed with water and saturated brine, and dried over anhydrous magnesium sulfate. The solvent was distilled away under reduced pressure. The resulting residue was purified by silica gel chromatography (hexane/ethyl acetate) to thus obtain the title compound.

Yield: 804 mg (2.86 mmol), percentage yield: 71%
$^1$H NMR (CDCl$_3$, 400 MHz) δ 2.32 (s, 3H), 3.69 (s, 2H), 7.19 (dd, J=10.4, 7.8 Hz, 1H), 7.42 (dd, J=9.4, 7.5 Hz, 1H).

Step 2 Synthesis of Compound of Example 51

An operation similar to that in Step 2 of Example 15 was performed using the compound (28.1 mg, 0.100 mmol) of Step 1 in place of 7-bromo-4,5-difluoro-1-benzofuran to thus obtain the title compound.

Yield: 9.7 mg (0.019 mmol), percentage yield: 18%
MS (ESI, m/z) 526 [M+H]$^+$

Example 52

1-{3-[({4',5'-difluoro-2'-[(hydroxyimino)methyl]biphenyl-4-yl}oxy)methyl]benzoyl}-L-proline The compound (20 mg, 0.043 mmol) of Example 43 was dissolved in acetic acid (5 mL), and sodium acetate (45 mg, 0.56 mmol) and hydroxylamine hydrochloride (14 mg, 0.21 mmol) were added thereto, and stirred at 60° C. for 2 hours. After that, acetic anhydride (0.026 mL, 0.28 mmol) was added thereto, and stirred at 100° C. for 2 hours. After cooling, the solvent was distilled away, and the resulting residue was purified by reversed-phase HPLC in the same manner as in Step 2 of Example 1 to thus obtain the title compound.

Yield: 7 mg (0.015 mmol), percentage yield: 34%
MS (ESI, m/z) 481 [M+H]$^+$

Example 53

1-(3-{[4-(3-cyano-4,5-difluoro-1-benzofuran-7-yl)phenoxy]methyl}benzoyl-L-proline Step 1 Synthesis of
7-bromo-3-bromomethyl-4,5-difluoro-1-benzofuran the compound (2.6 g, 10.5 mmol) of Step 1 of Example 21, NBS (2.06 g, 11.58 mmol), BPO (catalytic amount), and carbon tetrachloride (120 mL) were added, and heated under reflux overnight. After cooling, the solvent was distilled away. After diluted with ethyl acetate, the resultant was washed with water and saturated brine, and then dried over anhydrous magnesium sulfate. The solvent was distilled away, and the resulting residue was purified by silica gel chromatography (hexane/ethyl acetate) to thus obtain the title compound.

Yield: 1.47 g (4.51 mmol), percentage yield: 43%

Step 2 Synthesis of
7-bromo-4,5-difluoro-3-hydroxymethyl-1-benzofuran

The compound (1.47 g, 4.51 mmol) obtained in Step 1 was dissolved in acetonitrile (50 mL), and potassium acetate (660 mg, 6.76 mmol) was added thereto, and stirred at 60° C. for 3 hours. After cooling, the solvent was distilled away, and to the resulting residue, methanol (20 mL) and potassium carbonate (1.56 g, 11.28 mmol) were added, and stirred at room temperature for 2 hours. The solvent was distilled away. After diluted with ethyl acetate, the resultant was washed with water and saturated brine, and then dried over anhydrous magnesium sulfate. The solvent was distilled away, and the resulting residue was purified by silica gel chromatography (hexane/ethyl acetate) to thus obtain the title compound.

Yield: 900 mg (3.42 mmol), percentage yield: 76%

Step 3 Synthesis of
7-bromo-4,5-difluoro-3-formyl-1-benzofuran

The compound obtained in Step 2 (700 mg, 2.66 mmol) was dissolved in dichloromethane (50 mL), and manganese dioxide (1.4 g) was added thereto, and stirred at room temperature overnight. After filtration, the solvent was distilled away, and the resulting residue was purified by silica gel chromatography (hexane/ethyl acetate) to thus obtain the title compound.

Yield: 400 mg (1.53 mmol), percentage yield: 58%

Step 4 Synthesis of 7-bromo-3-cyano-4,5-difluoro-1-benzofuran

The compound (360 mg, 1.38 mmol) obtained in Step 3 was dissolved in acetic acid (5 mL), and sodium acetate (450 mg, 5.5 mmol) and hydroxylamine hydrochloride (140 mg, 2.1 mmol) were added thereto, and stirred at 60° C. for 2 hours. After that, acetic anhydride (0.26 mL, 2.75 mmol) was added thereto, and stirred at 100° C. for 2 hours. After cooling, the solvent was distilled away, and the resulting residue was purified by silica gel chromatography (hexane/ethyl acetate) to thus obtain the title compound.

Yield: 290 mg (1.12 mmol), percentage yield: 81%

Step 5 Synthesis of Compound of Example 53

An operation similar to that in Step 2 of Example 15 was performed using the compound (290 mg, 1.12 mmol) obtained in Step 4 in place of 7-bromo-4,5-difluoro-1-benzofuran to thus obtain the title compound.

Yield: 70 mg (0.14 mmol), percentage yield: 12%
MS (ESI, m/z) 503 [M+H]$^+$

Example 54

1-(3-{[4-(2-cyano-4,5-difluoro-1-benzofuran-7-yl)phenoxy]methyl}benzoyl-L-proline

Step 1 Synthesis of 7-bromo-2-bromomethyl-4,5-difluoro-1-benzofuran

An operation similar to that in Step 1 of Example 53 was performed using the compound (2.6 g, 10.5 mmol) of Step 1 of Example 23 in place of the compound of Step 1 of Example 21 to thus obtain the title compound.

Yield: 3.43 g (10.5 mmol), percentage yield: 100%
$^1$H NMR (CDCl$_3$, 400 MHz) δ 4.56 (s, 2H), 6.95 (s, 1H), 7.35 (dd, J=10.1, 6.9 Hz, 1H).

Step 2 Synthesis of 7-bromo-4,5-difluoro-2-hydroxymethyl-1-benzofuran

An operation similar to that in Step 2 of Example 53 was performed using the compound (1.8 g, 5.52 mmol) obtained in Step 1 in place of the compound of Step 1 of Example 53 to thus obtain the title compound.

Yield: 1.08 g (4.1 mmol), percentage yield: 74%
$^1$H NMR (CDCl$_3$, 400 MHz) δ 2.01-2.12 (m, 1H), 4.81 (s, 2H), 6.88 (t, J=0.8 Hz, 1H), 7.31 (dd, J=10.1, 6.9 Hz, 1H).

Step 3 7-bromo-4,5-difluoro-2-formyl-1-benzofuran

An operation similar to that in Step 3 of Example 53 was performed using the compound (1.08 g, 4.1 mmol) obtained in Step 2 in place of the compound of Step 2 of Example 53 to thus obtain the title compound.

Yield: 720 mg (2.76 mmol), percentage yield: 67%

Step 4 7-bromo-2-cyano-4,5-difluoro-1-benzofuran

An operation similar to that in Step 4 of Example 53 was performed using the compound (360 mg, 1.38 mmol) obtained in Step 3 in place of the compound of Step 3 of Example 53 to thus obtain the title compound.

Yield: 260 mg (1.01 mmol), percentage yield: 81%

Step 5

An operation similar to that in Step 2 of Example 15 was performed using the compound (260 mg, 1.01 mmol) obtained in Step 4 in place of 7-bromo-4,5-difluoro-1-benzofuran to thus obtain the title compound.

Yield: 140 mg (0.28 mmol), percentage yield: 24%
MS (ESI, m/z) 503 [M+H]$^+$

Example 55

1-(3-{[4-(4,5-difluoro-3-methyl-1-benzothien-7-yl)phenoxy]methyl}benzoyl)-L-proline

Step 1 Synthesis of 7-bromo-4,5-difluoro-3-methyl-1-benzothiophene

A polyphosphoric acid (1.86 g) was suspended in chlorobenzene (8 mL), and a solution (8 mL) of the compound (730 mg, 2.60 mmol) of Step 1 of Example 51 in chlorobenzene was added thereto at 120° C., and stirred at 140° C. overnight. After further stirred at 155° C. two nights, the resultant was returned to room temperature, and the reaction solution was concentrated under reduced pressure, and diluted with ethyl acetate. To the mixture liquid, a 1 N sodium hydroxide aqueous solution was added under ice-cooling for the neutralization, and the insoluble material was filtered off. The filtrate was extracted with ethyl acetate, washed with saturated brine, and then dried over anhydrous magnesium sulfate. The resultant was concentrated under reduced pressure. The resulting residue was purified by silica gel chromatography (hexane) to thus obtain the title compound.

Yield: 430 mg (1.63 mmol), percentage yield: 63%
$^1$H NMR (CDCl$_3$, 400 MHz) δ 2.57 (dd, J=2.5, 1.2 Hz, 3H), 7.11-7.13 (m, 1H), 7.32-7.38 (m, 1H).

Step 2 Synthesis of Compound of Example 55

An operation similar to that in Step 2 of Example 15 was performed using the compound (32.9 mg, 0.125 mmol) of Step 1 in place of 7-bromo-4,5-difluoro-1-benzofuran to thus obtain the title compound.

Yield: 33.4 mg (0.0658 mmol), percentage yield: 53%
MS (ESI, m/z) 508 [M+1-1]$^+$
$^1$H NMR (DMSO-d$_6$, 400 MHz) δ 1.76-2.32 (m, 4H), 2.56 (d, J=1.5 Hz, 3H), 3.43-3.63 (m, 2H), 4.32-4.46 (m, 1H), 5.16-5.31 (m, 2H), 7.16-7.21 (m, 2H), 7.32-7.66 (m, 8H), 12.62 (br s, 1H).

Example 56

1-[3-({4-[4,5-difluoro-3-(hydroxymethyl)-1-benzofuran-7-yl]phenoxy}methyl)benzoyl]-L-proline An operation similar to that in Step 2 of Example 15 was performed using the compound (39.5 mg, 0.150 mmol) of Step 2 of Example 53 in place of 7-bromo-4,5-difluoro-1-benzofuran to thus obtain the title compound.

Yield: 18.2 mg (0.0359 mmol), percentage yield: 24%
MS (ESI, m/z) 508 [M+H]$^+$
$^1$H NMR (DMSO-d$_6$, 400 MHz) δ 1.76-2.32 (m, 4H), 3.39-3.61 (m, 2H), 4.32-4.44 (m, 1H), 4.62-4.72 (m, 2H), 5.16-5.31 (m, 2H), 7.14-7.21 (m, 2H), 7.40-7.64 (m, 5H), 7.77-7.84 (m, 2H), 8.02 (s, 1H), 12.71 (br s, 1H).

Example 57

1-{3-[(4-{2-[amino(hydroxyimino)methyl]4,5-difluoro-1-benzofuran-7-yl}phenoxy)methyl]benzoyl}-L-proline The compound (20 mg, 0.04 mmol) of Example 54 was dissolved in ethanol (5 mL), and hydroxylamine hydrochloride (14 mg, 0.21 mmol) and triethylamine (0.058 mL, 0.42 mmol) were added thereto, and stirred at room temperature for 2 hours. After that, the solvent was distilled away, and the resulting residue was purified by reversed-phase HPLC in the same manner as in Step 2 of Example 1 to thus obtain the title compound.

Yield: 4.4 mg (0.008 mmol), percentage yield: 20%
MS (ESI, m/z) 536 [M+H]$^+$

Example 58

1-{3-[(4-{4,5-difluoro-2-[(hydroxyimino)methyl]-1-benzofuran-7-yl}phenoxy)methyl]benzoyl}-L-proline The compound (20 mg, 0.04 mmol) of Example 54 was dissolved in acetic acid (5 mL), and sodium acetate (45 mg, 0.56 mmol) and hydroxylamine hydrochloride (14 mg, 0.21 mmol) were added thereto, and at 60° C. for 2 hours and stirred. After that, acetic anhydride (0.026 mL, 0.28 mmol) were added to, at 100° C. for 2 hours and stirred. After cooling, the solvent was distilled away, and the resulting residue was purified by reversed-phase HPLC in the same manner as in Step 2 of Example 1 to thus obtain the title compound.

Yield: 3 mg (0.006 mmol), percentage yield: 15%
MS (ESI, m/z) 521 [M+H]$^+$

Example 59

(2S)-1-(3-{[4-(4,5-difluoro-1-benzofuran-7-yl) phenoxy]methyl}benzoyl)azetidine-2-carboxylic acid Step 1 Synthesis of 3-{[4-(4,4,5,5-tetramethyl-1,3,2-dioxaborolan-2-yl)phenoxy]methyl}benzoic acid DMF (125 mL) was added to 4-(4,4,5,5-tetramethyl-1,3,2-dioxaborolan-2-yl)phenol (8.46 g, 38 mmol), methyl 3-(bromomethyl)benzoate (8.8 g, 38 mmol), and potassium carbonate (10.6 g, 77 mmol), and stirred at room temperature overnight. The resultant was diluted with ethyl acetate, washed with water and saturated brine, and then dried over anhydrous magnesium sulfate. The solvent was distilled away under reduced pressure, and to the resulting residue, methanol (150 mL), water (30 mL), and lithium hydroxide (4.8 g, 114 mmol) were added, and stirred at room temperature overnight. After the solvent was distilled away under reduced pressure, the resultant was diluted with ethyl acetate, then washed with 1 N hydrochloric acid and saturated brine, and dried over anhydrous magnesium sulfate. After the solvent was distilled away under reduced pressure, the solid was collected by filtration.

Yield: 7.17 g (20.3 mmol), percentage yield: 53%

Step 2 Synthesis of 3-{[4-(4,5-difluoro-1-benzofuran-7-yl)-phenoxy]methyl}benzoic acid To the compound (1.67 g, 4.72 mmol) obtained in Step 1, 7-bromo-4,5-difluoro-1-benzofuran (1.1 g, 4.72 mmol), sodium carbonate (1.0 g, 9.44 mmol), and Pd(dppf)Cl2 (catalytic amount), 1,4-dioxane (24 mL) and water (8 mL) were added, and stirred at 100° C. for 2 hours. The reaction solution was concentrated under reduced pressure. To the residue, ethyl acetate and 1 N hydrochloric acid were added and stirred. After that, the insoluble material was filtered off, and extraction was performed with ethyl acetate. The organic phase was washed with saturated brine, and then dried over anhydrous magnesium sulfate. The solvent was distilled away under reduced pressure, and the solid was collected by filtration.

Yield: 1.43 g (3.76 mmol), percentage yield: 79%
MS (ESI, m/z) 381 [M+H]$^+$

Step 3 Synthesis of Compound of Example 59

An operation similar to that in Step 4 of Example 10 was performed using the compound (38.0 mg, 0.100 mmol) of Step 2 in place of 3-{[4-(5-fluoro-2,3-dihydro-1-benzofuran-7-yl)phenoxy]methyl}benzoic acid, and (2S)-azetidine-2-carboxylic acid (30.3 mg, 0.300 mmol) in place of L-proline to thus obtain the title compound.

Yield: 7.75 mg (0.0167 mmol), percentage yield: 17%
MS (ESI, m/z) 464 [M+H]$^+$
$^1$H NMR (DMSO-d$_6$, 400 MHz) δ 2.90-3.04 (m, 3H), 3.96 (s, $^1$H), 4.15 (s, 1H), 5.18-5.30 (m, 2H), 7.15-7.22 (m, 2H), 7.23 (d, J=2.3 Hz, 1H), 7.35-7.65 (m, 5H), 7.80-7.86 (m, 2H), 8.19 (d, J=2.2 Hz, 1H), 12.83 (br s, 1H).

Example 60

1-(3-{[4-(4,5-difluoro-1-benzofuran-7-yl)-2-fluorophenoxy]methyl}benzoyl)-L-proline Step 1 Synthesis of 3-{[4-(4,5-difluorobenzofuran-7-yl)-2-fluoro-phenoxy]methyl}benzoic acid 1,4-Dioxane (12 mL) and water (4 mL) were added to 2-fluoro-4-hydroxyphenylboronic acid (475 mg, 3.0 mmol), 7-bromo-4,5-difluoro-1-benzofuran (590 mg, 2.53 mmol), sodium carbonate (540 mg, 5.1 mmol), and Pd(dppf)Cl2 (catalytic amount), and stirred at 100° C. for 2 hours. The reaction solution was concentrated under reduced pressure. To the residue, ethyl acetate and 1 N hydrochloric acid were added and stirred. After that, the insoluble material was filtered off, and extraction was performed with ethyl acetate. The organic phase was washed with saturated brine, and then dried over anhydrous magnesium sulfate. The solvent was distilled away under reduced pressure. Then, to the resulting residue, methyl 3-(bromomethyl)benzoate (595 mg, 2.6 mmol), potassium carbonate (414 mg, 3.0 mmol), and DMF (4 mL) were added, and stirred overnight. After diluted with ethyl acetate, the resultant was washed with water and saturated brine, and dried over anhydrous magnesium sulfate. The solvent was distilled away under reduced pressure. To the resulting residue, methanol (5 mL), water (2 mL), THF (5 mL), and lithium hydroxide (210 mg, 5.0 mmol) were added, and stirred at room temperature overnight. The reaction solution was concentrated under reduced pressure, and extraction was performed with ethyl acetate. The organic phase was washed with saturated brine, and then dried over anhydrous magnesium sulfate. After the solvent was distilled away under reduced pressure, the resulting solid was collected by filtration to thus obtain the title compound.

Yield: 241 mg (0.60 mmol), percentage yield: 24%

Step 2 Synthesis of Compound of Example 60

A similar operation similar to that in Step 4 of Example 10 was performed using the compound (40.0 mg, 0.100 mmol) of Step 1 in place of 3-{[4-(5-fluoro-2,3-dihydro-1-benzofuran-7-yl)phenoxy]methyl}benzoic acid to thus obtain the title compound.

Yield: 21.7 mg (0.0559 mmol), percentage yield: 55%
MS (ESI, m/z) 496 [M+H]$^+$

¹H NMR (DMSO-d₆, 400 MHz) δ 1.74-2.02 (m, 3H), 2.21-2.35 (m, 1H), 3.49-3.54 (m, 2H), 4.33-4.46 (m, 1H), 5.26-5.38 (m, 2H), 7.25 (d, J=2.2 Hz, 1H), 7.34-7.74 (m, 7H), 7.80 (dd, J=12.8, 2.1 Hz, 1H), 8.21 (d, J=2.2 Hz, 1H), 12.57 (br s, 1H).

Example 61

1-[3-({[2'-(cyanomethyl)-4',5'-difluorobiphenyl-4-yl]oxy}methyl)benzoyl]-L-proline Step 1 Synthesis of
2-(2-bromo-4,5-difluorophenyl)acetamide 2-Bromo-4,5-difluorophenylacetic acid (251 mg, 1.00 mmol) was dissolved in thionyl chloride (3 mL), and stirred at 50° C. for 30 minutes. The resultant was concentrated under reduced pressure, and the residue was dissolved in dichloromethane (5 mL). After that, 28% ammonia water (1 mL) were added thereto under ice-cooling, and stirred at room temperature for 1 hour. To the reaction solution, ammonium carbonate (50 mg) was added, and further stirred at room temperature for 1 hour. Then, 1 N hydrochloric acid was added thereto until the resultant became acidic under ice-cooling. The reaction solution was extracted with ethyl acetate, and the organic phase was washed with a saturated aqueous sodium hydrogen carbonate solution and saturated brine, and then dried over anhydrous magnesium sulfate. The solvent was distilled away under reduced pressure to thus obtain the title compound without purification.
Yield: 186 mg (0.744 mmol), percentage yield: 74%
MS (ESI, m/z) 250 [M+H]⁺
¹H NMR (DMSO-d₆, 400 MHz) δ 3.56 (s, 2H), 7.24 (d, J=174.2 Hz, 2H), 7.51 (dd, J=11.7, 8.6 Hz, 1H), 7.80 (dd, J=10.3, 7.8 Hz, 1H).

Step 2 Synthesis of
(2-bromo-4,5-difluorophenyl)acetonitrile

The compound (143 mg, 0.572 mmol) of Step 1 was dissolved in THF. Pyridine (0.138 mL, 1.71 mmol) was added thereto, trifluoroacetic anhydride (0.119 mL, 0.858 mmol) was added thereto at −5° C. to 0° C., and stirred at room temperature for 1 hour. The reaction solution was concentrated under reduced pressure. After diluted with ethyl acetate, the resultant was washed with 1 N hydrochloric acid, a saturated aqueous sodium hydrogen carbonate solution, and saturated brine, and then dried over anhydrous magnesium sulfate. The solvent was distilled away under reduced pressure to thus obtain the title compound without purification.
Yield: 126 mg (0.543 mmol), percentage yield: 95%
¹H NMR (CDCl₃, 400 MHz) δ 3.79 (s, 2H), 7.38-7.44 (m, 1H), 7.44-7.50 (m, 1H).

Step 3 Synthesis of Compound of Example 61

An operation similar to that in Step 2 of Example 15 was performed using the compound (34.3 mg, 0.148 mmol) of Step 2 in place of 7-bromo-4,5-difluoro-1-benzofuran to thus obtain the title compound.
Yield: 41.4 mg (0.0869 mmol), percentage yield: 59%
MS (ESI, m/z) 477 [M+H]⁺
¹H NMR (DMSO-d₆, 400 MHz) δ 1.77-2.33 (m, 4H), 3.43-3.63 (m, 2H), 3.88 (s, 2H), 4.30-4.46 (m, 1H), 5.14-5.26 (m, 2H), 7.14 (d, J=8.6 Hz, 2H), 7.29-7.68 (m, 8H), 12.54 (br s, 1H).

Example 62

1-(3-{[4-(4,5-difluoro-2-methyl-1-benzothien-7-yl)phenoxy]methyl}benzoyl)-L-proline Step 1 Synthesis of
7-bromo-4,5-difluoro-2-methyl-1-benzothiophene 2-Bromo-4,5-difluorothiophenol (4.68 g, 20.8 mmol), 2,3-dichloro-1-propene (2.1 mL, 22.9 mmol), potassium carbonate (3.45 g, 24.9 mmol), and acetone (100 mL) were added, and stirred at 60° C. for 2 hours. The solvent was distilled away under reduced pressure, and after diluted with ethyl acetate, the resultant was washed with water and saturated brine, and then dried over anhydrous magnesium sulfate. The solvent was distilled away, and to the resulting residue, dimethylaniline (50 mL) was added, and stirred at 220° C. overnight. After cooling, ethyl acetate and a 2 N hydrochloric acid aqueous solution were added to the reaction solution and stirred. After the insoluble material was filtered off, extraction was performed with ethyl acetate. The organic phase was washed with a saturated aqueous sodium hydrogen carbonate solution and saturated brine, and then dried over anhydrous magnesium sulfate. The solvent was distilled away under reduced pressure. The resulting residue was purified by silica gel chromatography (hexane) to thus obtain the title compound.
Yield: 4.12 g (15.66 mmol), percentage yield: 75%
¹H NMR (CDCl₃, 400 MHz) δ 2.61 (d, J=1.2 Hz, 3H), 7.18-7.21 (m, 1H), 7.27-7.31 (m, 1H).

Step 2 Synthesis of Compound of Example 62

An operation similar to that in Step 2 of Example 15 was performed using the compound (38.9 mg, 0.148 mmol) of Step 1 in place of 7-bromo-4,5-difluoro-1-benzofuran to thus obtain the title compound.
Yield: 36.9 mg (0.0727 mmol), percentage yield: 49%
MS (ESI, m/z) 508 [M+H]⁺
¹H NMR (DMSO-d₆, 400 MHz) δ 1.75-2.33 (m, 4H), 2.58 (s, 3H), 3.45-3.64 (m, 2H), 4.32-4.45 (m, 1H), 5.16-5.33 (m, 2H), 7.15-7.22 (m, 2H), 7.32-7.66 (m, 8H), 12.59 (s, 1H).

Example 63

N-(3-{[4-(4,5-difluoro-1-benzofuran-7-yl) phenoxy]methyl}benzoyl)-N-methyl-L-alanine An operation similar to that in Step 4 of Example 10 was performed using the compound (38.0 mg, 0.100 mmol) of Step 2 of Example 59 in place of 3-{[4-(5-fluoro-2,3-dihydro-1-benzofuran-7-yl)phenoxy]methyl}benzoic acid, and N-methyl-L-alanine (30.9 mg, 0.300 mmol) in place of L-proline to thus obtain the title compound.
Yield: 17.4 mg (0.0374 mmol), percentage yield: 37%
MS (ESI, m/z) 466 [M+H]⁺
¹H NMR (DMSO-d₆, 400 MHz) δ 1.29-1.47 (m, 3H), 2.81-2.91 (m, 3H), 4.23-4.99 (m, 1H), 5.25 (s, 2H), 7.15-7.21 (m, 2H), 7.23 (d, J=2.3 Hz, 1H), 7.27-7.66 (m, 5H), 7.82 (d, J=8.7 Hz, 2H), 8.18 (d, J=2.2 Hz, 1H), 12.98 (br s, 1H).

Example 64

(2S)-1-(3-{[4-(4,5-difluoro-1-benzofuran-7-yl) phenoxy]methyl}benzoyl)-2,5-dihydro-1H-pyrrole-2-carboxylic acid An operation similar to that in Step 4 of Example 10 was performed using the compound (38.0 mg, 0.100 mmol) of Step 2 of Example 59 in place of 3-{[4-(5-fluoro-2,3-dihydro-1-benzofuran-7-yl)phenoxy]methyl}benzoic acid, and (2S)-2,5-dihydro-1H-pyrrole-2-carboxylic acid (14.7 mg, 0.130 mmol) in place of L-proline to thus obtain the title compound.

Yield: 14.1 mg (0.0297 mmol), percentage yield: 30%
MS (ESI, m/z) 476 [M+H]$^+$
$^1$H NMR (DMSO-d$_6$, 400 MHz) δ 4.10-4.20 (m, 1H), 4.31-4.41 (m, 1H), 5.16-5.32 (m, 3H), 5.84-5.97 (m, 1H), 6.00-6.19 (m, 1H), 7.15-7.22 (m, 2H), 7.23 (d, J=2.3 Hz, 1H), 7.41-7.69 (m, 5H), 7.79-7.86 (m, 2H), 8.19 (d, J=2.2 Hz, 1H), 12.98 (br s, 1H).

Example 65

1-(3-{[4-(4,5-difluoro-2-formyl-1-benzothien-7-yl)phenoxy]methyl}benzoyl)-L-proline Step 1 Synthesis of 7-bromo-2-(bromomethyl)-4,5-difluoro-1-benzothiophene An operation similar to that in Step 1 of Example 53 was performed using the compound (386 mg, 1.47 mmol) of Step 1 of Example 62 in place of the compound of Step 1 of Example 21 to thus obtain the title compound.

Yield: 500 mg (1.47 mmol), percentage yield: 99%

Step 2 Synthesis of 7-bromo-4,5-difluoro-2-formyl-1-benzothiophene

Operations similar to those in Steps 2 and 3 of Example 53 were performed using 500 mg (1.47 mmol) of the compound obtained in Step 1 in place of the compound of Step 1 of Example 53 to thus obtain the title compound.

Yield: 244 mg (0.87 mmol), percentage yield: 59%

Step 3 Synthesis of Compound of Example 65

An operation similar to that in Step 2 of Example 15 was performed using the compound (244 mg, 0.87 mmol) obtained in Step 2 in place of 7-bromo-4,5-difluoro-1-benzofuran to thus obtain the title compound.

Yield: 55 mg (0.11 mmol), percentage yield: 12%
MS (ESI, m/z) 522 [M+H]$^+$

Example 66

1-[3-({4-[4,5-difluoro-2-(hydroxymethyl)-1-benzothien-7-yl]phenoxy}methyl)benzoyl]-L-proline The compound (12 mg, 0.022 mmol) of Example 65 was dissolved in methanol (2 mL), and sodium borohydride (2 mg, 0.045 mmol) was stirred at room temperature for 1 hour. The reaction solution was purified by reversed-phase HPLC in the same manner as in Step 2 of Example 1 to thus obtain the title compound.

Yield: 3 mg (0.006 mmol), percentage yield: 27%
MS (ESI, m/z) 520 [M+H]$^+$

Example 67

1-(3-{[4-(2-cyano-4,5-difluoro-1-benzothien-7-yl)phenoxy]methyl}benzoyl)-L-proline The compound (75 mg, 0.14 mmol) of Example 65 was dissolved in acetic acid (5 mL), and sodium acetate (45 mg, 0.56 mmol) and hydroxylamine hydrochloride (14 mg, 0.21 mmol) were added thereto, and stirred at 60° C. for 2 hours. After that, acetic anhydride (0.026 mL, 0.28 mmol) was added thereto, and stirred at 100° C. for 2 hours. After cooling, the solvent was distilled away, and the resulting residue was purified by reversed-phase HPLC in the same manner as in Step 2 of Example 1 to thus obtain the title compound.

Yield: 13 mg (0.025 mmol), percentage yield: 18%
MS (ESI, m/z) 519 [M+H]$^+$

Example 68

(4R)-3-(3-{[4-(4,5-difluoro-1-benzofuran-7-yl)phenoxy]methyl}benzoyl)-1,3-thiazolidine-4-carboxylic acid An operation similar to that in Step 4 of Example 10 was performed using the compound (38.0 mg, 0.100 mmol) of Step 2 of Example 59 in place of 3-{[4-(5-fluoro-2,3-dihydro-1-benzofuran-7-yl)phenoxy]methyl}benzoic acid, and (4R)-1,3-thiazolidine-4-carboxylic acid (40.0 mg, 0.300 mmol) in place of L-proline to thus obtain the title compound.

Yield: 1.41 mg (0.00285 mmol), percentage yield: 2.8%
MS (ESI, m/z) 496 [M+H]$^+$
$^1$H NMR (DMSO-d$_6$, 400 MHz) δ 2.83-3.05 (m, 2H), 3.96-4.31 (m, 2H), 4.30-5.74 (m, 3H), 7.15-7.22 (m, 2H), 7.23 (d, J=2.3 Hz, 1H), 7.45-7.67 (m, 5H), 7.79-7.85 (m, 2H), 8.19 (d, J=2.2 Hz, 1H).

Example 69

1-{3-[({4',5'-difluoro-2'-[(2-hydroxyethyl)thio]biphenyl-4-yl}oxy)methyl]benzoyl}-L-proline 2-Bromo-4,5-difluorothiophenol (438 mg, 1.95 mmol), ethylene carbonate (260 mg, 2.92 mmol), potassium carbonate (400 mg, 2.92 mmol), and DMF (10 ml) were added, and stirred at 100° C. for 2 hours. After diluted with ethyl acetate, the resultant was washed with water and saturated brine, and then dried over anhydrous magnesium sulfate. The solvent was distilled away, and the resulting residue was purified by silica gel chromatography (hexane). After that, an operation similar to that in Step 2 of Example 15 was performed using the above-obtained compound (60 mg, 0.22 mmol) in place of 7-bromo-4,5-difluoro-1-benzofuran to thus obtain the title compound.

Yield: 5 mg (0.01 mmol), percentage yield: 4%
MS (ESI, m/z) 515 [M+H]$^+$

Example 70

1-[3-({4-[4,5-difluoro-2-(hydroxymethyl)-1-benzofuran-7-yl]phenoxy}methyl)benzoyl]-L-proline An operation similar to that in Step 2 of Example 15 was performed using the compound (44.7 mg, 0.170 mmol) of Step 2 of Example 53 in place of 7-bromo-4,5-difluoro-1-benzofuran to thus obtain the title compound.

Yield: 12.0 mg (0.0236 mmol), percentage yield: 14%
MS (ESI, m/z) 508 [M+H]$^+$

Example 71

1-{3-[({2'-[(cyanomethyl)thio]-4',5'-difluorobiphenyl-4-yl}oxy)methyl]benzoyl}-L-proline

Step 1 Synthesis of [(2-bromo-4,5-difluorophenyl)thio]acetonitrile

An operation similar to that in Step 1 of Example 38 was performed using bromoacetonitrile (0.167 mL, 2.40 mmol) in place of iodomethane to thus obtain the title compound.

Yield: 500 mg (1.89 mmol), percentage yield: 95%

$^1$H NMR (CDCl$_3$, 400 MHz) δ 3.65 (s, 2H), 7.56-7.49 (m, 2H).

Step 2 Synthesis of Compound of Example 71

An operation similar to that in Step 2 of Example 15 was performed using the compound (44.9 mg, 0.170 mmol) of Step 1 in place of 7-bromo-4,5-difluoro-1-benzofuran to thus obtain the title compound.

Yield: 21.4 mg (0.0421 mmol), percentage yield: 25%

MS (ESI, m/z) 509 [M+H]$^+$ $^1$H NMR (DMSO-d$_6$, 400 MHz) δ 1.76-2.34 (m, 4H), 3.41-3.62 (m, 2H), 4.19 (s, 2H), 4.31-4.45 (m, 1H), 5.14-5.28 (m, 2H), 7.08-7.14 (m, 2H), 7.27-7.36 (m, 2H), 7.41-7.63 (m, 5H), 7.71 (dd, J=11.4, 7.8 Hz, 1H), 12.64 (br s, 1H).

Example 72

1-{3-[({2'-[(2-cyanoethyl)thio]-4',5'-difluorobiphenyl-4-yl}oxy)methyl]benzoyl}-L-proline

Step 1 Synthesis of 3-[(2-bromo-4,5-difluorophenyl)thio]propanenitrile

An operation similar to that in Step 1 of Example 38 was performed using 3-bromopropionitrile (0.196 mL, 2.40 mmol) in place of iodomethane to thus obtain the title compound.

Yield: 538 mg (1.89 mmol), percentage yield: 97%

$^1$H NMR (CDCl$_3$, 400 MHz) δ 2.65 (t, J=7.2 Hz, 1H), 3.16 (t, J=7.2 Hz, 1H), 7.32 (dd, J=10.0, 7.8 Hz, 1H), 7.49 (dd, J=9.4, 7.5 Hz, 1H).

Step 2 Synthesis of Compound of Example 72

An operation similar to that in Step 2 of Example 15 was performed using the compound (47.3 mg, 0.170 mmol) of Step 1 in place of 7-bromo-4,5-difluoro-1-benzofuran to thus obtain the title compound.

Yield: 21.5 mg (0.0411 mmol), percentage yield: 24%

MS (ESI, m/z) 523 [M+H]$^+$ $^1$H NMR (DMSO-d$_6$, 400 MHz) δ 1.75-2.32 (m, 4H), 2.76 (t, J=6.9 Hz, 2H), 3.16 (t, J=6.9 Hz, 2H), 3.42-3.61 (m, 2H), 4.32-4.45 (m, 1H), 5.13-5.26 (m, 2H), 7.06-7.13 (m, 2H), 7.28-7.54 (m, 5H), 7.56-7.68 (m, 3H), 12.54 (br s, 1H).

Example 73

Synthesis of 1-[3-({4-[4,5-difluoro-2-(methoxymethyl)-1-benzofuran-7-yl]phenoxy}methyl)benzoyl]-L-proline

Step 1 7-bromo-4,5-difluoro-2-(methoxymethyl)-1-benzofuran

The compound (489 mg, 1.50 mmol) of Step 1 of Example 54 was dissolved in methanol (7 mL), and a 25% sodium methoxide methanol solution (1.5 mL) were added thereto, and heated under reflux for 3 hours. The resultant was returned to room temperature, and the solvent was distilled away under reduced pressure. The resulting residue was diluted with ethyl acetate, washed with water and saturated brine, and then dried over anhydrous magnesium sulfate. The solvent was distilled away under reduced pressure. The resulting residue was purified by silica gel chromatography (hexane/ethyl acetate) to thus obtain the title compound.

Yield: 334 mg (1.21 mmol), percentage yield: 80%

$^1$H NMR (CDCl$_3$, 400 MHz) δ 3.48 (s, 3H), 4.57 (d, J=0.5 Hz, 2H), 6.87-6.90 (m, 1H), 7.31 (dd, J=10.1, 6.9 Hz, 1H).

Step 2 Synthesis of Compound of Example 73

An operation similar to that in Step 2 of Example 15 was performed using the compound (47.1 mg, 0.170 mmol) of Step 1 in place of 7-bromo-4,5-difluoro-1-benzofuran to thus obtain the title compound.

Yield: 56.5 mg (0.108 mmol), percentage yield: 64%

MS (ESI, m/z) 522 [M+H]$^+$ $^1$H NMR (DMSO-d$_6$, 400 MHz) δ 1.75-2.35 (m, 4H), 3.33 (s, 3H), 3.40-3.62 (m, 2H), 4.31-4.44 (m, 1H), 4.58 (s, 2H), 5.18-5.30 (m, 2H), 7.16-7.22 (m, 3H), 7.32-7.64 (m, 5H), 7.79-7.84 (m, 2H), 12.54 (br s, 1H).

Example 74

1-[3-({4-[4,5-difluoro-2-(methoxymethyl)-1-benzothien-7-yl]phenoxy}methyl)benzoyl]-L-proline

Step 1 Synthesis of 7-bromo-4,5-difluoro-2-(methoxymethyl)-1-benzothiophene

An operation similar to that in Step 1 of Example 73 was performed using the compound (121 mg, 0.354 mmol) of Step 1 of Example 65 in place of the compound of Step 1 of Example 54 to thus obtain the title compound without purification.

Yield: 102 mg (0.348 mmol), percentage yield: 98%

$^1$H NMR (CDCl$_3$, 400 MHz) δ 3.46 (s, 3H), 4.71 (d, J=0.9 Hz, 2H), 7.35 (dd, J=9.7, 6.4 Hz, 1H), 7.40-7.43 (m, 1H).

Step 2 Synthesis of Compound of Example 74

An operation similar to that in Step 2 of Example 15 was performed using the compound (44.0 mg, 0.150 mmol) of Step 1 in place of 7-bromo-4,5-difluoro-1-benzofuran to thus obtain the title compound.

Yield: 38.5 mg (0.0716 mmol), percentage yield: 48%

MS (ESI, m/z) 538 [M+H]$^+$ $^1$H NMR (DMSO-d$_6$, 400 MHz) δ 1.75-2.01 (m, 3H), 2.21-2.31 (m, 1H), 3.33 (s, 3H), 3.42-3.62 (m, 2H), 4.33-4.45 (m, 1H), 4.72 (s, 2H), 5.19-5.29 (m, 2H), 7.16-7.23 (m, 2H), 7.32-7.69 (m, 8H), 12.54 (br s, 1H).

Example 75

1-{3-[(4-{2-[(dimethylamino)methyl]-4,5-difluoro-1-benzothien-7-yl}phenoxy)methyl]benzoyl}-L-proline trifluoroacetic acid salt Step 1 Synthesis of [(7-bromo-4,5-difluoro-1-benzothien-2-yl)methyl]dimethylamine Acetonitrile (1 mL) was added to a solution (0.5 mL) of 2.0 M dimethylamine in THF, and a solution (2 mL) of the compound (121 mg, 0.354 mmol) of Step 1 of Example 65 in acetonitrile was added dropwise under ice-cooling, and stirred at room temperature overnight. The solvent was distilled away under reduced pressure. The resulting residue was diluted with ethyl acetate, washed with a saturated aqueous sodium hydrogen carbonate solution, and then dried over anhydrous sodium sulfate. The solvent was distilled away under reduced pressure to thus obtain the title compound.

Yield: 109 mg (0.356 mmol), percentage yield: quantitative

MS (ESI, m/z) 307 [M+H]$^+$ $^1$H NMR (CDCl$_3$, 400 MHz) δ 2.35 (s, 6H), 3.72 (s, 2H), 7.30-7.36 (m, 2H).

Step 2 Synthesis of Compound of Example 75

An operation similar to that in Step 2 of Example 15 was performed using the compound (45.9 mg, 0.150 mmol) of Step 1 in place of 7-bromo-4,5-difluoro-1-benzofuran to thus obtain the title compound.

Yield: 41.2 mg (0.0620 mmol), percentage yield: 41%

MS (ESI, m/z) 551 [M+H]$^+$ $^1$H NMR (DMSO-d$_6$, 400 MHz) δ 1.75-2.32 (m, 4H), 2.81 (s, 6H), 3.39-3.63 (m, 2H), 4.32-4.46 (m, 1H), 4.66 (s, 2H), 5.20-5.31 (m, 2H), 7.19-7.25 (m, 2H), 7.33-7.71 (m, 7H), 7.84 (s, 1H), 10.02 (br s, 1H), 12.53 (br s, 1H).

Tables 1-1 to 1-5 show structural formulas of the compounds obtained in Examples described above.

TABLES 1-1 to 1-5 compound of Ex. 1

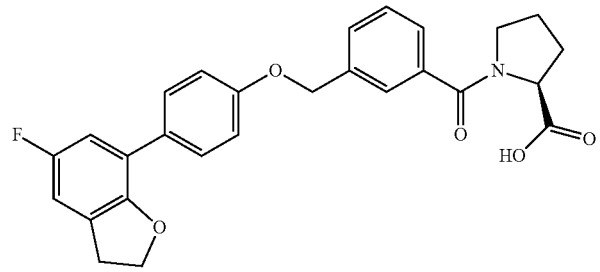 [SMILES: O=C(O)[C@@H]1CCCN1C(=O)c1cccc(COc2ccc(-c3cc(F)cc4c3OCC4)cc2)c1]

compound of Ex. 2

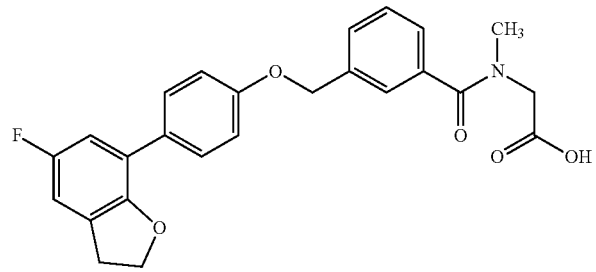 [SMILES: CN(CC(=O)O)C(=O)c1cccc(COc2ccc(-c3cc(F)cc4c3OCC4)cc2)c1]

compound of Ex. 3

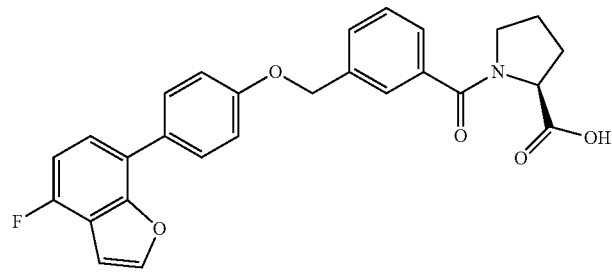 [SMILES: O=C(O)[C@@H]1CCCN1C(=O)c1cccc(COc2ccc(-c3ccc(F)c4ccoc34)cc2)c1]

compound of Ex. 4

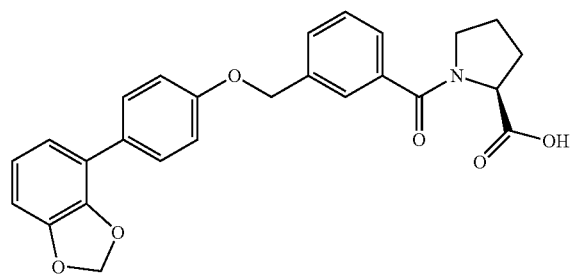 [SMILES: O=C(O)[C@@H]1CCCN1C(=O)c1cccc(COc2ccc(-c3cccc4c3OCO4)cc2)c1]

TABLES 1-1 to1-5-continued
compound of Ex. 5
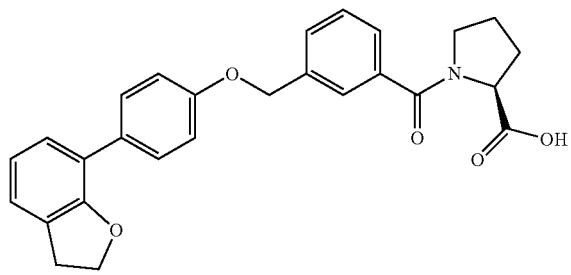
compound of Ex. 6
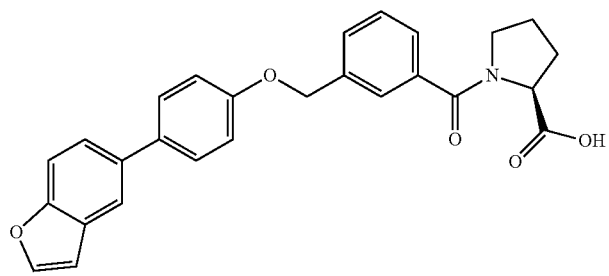 [SMILES: O=C(O)[C@@H]1CCCN1C(=O)c1cccc(COc2ccc(-c3ccc4occc4c3)cc2)c1]
compound of Ex. 7
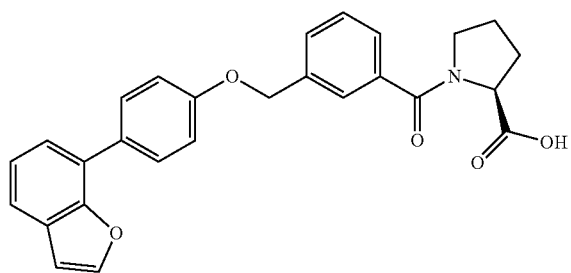
compound of Ex. 8
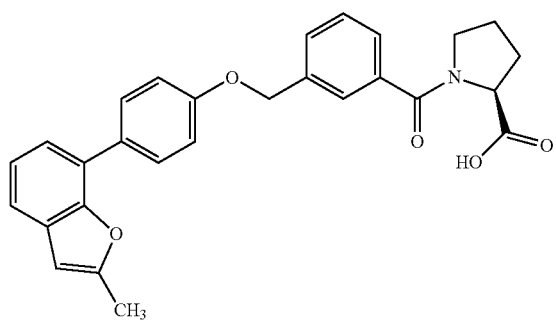 [SMILES: Cc1cc2cccc(-c3ccc(OCc4cccc(C(=O)N5CCC[C@H]5C(=O)O)c4)cc3)c2o1]
compound of Ex. 9
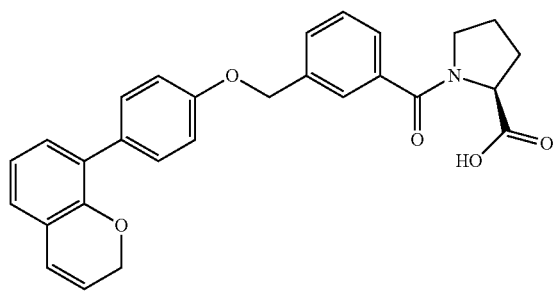 [SMILES: O=C(O)[C@@H]1CCCN1C(=O)c1cccc(COc2ccc(-c3cccc4c3OCC=C4)cc2)c1]

TABLES 1-1 to1-5-continued
compound of Ex. 10
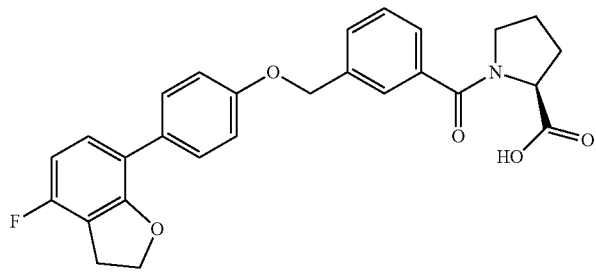 [SMILES: O=C(O)[C@@H]1CCCN1C(=O)c1cccc(COc2ccc(-c3ccc(F)c4c3OCC4)cc2)c1]
compound of Ex. 11
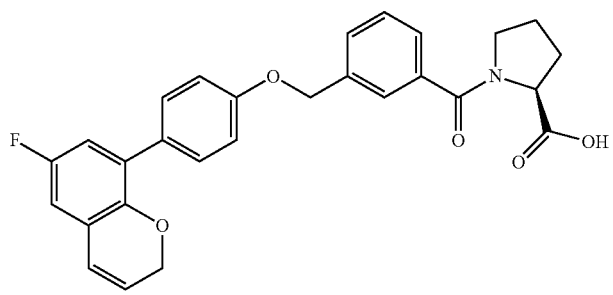 [SMILES: O=C(O)[C@@H]1CCCN1C(=O)c1cccc(COc2ccc(-c3cc(F)cc4c3OCC=C4)cc2)c1]
compound of Ex. 12
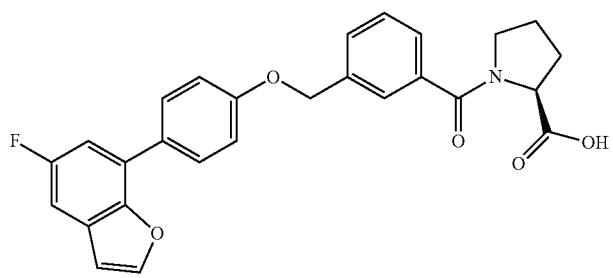 [SMILES: O=C(O)[C@@H]1CCCN1C(=O)c1cccc(COc2ccc(-c3cc(F)cc4ccoc34)cc2)c1]
compound of Ex. 13
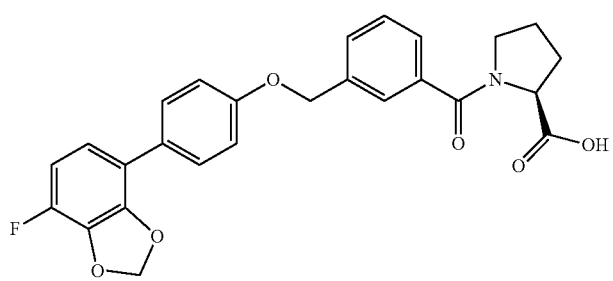 [SMILES: O=C(O)[C@@H]1CCCN1C(=O)c1cccc(COc2ccc(-c3ccc(F)c4c3OCO4)cc2)c1]
compound of Ex. 14
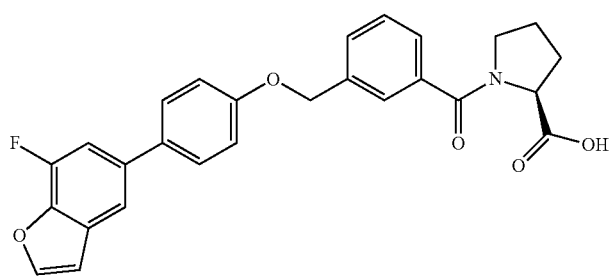 [SMILES: O=C(O)[C@@H]1CCCN1C(=O)c1cccc(COc2ccc(-c3cc(F)c4occc4c3)cc2)c1]

TABLES 1-1 to1-5-continued
compound of Ex. 15
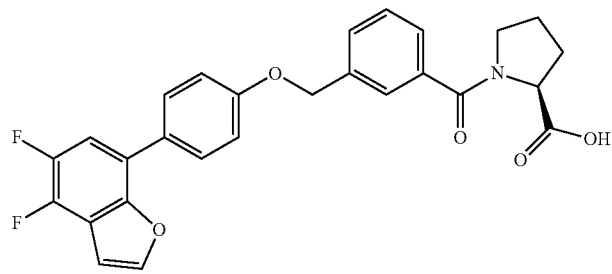 [SMILES: O=C(O)[C@@H]1CCCN1C(=O)c1cccc(COc2ccc(-c3cc(F)c(F)c4ccoc34)cc2)c1]
compound of Ex. 16
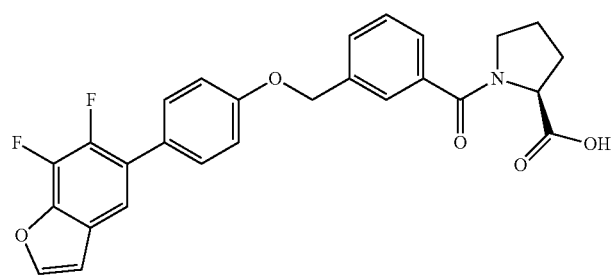 [SMILES: O=C(O)[C@@H]1CCCN1C(=O)c1cccc(COc2ccc(-c3cc4ccoc4c(F)c3F)cc2)c1]
compound of Ex. 17
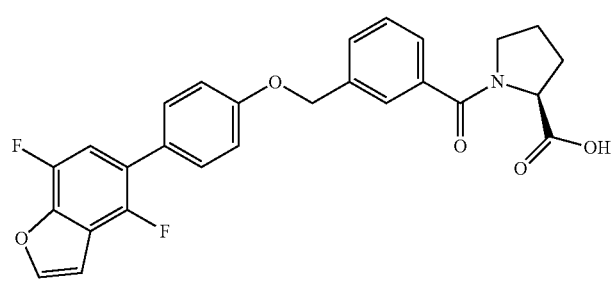 [SMILES: O=C(O)[C@@H]1CCCN1C(=O)c1cccc(COc2ccc(-c3cc(F)c4occc4c3F)cc2)c1]
compound of Ex. 18
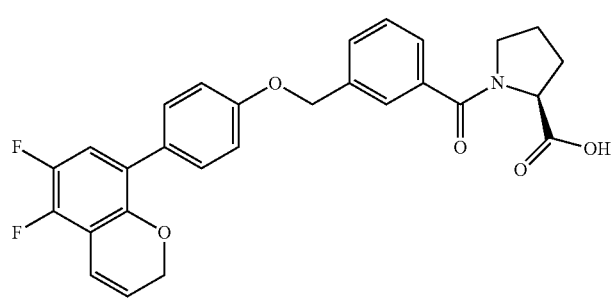 [SMILES: O=C(O)[C@@H]1CCCN1C(=O)c1cccc(COc2ccc(-c3cc(F)c(F)c4c3OCC=C4)cc2)c1]
compound of Ex. 19
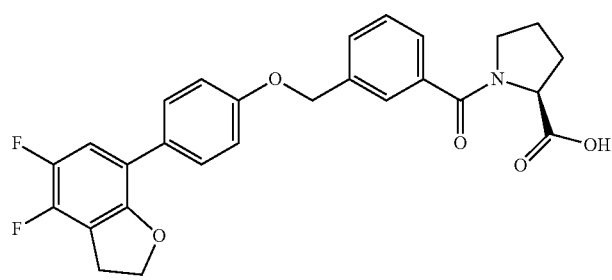 [SMILES: O=C(O)[C@@H]1CCCN1C(=O)c1cccc(COc2ccc(-c3cc(F)c(F)c4c3OCC4)cc2)c1]

TABLES 1-1 to 1-5-continued
compound of Ex. 20
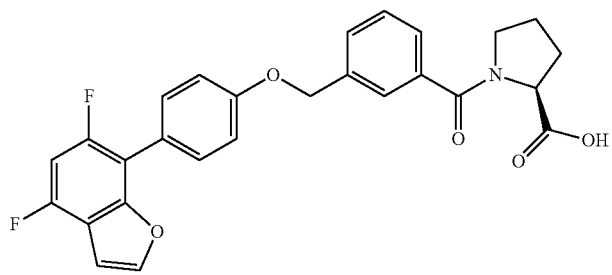 [SMILES: O=C(O)[C@@H]1CCCN1C(=O)c1cccc(COc2ccc(-c3c(F)cc(F)c4ccoc34)cc2)c1]
compound of Ex. 21
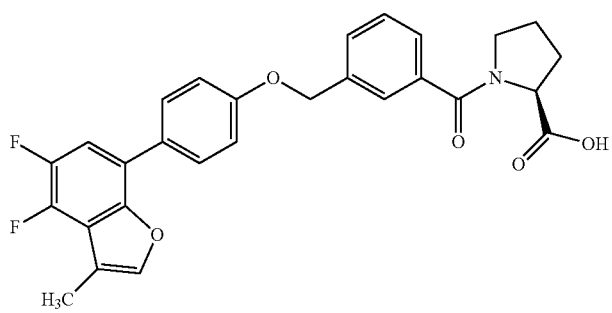 [SMILES: Cc1coc2c(-c3ccc(OCc4cccc(C(=O)N5CCC[C@H]5C(=O)O)c4)cc3)cc(F)c(F)c12]
compound of Ex. 22
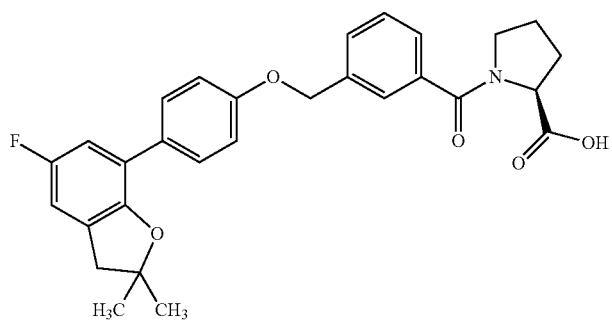 [SMILES: CC1(C)Cc2cc(F)cc(-c3ccc(OCc4cccc(C(=O)N5CCC[C@H]5C(=O)O)c4)cc3)c2O1]
compound of Ex. 23
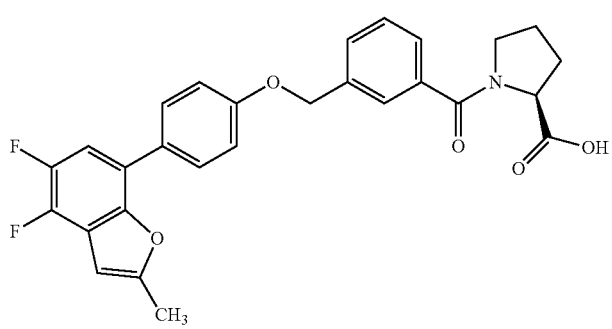 [SMILES: Cc1cc2c(F)c(F)cc(-c3ccc(OCc4cccc(C(=O)N5CCC[C@H]5C(=O)O)c4)cc3)c2o1]
compound of Ex. 24
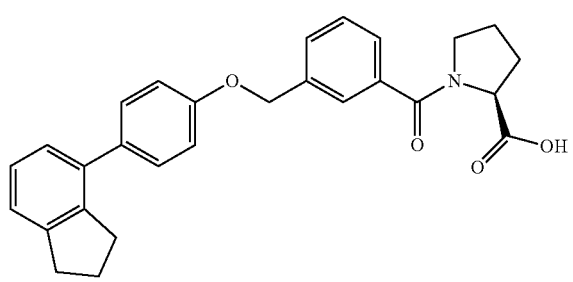

TABLES 1-1 to 1-5-continued
compound of Ex. 25
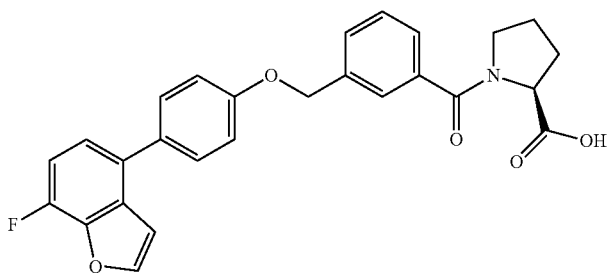 [SMILES: O=C(O)[C@@H]1CCCN1C(=O)c1cccc(COc2ccc(-c3ccc(F)c4occc34)cc2)c1]
compound of Ex. 26
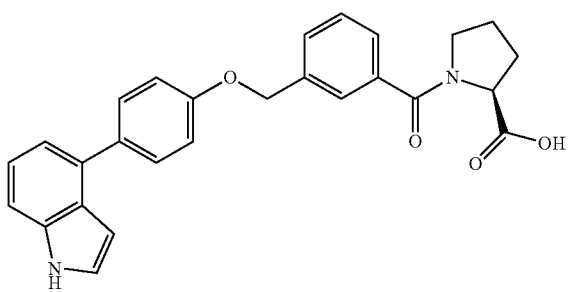 [SMILES: O=C(O)[C@@H]1CCCN1C(=O)c1cccc(COc2ccc(-c3cccc4[nH]ccc34)cc2)c1]
compound of Ex. 27
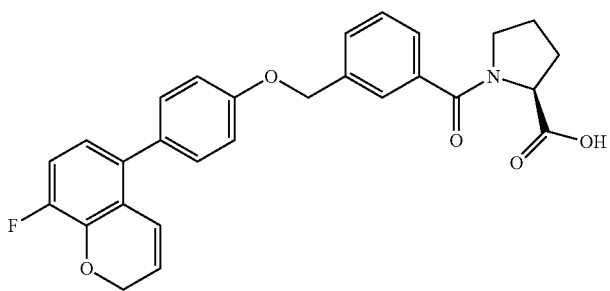 [SMILES: O=C(O)[C@@H]1CCCN1C(=O)c1cccc(COc2ccc(-c3ccc(F)c4c3C=CCO4)cc2)c1]
compound of Ex. 28
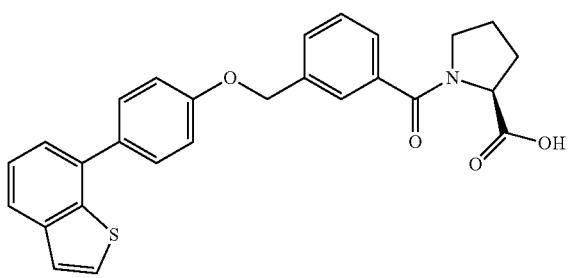 [SMILES: O=C(O)[C@@H]1CCCN1C(=O)c1cccc(COc2ccc(-c3cccc4ccsc34)cc2)c1]
compound of Ex. 29
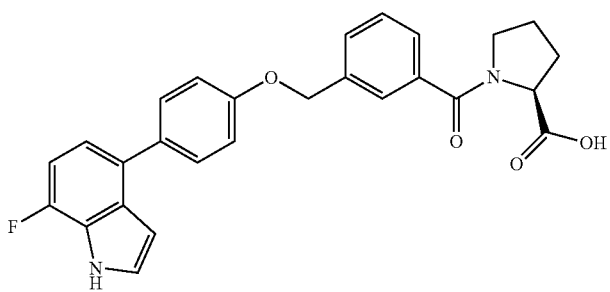 [SMILES: O=C(O)[C@@H]1CCCN1C(=O)c1cccc(COc2ccc(-c3ccc(F)c4[nH]ccc34)cc2)c1]

TABLES 1-1 to 1-5-continued
compound of Ex. 30
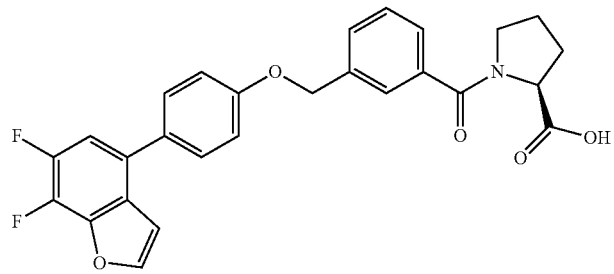 [SMILES: O=C(O)[C@@H]1CCCN1C(=O)c1cccc(COc2ccc(-c3cc(F)c(F)c4occc34)cc2)c1]
compound of Ex. 31
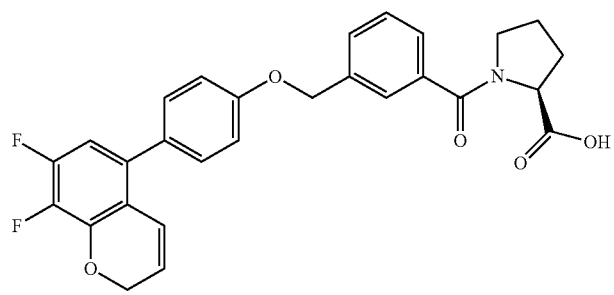 [SMILES: O=C(O)[C@@H]1CCCN1C(=O)c1cccc(COc2ccc(-c3cc(F)c(F)c4c3C=CCO4)cc2)c1]
compound of Ex. 32
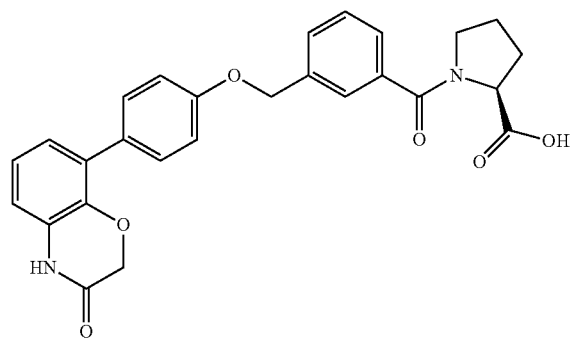 [SMILES: O=C1COc2c(cccc2-c2ccc(OCc3cccc(C(=O)N4CCC[C@H]4C(=O)O)c3)cc2)N1]
compound of Ex. 33
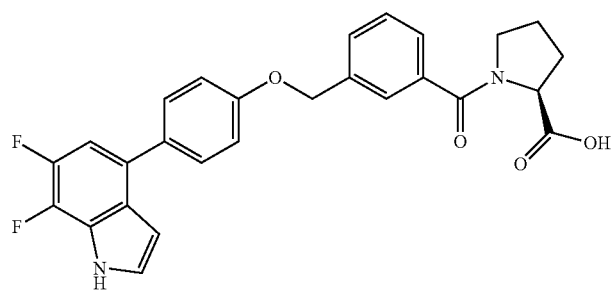 [SMILES: O=C(O)[C@@H]1CCCN1C(=O)c1cccc(COc2ccc(-c3cc(F)c(F)c4[nH]ccc34)cc2)c1]
compound of Ex. 34
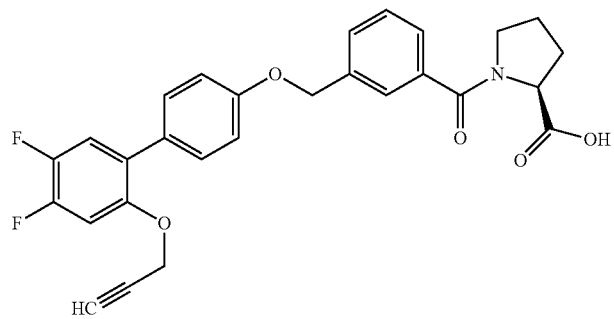 [SMILES: C#CCOc1cc(F)c(F)cc1-c1ccc(OCc2cccc(C(=O)N3CCC[C@H]3C(=O)O)c2)cc1]

TABLES 1-1 to 1-5-continued
compound of Ex. 35
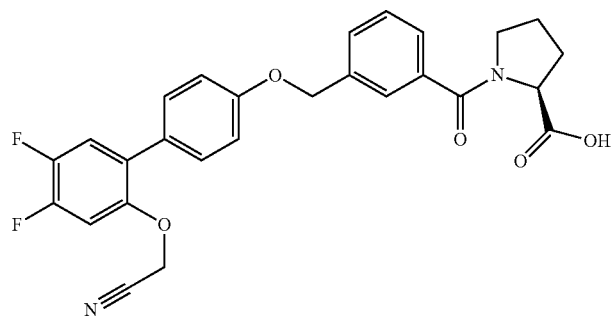 [SMILES: N#CCOc1cc(F)c(F)cc1-c1ccc(OCc2cccc(C(=O)N3CCC[C@H]3C(=O)O)c2)cc1]
compound of Ex. 36
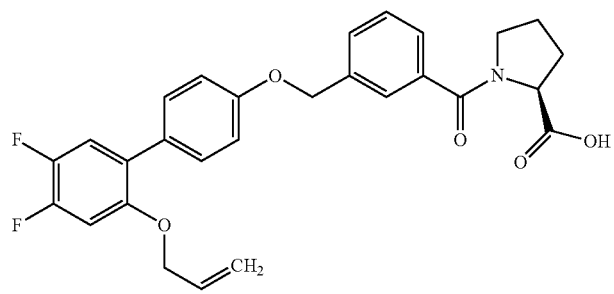 [SMILES: C=CCOc1cc(F)c(F)cc1-c1ccc(OCc2cccc(C(=O)N3CCC[C@H]3C(=O)O)c2)cc1]
compound of Ex. 37
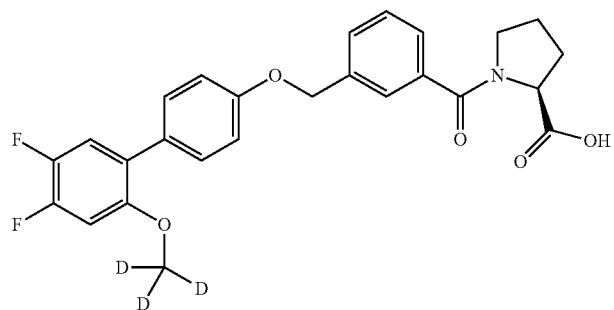 [SMILES: [2H]C([2H])([2H])Oc1cc(F)c(F)cc1-c1ccc(OCc2cccc(C(=O)N3CCC[C@H]3C(=O)O)c2)cc1]
compound of Ex. 38
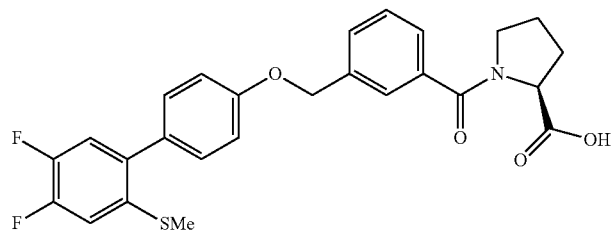 [SMILES: CSc1cc(F)c(F)cc1-c1ccc(OCc2cccc(C(=O)N3CCC[C@H]3C(=O)O)c2)cc1]
compound of Ex. 39
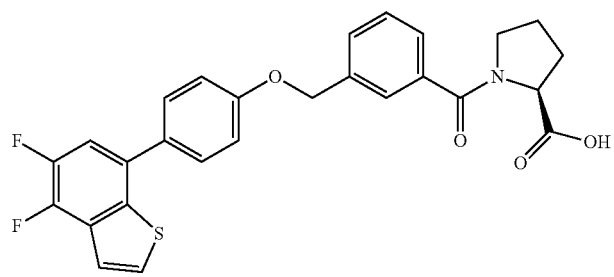

TABLES 1-1 to 1-5-continued
compound of Ex. 40
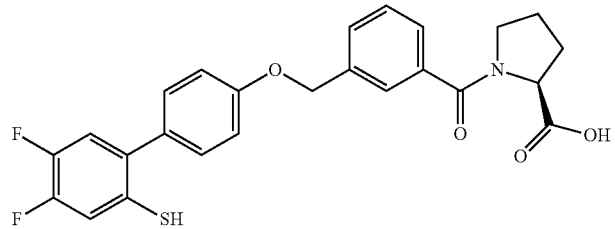 [SMILES: O=C(O)[C@@H]1CCCN1C(=O)c1cccc(COc2ccc(-c3cc(F)c(F)cc3S)cc2)c1]
compound of Ex. 41
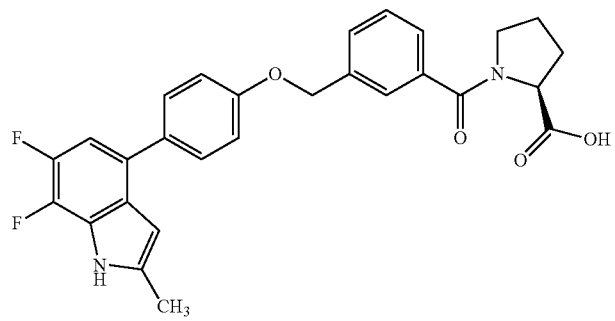 [SMILES: Cc1cc2c(-c3ccc(OCc4cccc(C(=O)N5CCC[C@H]5C(=O)O)c4)cc3)cc(F)c(F)c2[nH]1]
compound of Ex. 42
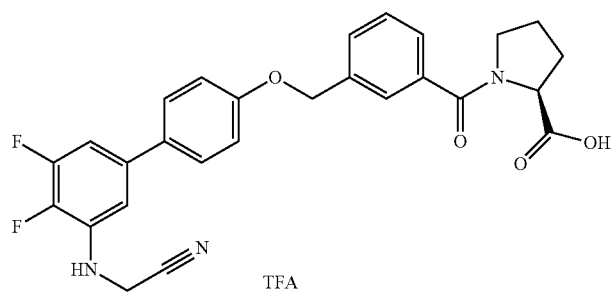 [SMILES: N#CCNc1cc(-c2ccc(OCc3cccc(C(=O)N4CCC[C@H]4C(=O)O)c3)cc2)cc(F)c1F]
compound of Ex. 43
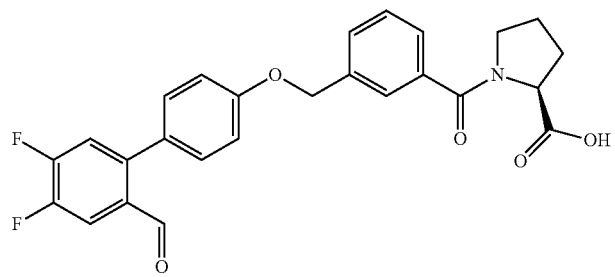 [SMILES: O=Cc1cc(F)c(F)cc1-c1ccc(OCc2cccc(C(=O)N3CCC[C@H]3C(=O)O)c2)cc1]
compound of Ex. 44
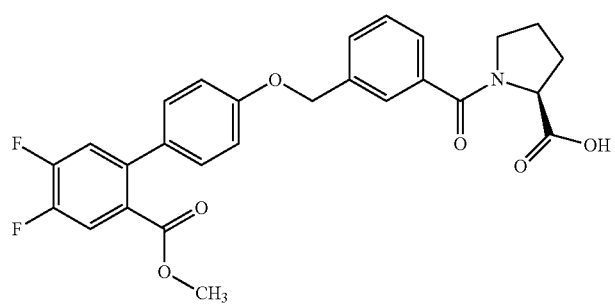 [SMILES: COC(=O)c1cc(F)c(F)cc1-c1ccc(OCc2cccc(C(=O)N3CCC[C@H]3C(=O)O)c2)cc1]

TABLES 1-1 to1-5-continued
compound of Ex. 45
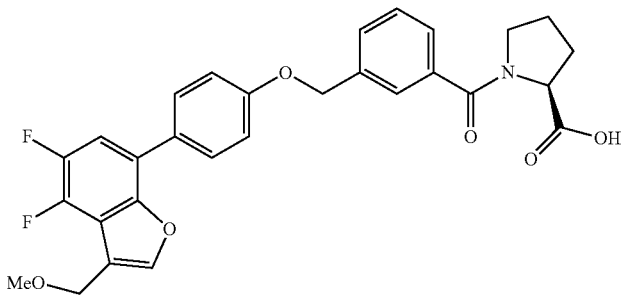 [SMILES: COCc1coc2c(-c3ccc(OCc4cccc(C(=O)N5CCC[C@H]5C(=O)O)c4)cc3)cc(F)c(F)c12]
compound of Ex. 46
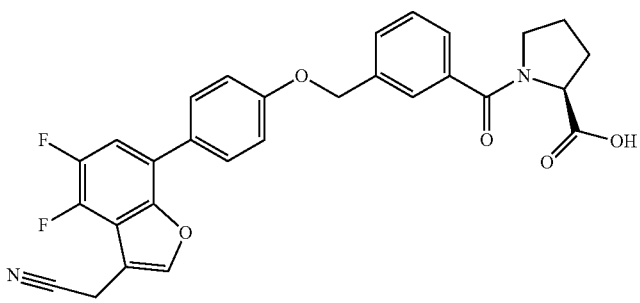 [SMILES: N#CCc1coc2c(-c3ccc(OCc4cccc(C(=O)N5CCC[C@H]5C(=O)O)c4)cc3)cc(F)c(F)c12]
compound of Ex. 47
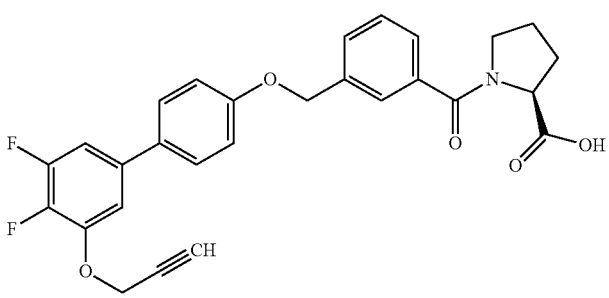 [SMILES: C#CCOc1cc(-c2ccc(OCc3cccc(C(=O)N4CCC[C@H]4C(=O)O)c3)cc2)cc(F)c1F]
compound of Ex. 48
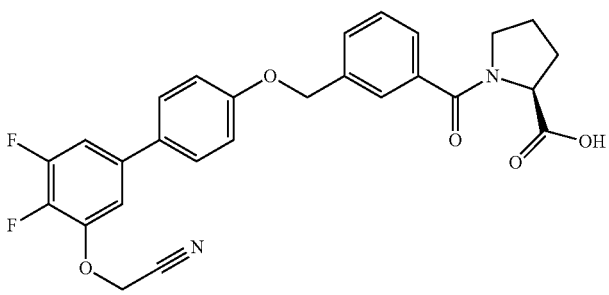 [SMILES: N#CCOc1cc(-c2ccc(OCc3cccc(C(=O)N4CCC[C@H]4C(=O)O)c3)cc2)cc(F)c1F]
compound of Ex. 49
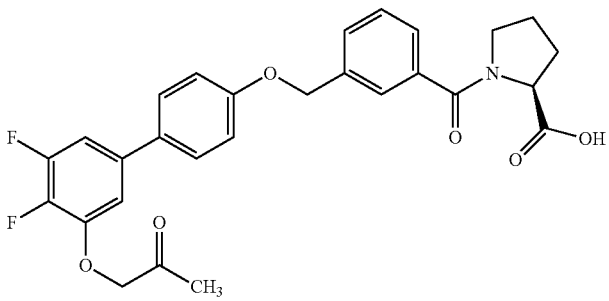 [SMILES: CC(=O)COc1cc(-c2ccc(OCc3cccc(C(=O)N4CCC[C@H]4C(=O)O)c3)cc2)cc(F)c1F]

TABLES 1-1 to1-5-continued
compound of Ex. 50
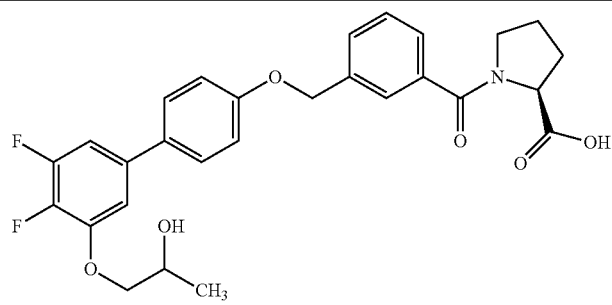
compound of Ex. 51
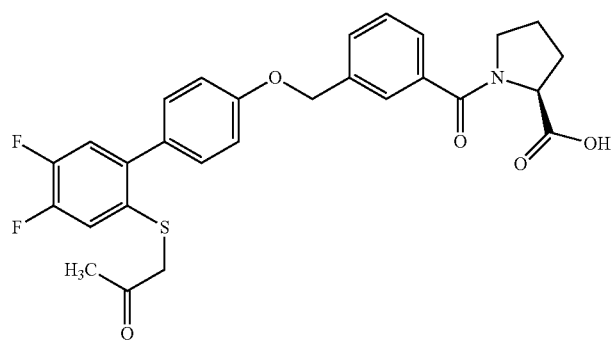 [SMILES: CC(=O)CSc1cc(F)c(F)cc1-c1ccc(OCc2cccc(C(=O)N3CCC[C@H]3C(=O)O)c2)cc1]
compound of Ex. 52
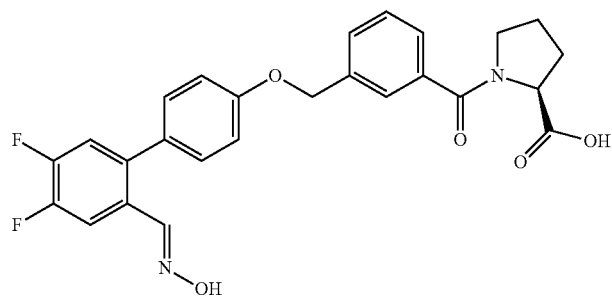 [SMILES: O=C(O)[C@@H]1CCCN1C(=O)c1cccc(COc2ccc(-c3cc(F)c(F)cc3/C=N/O)cc2)c1]
compound of Ex. 53
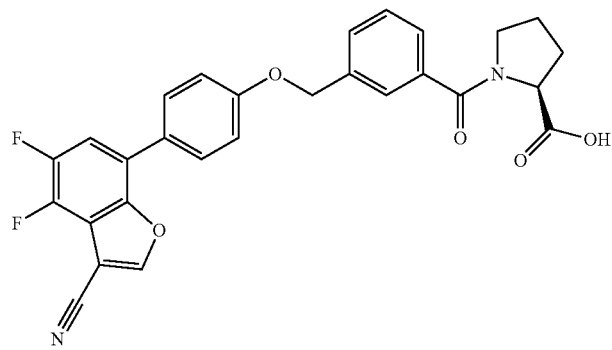 [SMILES: N#Cc1coc2c(-c3ccc(OCc4cccc(C(=O)N5CCC[C@H]5C(=O)O)c4)cc3)cc(F)c(F)c12]
compound of Ex. 54
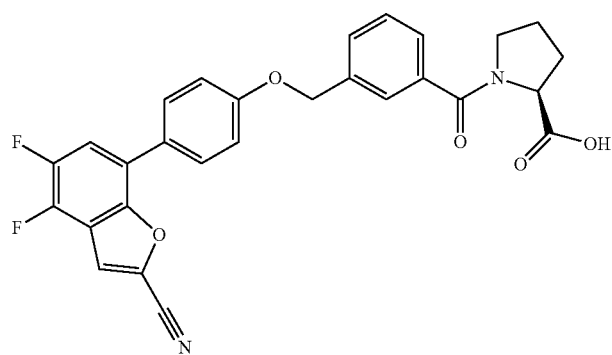 [SMILES: N#Cc1cc2c(F)c(F)cc(-c3ccc(OCc4cccc(C(=O)N5CCC[C@H]5C(=O)O)c4)cc3)c2o1]

TABLES 1-1 to1-5-continued
compound of Ex. 55
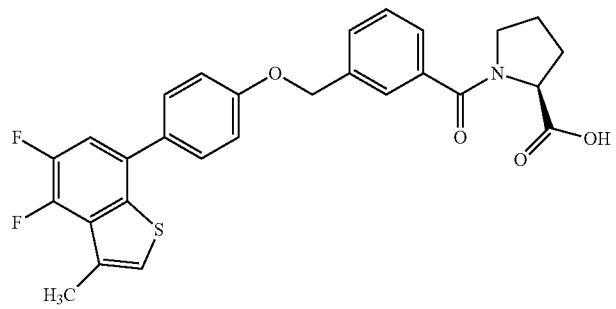
compound of Ex. 56
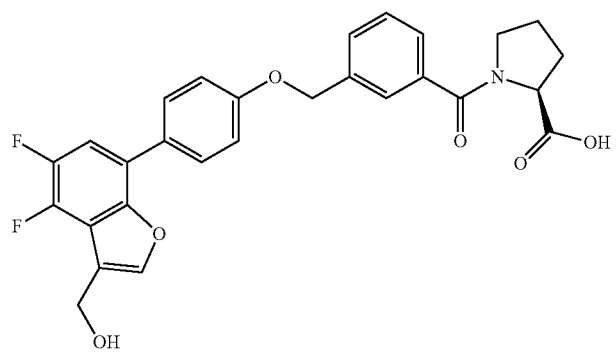 [SMILES: O=C(O)[C@@H]1CCCN1C(=O)c1cccc(COc2ccc(-c3cc(F)c(F)c4c(CO)coc34)cc2)c1]
compound of Ex. 57
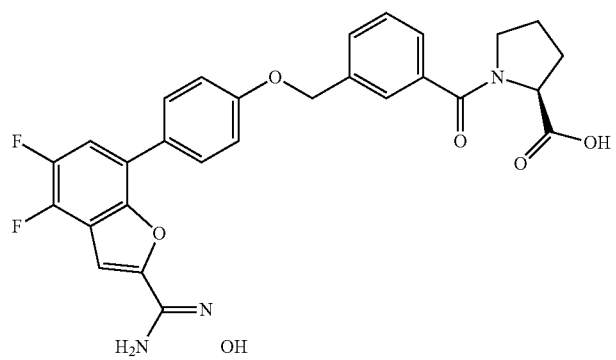
compound of Ex. 58
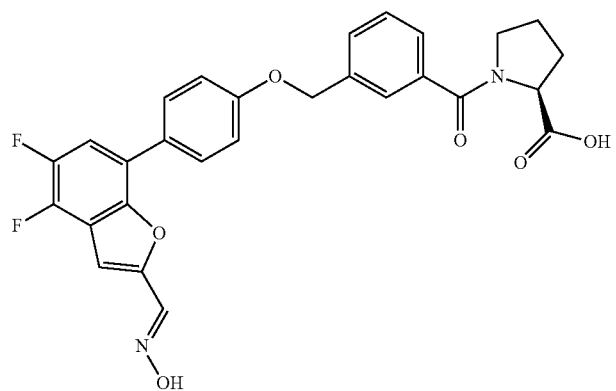 [SMILES: O=C(O)[C@@H]1CCCN1C(=O)c1cccc(COc2ccc(-c3cc(F)c(F)c4cc(/C=N/O)oc34)cc2)c1]

TABLES 1-1 to 1-5-continued
compound of Ex. 59
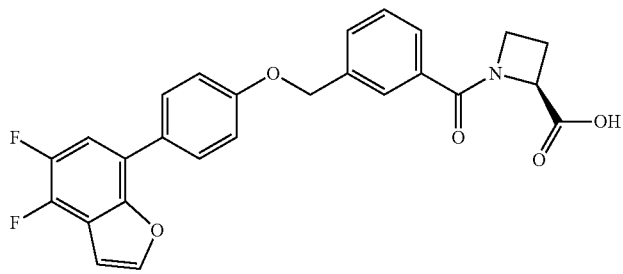 [SMILES: O=C(O)[C@@H]1CCN1C(=O)c1cccc(COc2ccc(-c3cc(F)c(F)c4ccoc34)cc2)c1]
compound of Ex. 60
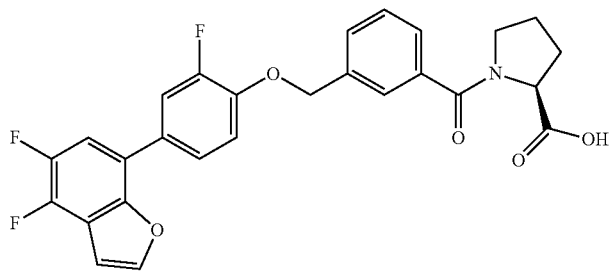 [SMILES: O=C(O)[C@@H]1CCCN1C(=O)c1cccc(COc2ccc(-c3cc(F)c(F)c4ccoc34)cc2F)c1]
compound of Ex. 61
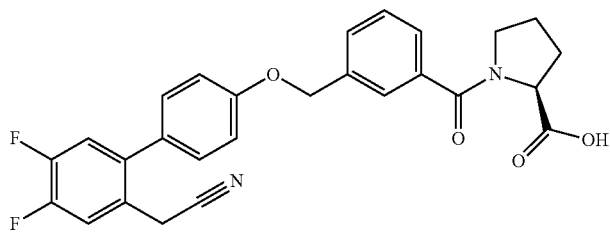 [SMILES: N#CCc1cc(F)c(F)cc1-c1ccc(OCc2cccc(C(=O)N3CCC[C@H]3C(=O)O)c2)cc1]
compound of Ex. 62
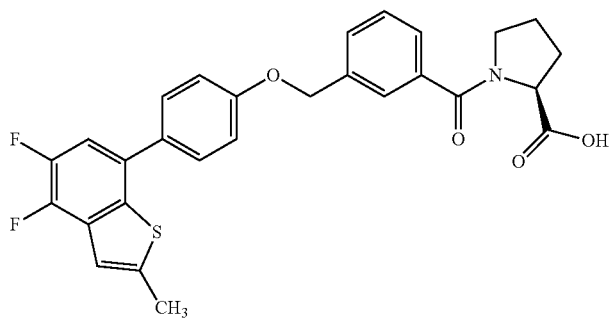
compound of Ex. 63
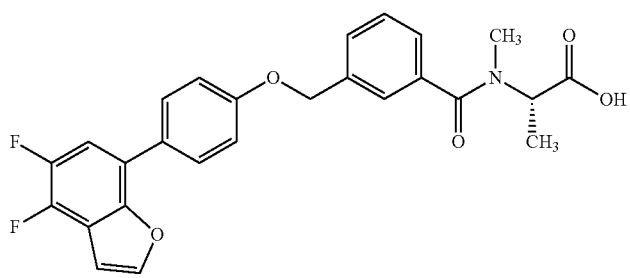 [SMILES: C[C@@H](C(=O)O)N(C)C(=O)c1cccc(COc2ccc(-c3cc(F)c(F)c4ccoc34)cc2)c1]

TABLES 1-1 to 1-5-continued
compound of Ex. 64
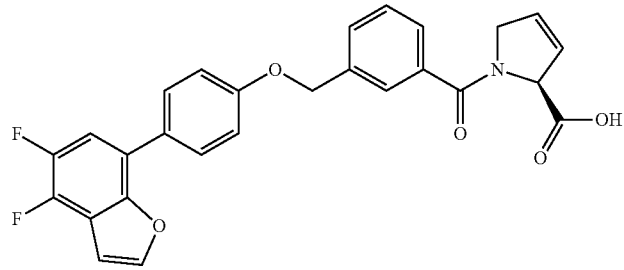 [SMILES: O=C(O)[C@@H]1C=CCN1C(=O)c1cccc(COc2ccc(-c3cc(F)c(F)c4ccoc34)cc2)c1]
compound of Ex. 65
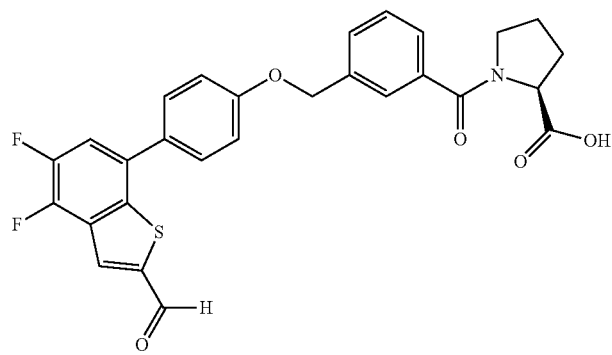 [SMILES: O=Cc1cc2c(F)c(F)cc(-c3ccc(OCc4cccc(C(=O)N5CCC[C@H]5C(=O)O)c4)cc3)c2s1]
compound of Ex. 66
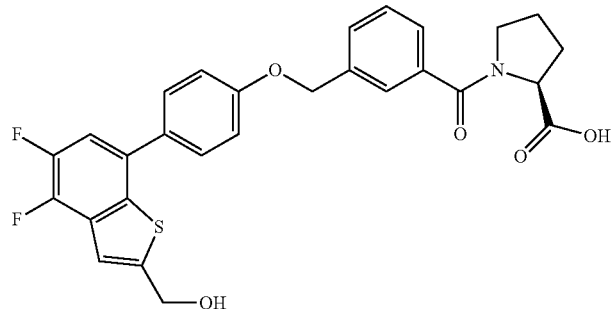 [SMILES: O=C(O)[C@@H]1CCCN1C(=O)c1cccc(COc2ccc(-c3cc(F)c(F)c4cc(CO)sc34)cc2)c1]
compound of Ex. 67
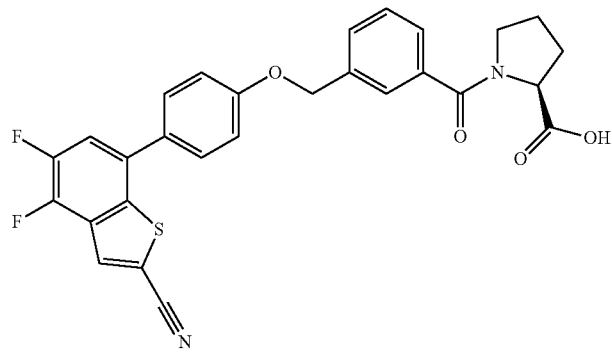 [SMILES: N#Cc1cc2c(F)c(F)cc(-c3ccc(OCc4cccc(C(=O)N5CCC[C@H]5C(=O)O)c4)cc3)c2s1]
compound of Ex. 68
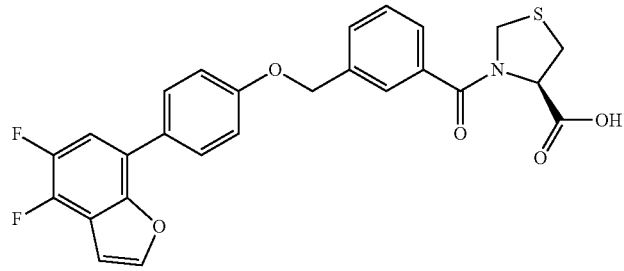 [SMILES: O=C(O)[C@@H]1CSCN1C(=O)c1cccc(COc2ccc(-c3cc(F)c(F)c4ccoc34)cc2)c1]

TABLES 1-1 to 1-5-continued
compound of Ex. 69
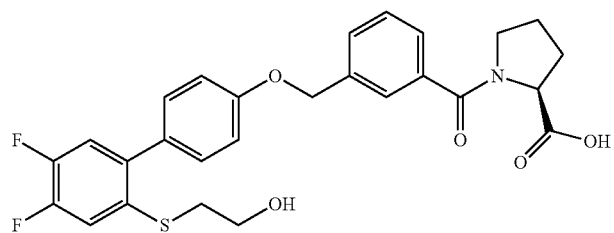 [SMILES: O=C(O)[C@@H]1CCCN1C(=O)c1cccc(COc2ccc(-c3cc(F)c(F)cc3SCCO)cc2)c1]
compound of Ex. 70
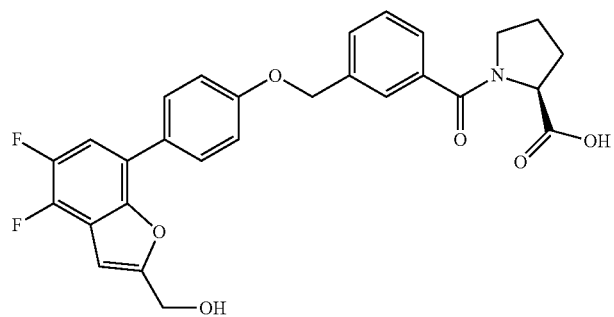 [SMILES: O=C(O)[C@@H]1CCCN1C(=O)c1cccc(COc2ccc(-c3cc(F)c(F)c4cc(CO)oc34)cc2)c1]
compound of Ex. 71
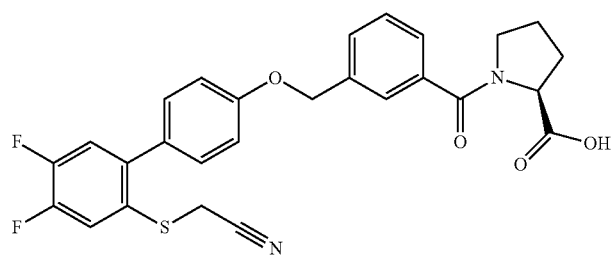 [SMILES: N#CCSc1cc(F)c(F)cc1-c1ccc(OCc2cccc(C(=O)N3CCC[C@H]3C(=O)O)c2)cc1]
compound of Ex. 72
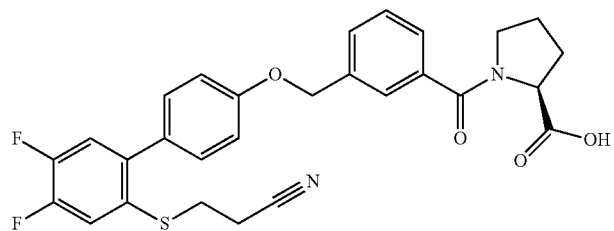 [SMILES: N#CCCSc1cc(F)c(F)cc1-c1ccc(OCc2cccc(C(=O)N3CCC[C@H]3C(=O)O)c2)cc1]
compound of Ex. 73
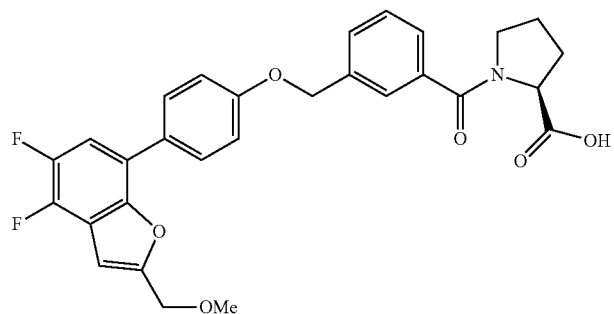 [SMILES: COCc1cc2c(F)c(F)cc(-c3ccc(OCc4cccc(C(=O)N5CCC[C@H]5C(=O)O)c4)cc3)c2o1]

TABLES 1-1 to 1-5-continued compound of Ex. 74

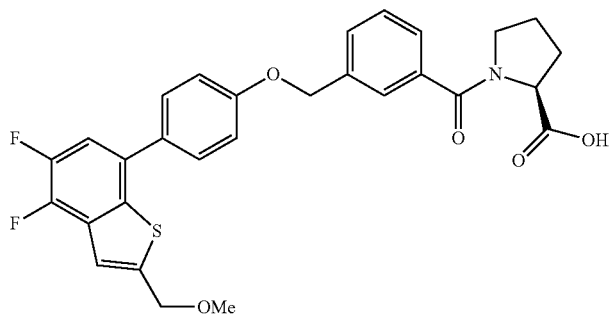 [SMILES: COCc1cc2c(F)c(F)cc(-c3ccc(OCc4cccc(C(=O)N5CCC[C@H]5C(=O)O)c4)cc3)c2s1]

compound of Ex. 75

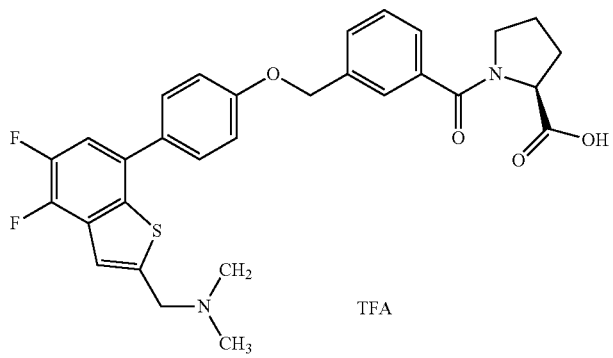 [SMILES: CN(C)Cc1cc2c(F)c(F)cc(-c3ccc(OCc4cccc(C(=O)N5CCC[C@H]5C(=O)O)c4)cc3)c2s1]

TFA

Test Example 1

Measurement of Glycogen Synthase Activity

A human GYS1 expression plasmid (pCDNA3.1(+)-hGYS1) was constructed by the following method. Using a human skeletal muscle cDNA of Human MTC Panel I (Takara Bio Inc., 636742) as a template, a human GYS1 gene was amplified by a PCR method using cloning primers (Forward Primer: ATGCCTTTAAACCGCAC (SEQ ID NO: 1), Reverse Primer: TTAGTTACGCTCCTCGC (SEQ ID NO: 2)). Using the amplified human GYS1 sequence as a template, a restriction enzyme sequence was added by a PCR method using sub-cloning primers (Forward Primer: CCCTCGAGACCATGCCTTTAAACCGCACTT (SEQ ID NO: 3), Reverse Primer: GGTCTAGATTAGTTACGCTC-CTCGCCCAG (SEQ ID NO: 4)). Then, the human GYS1 gene was introduced between a Xho I site and a Xba I site of pCDNA3.1(+) (Invitrogen Corporation, V790-20).

Glycogen synthase was prepared by the following method according to the published article (THE JOURNAL OF BIOLOGICAL CHEMISTRY Vol. 269, No. 41, 25534-25542, 1994). Human kidney-derived HEK293T cells were seeded in a dish (Thermo Fisher Scientific Inc., 168381) using a 10% FBS-containing DMEM (Nacalai Tesque, Inc., 0845874) medium, and cultured overnight. Then, using Lipofectamine LTX (Invitrogen Corporation, 15338-100), the human GYS1 expression vector was transfected according to the attached manual. After culturing under conditions of 37° C. and 5% $CO_2$ for 2 days, the resultant was dissolved in a lysis buffer (50 mM Tris-HCl (pH 8.0), 10 mM EDTA, 2 mM EGTA, 100 mM NaF, 1 mM PMSF, 1 mM DTT, 1× Complete (Roche Diagnostics K. K., 1873580)), homogenized, and then centrifuged at 16000×g at 4° C. for 15 minutes. To the precipitated fraction, a lysis buffer was added. Re-dissolved fractions were used as glycogen synthase for evaluation.

The glycogen synthase activity was measured by the following method. To a polystyrene 96-well plate, a solution containing 30 mM glycylglycine (pH 7.3), 40 mM KCl, 20 mM $MgCl_2$, 9.2% DMSO containing one of the test compounds at various concentrations, and 10 mM glucose-6-phosphate (Sigma-Aldrich Corporation, G7879) was added by 12 μL/well.

Next, a substrate solution containing 30 mM glycylglycine (pH 7.3), 4.3 mg/mL of glycogen (Sigma-Aldrich Corporation, G8876), 21.6 mM UDP-glucose (Sigma-Aldrich Corporation, U4625), 21.6 mM phosphoenolpyruvic acid (Sigma-Aldrich Corporation, P0564), and 4.05 mM NADH (Sigma-Aldrich Corporation, N8129) was added by 18 μL/well.

Further, an enzyme solution containing 50 mM Tris-HCl (pH 8.0), 27 mM DTT (Nacalai Tesque, Inc., 14128-04), 0.2 mg/mL of bovine serum albumin, 0.17 mg/mL of the glycogen synthase, 1.5 μL of a pyruvate kinase/lactate dehydrogenase solution (Sigma-Aldrich Corporation, P0294) was added by 18 μL/well to prepare a reaction solution. After the reaction solution was incubated (at 30° C. for 25 minutes for Examples 1 to 10, at 37° C. for 20 minutes for Examples 11 to 75), the absorbance at 340 nm was measured using Benchmark Plus (Bio-Rad Laboratories, Inc.).

The activities of the test compounds were calculated by the following method. The change in the absorbance (ΔA340) was calculated by subtracting the absorbance at 340 nm of the reaction solution containing the compound and DMSO from the absorbance at 340 nm of a reaction solution not containing the compound but containing only DMSO. The ΔA340 of the reaction solution containing the compound of Example 1 in WO/2011/058154 at the final concentration of 10 μM was taken as 100% to calculate the relative activity (%) of the test compounds at various concentrations. EC50 representing the concentration of the compound which induces an increase in the relative activity to 50% was calculated using XLfit (idbs). Tables 2-1 and 2-2 show the result.

TABLE 2-1

| | EC50 (μM) |
|---|---|
| compound of Ex. 1 | 0.26 |
| compound of Ex. 2 | 0.59 |
| compound of Ex. 3 | 0.11 |
| compound of Ex. 4 | 0.25 |
| compound of Ex. 5 | 0.50 |
| compound of Ex. 6 | 0.33 |
| compound of Ex. 7 | 0.26 |
| compound of Ex. 8 | 0.82 |
| compound of Ex. 9 | 0.32 |
| compound of Ex. 10 | 0.35 |
| compound of Ex. 11 | 0.78 |
| compound of Ex. 12 | 0.35 |
| compound of Ex. 13 | 0.27 |
| compound of Ex. 14 | 0.07 |
| compound of Ex. 15 | 0.022 |
| compound of Ex. 16 | 0.035 |
| compound of Ex. 17 | 0.27 |
| compound of Ex. 18 | 0.10 |
| compound of Ex. 19 | 0.031 |
| compound of Ex. 20 | 0.064 |
| compound of Ex. 21 | 0.054 |
| compound of Ex. 22 | 0.18 |
| compound of Ex. 23 | 0.11 |
| compound of Ex. 24 | 0.67 |
| compound of Ex. 25 | 0.40 |
| compound of Ex. 26 | 0.16 |
| compound of Ex. 27 | 0.21 |
| compound of Ex. 28 | 0.89 |
| compound of Ex. 29 | 0.23 |
| compound of Ex. 30 | 0.14 |
| compound of Ex. 31 | 0.10 |
| compound of Ex. 32 | 0.75 |
| compound of Ex. 33 | 0.034 |
| compound of Ex. 34 | 0.017 |
| compound of Ex. 35 | 0.015 |
| compound of Ex. 36 | 0.11 |
| compound of Ex. 37 | 0.010 |
| compound of Ex. 38 | 0.029 |
| compound of Ex. 39 | 0.042 |
| compound of Ex. 40 | 0.11 |
| compound of Ex. 41 | 0.10 |
| compound of Ex. 42 | 0.054 |
| compound of Ex. 43 | 0.070 |
| compound of Ex. 44 | 0.81 |
| compound of Ex. 45 | 0.80 |
| compound of Ex. 46 | 0.15 |
| compound of Ex. 47 | 0.15 |
| compound of Ex. 48 | 0.12 |
| compound of Ex. 49 | 0.22 |
| compound of Ex. 50 | 0.41 |
| compound of Ex. 51 | 0.083 |
| compound of Ex. 52 | 0.061 |
| compound of Ex. 53 | 0.61 |
| compound of Ex. 54 | 0.26 |
| compound of Ex. 55 | 0.085 |
| compound of Ex. 56 | 0.044 |
| compound of Ex. 57 | 0.14 |
| compound of Ex. 58 | 0.045 |
| compound of Ex. 59 | 0.15 |
| compound of Ex. 60 | 0.16 |

TABLE 2-2

| | EC50 (μM) |
|---|---|
| compound of Ex. 61 | 0.79 |
| compound of Ex. 62 | 0.27 |
| compound of Ex. 63 | 0.22 |
| compound of Ex. 64 | 0.14 |
| compound of Ex. 65 | 0.30 |
| compound of Ex. 66 | 0.074 |
| compound of Ex. 67 | 0.59 |
| compound of Ex. 68 | 0.34 |
| compound of Ex. 69 | 0.13 |
| compound of Ex. 70 | 0.20 |
| compound of Ex. 71 | 0.038 |
| compound of Ex. 72 | 0.19 |
| compound of Ex. 73 | 0.065 |
| compound of Ex. 74 | 0.20 |
| compound of Ex. 1 in WO/2011/058154 | 0.1~0.25 |

Test Example 2

Measurement of PPAR-α Activity

The PPAR-α activity was measured according to the published article (THE JOURNAL OF BIOLOGICAL CHEMISTRY Vol. 270, No. 22, 12953-12956, 1995).

Plasmids used for the PPAR-α activity measurement were constructed as follows. A luciferase expression plasmid (UASx5-TK-Luc) used was obtained by introducing a sequence, in which five yeast GAL4-binding sequences are linked in tandem, upstream of a thymidine kinase promoter of pTAL-Luc (Takara Bio Inc., 6252-1). A PPAR-α receptor expression plasmid (hGR-GAL4-hPPARα) used was obtained by introducing a human GR N-terminal region (1-76 aa), a yeast GAL4 DNA-binding region (1-147 aa), and a PPARα ligand-binding region (167-468 aa) between a Not I site and a Sal I site of pExchange-1 Core Vector (Invitrogen Corporation, 211176).

A reporter assay was conducted by the following method using *Cercopithecus aethiops* kidney-derived CV-1 cells. The CV-1 cells were seeded in a 96-well plate (Thermo Fisher Scientific Inc., 4938) at $2\times10^4$ cells/well using a 10% FBS-containing DMEM (Nacalai Tesque, Inc., 0845874) medium. After culturing under conditions of 37° C. and 5% $CO_2$ for 2 hours, the plasmids were transfected. Lipofectamine LTX (Invitrogen Corporation, 15338-100) was used for the transfection according to the attached manual. The plasmid solution was prepared by adding a mixture solution of the luciferase expression plasmid and the PPAR-α receptor expression plasmid to OPTI-MEM I (Invitrogen Corporation, 11058-021). After the transfection was conducted, the test compound was added, and cultured at 37° C. in the presence of 5% $CO_2$ for 18 to 20 hours. After the culturing was completed, the luciferase activity was measured with Luminescensor JNR (ATTO) using Bright-Glo (Promega Corporation, E2620).

The fold induction of PPAR-α by the test compounds was calculated by the following method. For the compounds of Examples 1, 4, 5, 7, and 9, PPAR-α relative fold induction (%) was defined as 100 (A/B), where A represents the maximum value of PPAR-α activities with the test compound at 0.3 μM, 1 μM, 3 μM, 10 μM, 30 μM, and 100 μM, and B represents the PPAR-α activity with the compound in WO/2011/058154 at 100 μM. For the compounds of Examples 11, 15, 19, 22, 26, and 32, PPAR-α relative fold induction (%) was defined as 100 (A/B), where A represents the maximum value of PPAR-α activities with the test compound at 3 μM, 10 μM, 30 μM, and 100 μM, and B represents the PPAR-α activity with the compound in WO/2011/058154 at 100 μM. Table 3 shows the result.

TABLE 3

| | PPARα relative fold induction (%) |
|---|---|
| compound of Ex. 1 | 10 |
| compound of Ex. 4 | 17 |
| compound of Ex. 5 | 10 |
| compound of Ex. 7 | 17 |
| compound of Ex. 9 | 11 |
| compound of Ex. 11 | 18 |
| compound of Ex. 15 | 20 |
| compound of Ex. 19 | 12 |
| compound of Ex. 22 | 15 |
| compound of Ex. 26 | 13 |
| compound of Ex. 32 | 3 |
| compound of Ex. 40 | 10 |
| compound of Ex. 42 | 13 |
| compound of Ex. 43 | 11 |
| compound of Ex. 44 | 10 |
| compound of Ex. 49 | 17 |
| compound of Ex. 50 | 15 |
| compound of Ex. 51 | 15 |
| compound of Ex. 52 | 18 |
| compound of Ex. 53 | 15 |
| compound of Ex. 56 | 6.4 |
| compound of Ex. 58 | 19 |
| compound of Ex. 61 | 10 |
| compound of Ex. 65 | 11 |
| compound of Ex. 66 | 18 |
| compound of Ex. 69 | 8.6 |
| compound of Ex. 70 | 7.9 |
| compound of Ex. 71 | 8.6 |
| compound of Ex. 72 | 15 |
| compound of Ex. 1 in WO/2011/058154 | 100 |

What is claimed is:

1. A compound of formula (I):

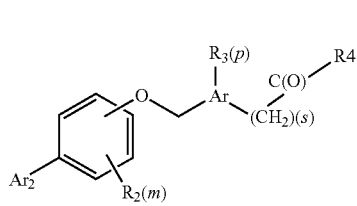

wherein Ar is an aromatic carbocyclic ring or a heterocyclic ring;

$Ar_2$ is represented by any one of the following rings

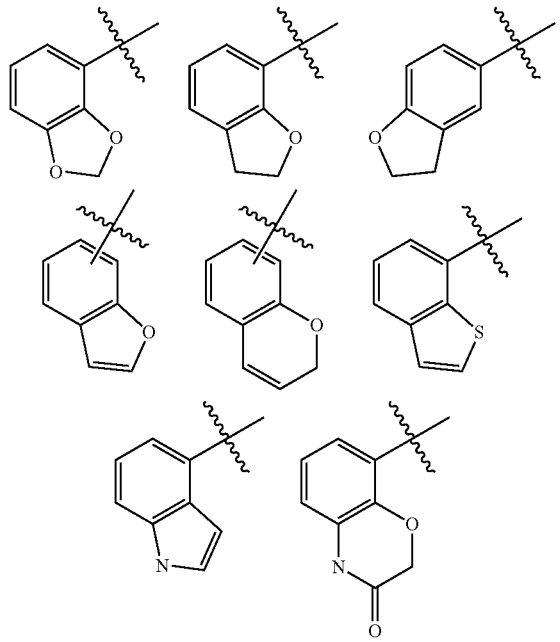

these rings may have a substituent, and the substituent is selected from the group consisting of acetamido, aminocarbonyl, benzyl, benzyloxy, a halogen, hydroxyl-lower alkyl, lower alkyl, lower alkoxy-lower alkyl, phenoxy, phenyl, a formyl group, a cyano group, a cyanoalkyl group, a hydroxyiminomethyl group, a hydroxyamidino group, an amino group, an aminoalkyl group, an alkylaminoalkyl group, a dialkylaminoalkyl group, lower alkoxy, and trifluoro-methoxy;

$R_2$ and $R_3$ are independently selected from the group consisting of lower alkyl, lower alkoxy, trifluoromethyl, a halogen, hydroxy, a hydroxyl-lower alkyl group, amino, alkylamino, dialkylamino, cyano, and nitro;

$R_4$ is an amino acid residue bonded to C(O) through a nitrogen atom of the amino acid;

m is 0, 1, 2, 3, or 4;

p is 0, 1, or 2; and s is 0, 1, or 2, or a pharmaceutically acceptable salt thereof.

2. A compound of formula (I):

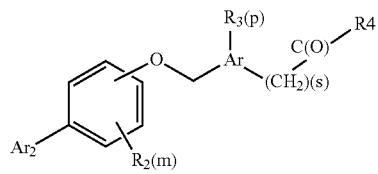

wherein Ar is an aromatic carbocyclic ring or a heterocyclic ring;

$Ar_2$ is represented by any one of the following rings

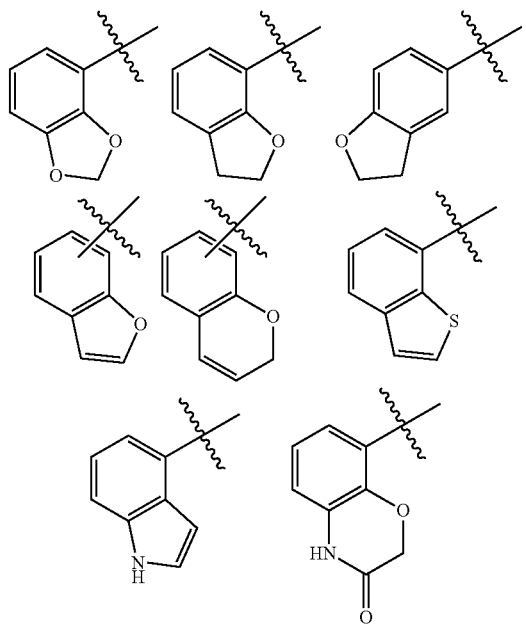

these rings may have a substituent, and the substituent is selected from the group consisting of acetamido, aminocarbonyl, benzyl, benzyloxy, a halogen, hydroxyl-lower alkyl, lower alkyl, lower alkoxy-lower alkyl, phenoxy, phenyl, lower alkoxy, and trifluoro-methoxy;

$R_2$ and $R_3$ are independently selected from the croup consisting of lower alkyl, lower alkoxy, trifluoromethyl, a halogen, hydroxy, amino, alkylamino, dialkylamino, cyano, and nitro;

$R_4$ is an amino acid residue bonded to C(O) through a nitrogen atom of the amino acid;

m is 0, 1, 2, 3, or 4;

p is 0, 1, or 2; and s is 0, 1, or 2, or a pharmaceutically acceptable salt thereof.

3. The compound according to claim 2, wherein $Ar_2$ in the formula (I) is represented by an one of the following rings

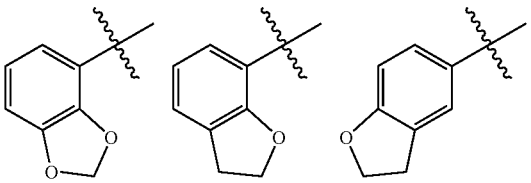

-continued

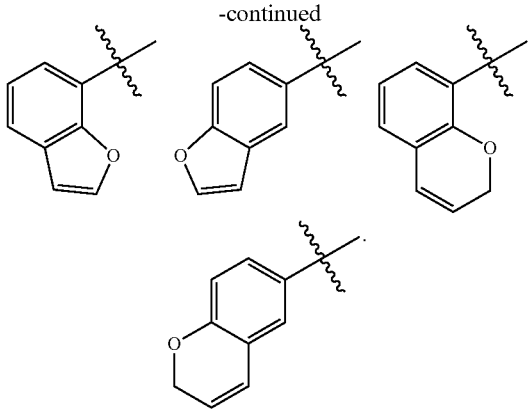

or a pharmaceutically acceptable salt thereof.

4. The compound according to claim 2, wherein in the formula (I),
Ar is a phenyl group, and
R$_4$ represents a proline residue bonded to C(O) through a nitrogen atom of the proline,
or a pharmaceutically acceptable salt thereof.

5. The compound according to claim 2, wherein in the formula (I),
Ar is a phenyl group,
R$_4$ represents a proline residue bonded to C(O) through a nitrogen atom of the proline, and
Ar$_2$ is represented by any one of the following rings which may have a substituent

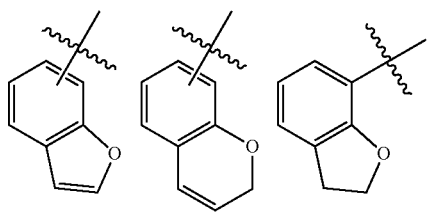

-continued

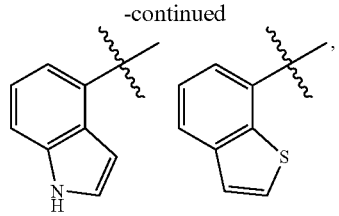

or a pharmaceutically acceptable salt thereof.

6. The compound according to claim 5, wherein the substituent Ar$_2$ in the formula (I) is a halogen,
or a pharmaceutically acceptable salt thereof.

7. The compound according to claim 6, wherein, in the formula (I), m=0, p=0, and s=0,
or a pharmaceutically acceptable salt thereof.

8. A pharmaceutical composition, comprising:
the compound according to claim 1 or a pharmaceutically acceptable salt thereof, and
a pharmaceutically acceptable carrier.

9. A pharmaceutical composition, comprising:
the compound according to claim 2 or a pharmaceutically acceptable salt thereof; and
a pharmaceutically acceptable carrier.

10. A method of treating diabetes by glycogen-synthase activation, comprising:
administering an effective amount of the compound according to claim 1 or a pharmaceutically acceptable salt thereof to a subject in need thereof.

11. A method of treating diabetes by a glycogen synthase activation, comprising:
administering an effective amount of the compound according to claim 2 or a pharmaceutically acceptable salt to a subject in need thereof.

12. A method or treating Type II diabetes, comprising:
administering an effective amount of the compound according to claim 1 or a pharmaceutically acceptable salt thereof to a subject in need thereof.

13. A method of treating Type II diabetes, comprising:
administering an effective amount of the compound according to claim 2 or a pharmaceutically acceptable salt to a subject in need thereof.

* * * * *

SEQUENCE LISTING

<160> NUMBER OF SEQ ID NOS: 4

<210> SEQ ID NO 1
<211> LENGTH: 17
<212> TYPE: DNA
<213> ORGANISM: Artificial Sequence
<220> FEATURE:
<223> OTHER INFORMATION: Forward Primer

<400> SEQUENCE: 1
atgcctttaa accgcac                                                  17

<210> SEQ ID NO 2
<211> LENGTH: 17
<212> TYPE: DNA
<213> ORGANISM: Artificial Sequence
<220> FEATURE:
<223> OTHER INFORMATION: Reverse Primer

<400> SEQUENCE: 2
ttagttacgc tcctcgc                                                  17

<210> SEQ ID NO 3
<211> LENGTH: 30
<212> TYPE: DNA
<213> ORGANISM: Artificial Sequence
<220> FEATURE:
<223> OTHER INFORMATION: Forward Primer

<400> SEQUENCE: 3
ccctcgagac catgccttta aaccgcactt                                    30

<210> SEQ ID NO 4
<211> LENGTH: 29
<212> TYPE: DNA
<213> ORGANISM: Artificial Sequence
<220> FEATURE:
<223> OTHER INFORMATION: Reverse Primer

<400> SEQUENCE: 4
ggtctagatt agttacgctc ctcgcccag                                     29